(12) United States Patent
Hamorsky et al.

(10) Patent No.: US 12,343,375 B2
(45) Date of Patent: Jul. 1, 2025

(54) SPRAY DRIED FORMULATION OF A CHOLERA TOXIN B SUBUNIT VARIANT

(71) Applicant: University of Louisville Research Foundation, Inc., Louisville, KY (US)

(72) Inventors: Krystal Hamorsky, Owensboro, KY (US); Nobuyuki Matoba, Owensboro, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 17/650,386

(22) Filed: Feb. 9, 2022

(65) Prior Publication Data

US 2022/0249601 A1 Aug. 11, 2022

Related U.S. Application Data

(60) Provisional application No. 63/147,521, filed on Feb. 9, 2021.

(51) Int. Cl.
| | | |
|---|---|---|
| A61K 38/00 | (2006.01) | |
| A61K 9/00 | (2006.01) | |
| A61K 9/16 | (2006.01) | |
| A61K 38/16 | (2006.01) | |
| C07K 14/00 | (2006.01) | |
| C07K 14/28 | (2006.01) | |

(52) U.S. Cl.
CPC .......... *A61K 38/164* (2013.01); *A61K 9/0053* (2013.01); *A61K 9/1623* (2013.01); *A61K 9/1694* (2013.01)

(58) Field of Classification Search
CPC .. A61K 38/164; A61K 9/0053; A61K 9/1623; A61K 9/1694; A61K 38/00; A61K 9/00; A61K 9/16; C07K 14/28
See application file for complete search history.

(56) References Cited

U.S. PATENT DOCUMENTS

| | | | |
|---|---|---|---|
| 2,909,462 | A | 10/1959 | Warfield et al. |
| 4,464,763 | A | 8/1984 | Mohler |
| 5,888,789 | A | 3/1999 | Rodriguez |
| 6,218,864 | B1 | 4/2001 | Young et al. |
| 6,395,964 | B1 | 5/2002 | Amtzen et al. |
| 6,777,546 | B2 | 8/2004 | Langridge et al. |
| 7,041,296 | B1 | 5/2006 | Stober et al. |
| 7,556,806 | B2 | 7/2009 | Wang |
| 10,066,238 | B2 | 9/2018 | Matoba et al. |
| 10,160,789 | B2 * | 12/2018 | Matoba ............... C07K 14/28 |
| 10,758,605 | B2 | 9/2020 | Matoba et al. |
| 11,524,062 | B2 | 12/2022 | Matoba et al. |
| 2002/0055618 | A1 | 5/2002 | Langridge et al. |
| 2002/0159958 | A1 | 10/2002 | Hiatt et al. |
| 2003/0021803 | A1 | 1/2003 | Langridge et al. |
| 2003/0165543 | A1 | 9/2003 | Langridge et al. |
| 2003/0191076 | A1 | 10/2003 | Wesselingh et al. |
| 2004/0043003 | A1 | 3/2004 | Chen |
| 2004/0110930 | A1 | 6/2004 | Reinl et al. |
| 2005/0044588 | A1 | 2/2005 | Langridge et al. |
| 2005/0186219 | A1 | 8/2005 | Langridge et al. |
| 2005/0241023 | A1 | 10/2005 | Hein et al. |
| 2005/0241024 | A1 | 10/2005 | Langridge et al. |
| 2005/0244424 | A1 | 11/2005 | Wang |
| 2005/0277635 | A1 | 12/2005 | Bornemann et al. |
| 2006/0199778 | A1 | 9/2006 | Ellis-Behnke et al. |
| 2006/0211087 | A1 | 9/2006 | Roosild et al. |
| 2006/0252096 | A1 | 11/2006 | Zha et al. |
| 2006/0286096 | A1 | 12/2006 | Swain et al. |
| 2007/0041981 | A1 | 2/2007 | Howard et al. |
| 2007/0192905 | A1 | 8/2007 | Piller et al. |
| 2008/0060092 | A1 | 3/2008 | Dickey et al. |
| 2008/0187954 | A1 | 8/2008 | Kallmeier et al. |
| 2008/0233083 | A1 | 9/2008 | Ansari |
| 2008/0279877 | A1 | 11/2008 | Yusibov et al. |
| 2009/0081256 | A1 | 3/2009 | Langridge et al. |
| 2009/0155297 | A1 | 6/2009 | Mrsny |
| 2009/0214570 | A1 | 8/2009 | Mrsny et al. |
| 2010/0303835 | A1 | 12/2010 | Gocke et al. |
| 2012/0100171 | A1 | 4/2012 | Henry |
| 2012/0100609 | A1 | 4/2012 | Crawford et al. |
| 2014/0286986 | A1 | 9/2014 | Matoba et al. |
| 2015/0368661 | A1 | 12/2015 | Matoba et al. |

(Continued)

FOREIGN PATENT DOCUMENTS

| | | |
|---|---|---|
| WO | WO 91/002071 A2 | 2/1991 |
| WO | WO 95/006128 A3 | 3/1995 |

(Continued)

OTHER PUBLICATIONS

Feng et al., "Retrograde transport cholera toxin from the plasma membrane to the endoplasmic reticulum requires the trans-Golgi network but not the Golgi apparatus in Exo2-treated cells," EMBO reports, 2004, 5(6): 596-601. (Year: 2004).*
Jertborn et al., "Local and Systemic Immune Responses to Rectal Administration of Recombinant Cholera Toxin B Subunit in Humans," Infection and Immunity, Jun. 2001, 69(6): 4125-4128. (Year: 2001).*
Zhu et al., "Large intestine-targeted nanoparticle-releasing oral vaccine to control genitorectal viral infection," Nat. Med., Aug. 2012, 18(8): 1291-1296, enclosed pp. 1-14. (Year: 2012).*
Reeves et al., "Spray-Dried Formulation of Epicertin, a Recombinant Cholera Toxin B subunit Variant That Induces Mucosal Healing," Pharmaceutics, Apr. 18, 2021, 13(4), pp. 1-13. (Year: 2021).*
Ajmera, et al., "Stabilisation of proteins via mixtures of amino acids during spray drying," Int. J. Pharm. 2014, 463, 98-107.

(Continued)

*Primary Examiner* — Julie Ha
(74) *Attorney, Agent, or Firm* — Hamilton, Brook, Smith & Reynolds, P.C.

(57) ABSTRACT

Powder compositions and pharmaceutical compositions comprising a cholera toxin B subunit variant and a saccharide excipient are described. Methods of making the powder compositions and methods of treating a disease or enhancing wound healing using the pharmaceutical compositions are described. Liquid compositions comprising a cholera toxin B subunit variant and mannitol are described.

20 Claims, 12 Drawing Sheets

Specification includes a Sequence Listing.

(56) References Cited

U.S. PATENT DOCUMENTS

| | | | |
|---|---|---|---|
| 2019/0085036 A1* | 3/2019 | Matoba | C12N 15/8258 |
| 2019/0111123 A1 | 4/2019 | Matoba et al. | |
| 2021/0003870 A1 | 1/2021 | Kato | |
| 2021/0038708 A1 | 2/2021 | Matoba et al. | |

FOREIGN PATENT DOCUMENTS

| | | |
|---|---|---|
| WO | WO 98/016247 A1 | 4/1998 |
| WO | 2012/045082 A2 | 4/2012 |
| WO | 2012/098119 A2 | 7/2012 |
| WO | WO 2012/125720 A2 | 9/2012 |
| WO | WO 2013/148258 A1 | 10/2013 |
| WO | 2015/009853 A1 | 1/2015 |
| WO | WO 2017/004168 A1 | 1/2017 |

OTHER PUBLICATIONS

Anwer, et al., "Eluxadoline Loaded Solid Lipid Nanoparticles for Improved Colon Targeting in Rat Model of Ulcerative Colitis," Pharmaceuticals 2020, 13, 255. (Sep. 19, 2020).

Baldauf et al., "Oral administration of a recombinant cholera toxin B subunit promotes mucosal healing in the colon," Mucosal Immunol. 2017, 10, 887-900. (Nov. 2, 2016).

Boal Carvalho et al., "Mucosal Healing in Ulcerative Colitis: A Comprehensive Review," Drugs 2017, 77, 159-173. (Jan. 11, 2017).

Borde et al., "Preparation and evaluation of a freeze-dried oral killed cholera vaccine formulation," Eur. J. Pharm. Biopharm. 2011, 79, 508-518.

Cooper et al., "Clinicopathologic study of dextran sulfate sodium experimental murine colitis," Lab. Investig. 1993, 69, 238-249.

Danese et al., "Positioning Therapies in Ulcerative Colitis," Clin. Gastroenterol. Hepatol. 2020, 18, 1280-1290.e1.

Fell et al., "Management of ulcerative colitis," Arch. Dis. Child. 2016, 101, 469-474. (Nov. 9, 2015).

Feuerstein et al., "Ulcerative Colitis," Mayo Clin. Proc. 2019, 94, 1357-1373.

Feuerstein et al., "Ulcerative colitis: Epidemiology, diagnosis, and management," Mayo Clin. Proc. 2014, 89, 1553-1563.

Gallo et al., "Surgery in ulcerative colitis: When? How?" Best Pract. Res. Clin. Gastroenterol. 2018, 32-33, 71-78.

Goins et al., "Thermal stability and intersubunit interactions of cholera toxin in solution and in association with its cell-surface receptor ganglioside GM1," Biochemistry 1988, 27, 2046-2052.

Gunnarsson et al., "Direct health care insurer and out-of-pocket expenditures of inflammatory bowel disease: Evidence from a US national survey," Dig. Dis. Sci. 2012, 57, 3080-3091.

Hamorsky et al., "Rapid and scalable plant-based production of a cholera toxin B subunit variant to aid in mass vaccination against cholera outbreaks," PLoS Negl. Trop. Dis. 2013, 7, e2046. (Mar. 7, 2013).

Hamorsky et al., "N-glycosylation of cholera toxin B subunit in Nicotiana benthamiana: Impacts on host stress response, production yield and vaccine potential," Sci. Rep. 2015, 5, 8003. (Jan. 23, 2015).

Jain et al., "Spray Drying in Pharmaceutical Industry: A Review," Res. J. Pharm. Dos. Forms Technol. 2012, 4, 74-79.

Kim et al., "Investigating intestinal inflammation in DSS-induced model of IBD," J. Vis. Exp. 2012, 3678. (Feb. 1, 2012).

Koziolek et al., "Investigation of pH and Temperature Profiles in the GI Tract of Fasted Human Subjects Using the Intellicap® System," J. Pharm. Sci. 2015, 104, 2855-2863.

Langford et al., "Drying technologies for biopharmaceutical applications: Recent developments and future direction," Dry. Technol. 2018, 36, 677-684.

Lautenschlager et al., "Drug delivery strategies in the therapy of inflammatory bowel disease," Adv. Drug Deliv. Rev. 2014, 71, 58-76.

Leoni et al., "Wound repair: Role of immune-epithelial interactions," Mucosal Immunol. 2015, 8, 959-968. (Jul. 15, 2015).

Liao et al., "Investigation of the stabilisation of freeze-dried lysozyme and the physical properties of the formulations," Eur. J. Pharm. Biopharm. 2004, 58, 15-24.

Maltesen et al., "Drying methods for protein pharmaceuticals," Drug Discov. Today Technol. 2008, 5, c81-c88.

Maury et al., "Effects of process variables on the powder yield of spray-dried trehalose on a laboratory spray-dryer," Eur. J. Pharm. Biopharm. 2005, 59, 565-573.

Morris et al., "Isolation and detection of a KDEL-tagged recombinant cholera toxin B subunit from Nicotiana benthamiana," Process Biochem. 2021, 101, 42-49.

Naini, V,. "Physical and Chemical Stability of Spray Dried Sugars and Protein-Sugar Molecular Mixtures for Inhalation," Ph.D. Thesis, Virginia Commonwealth University, Richmond, VA, USA, 1996.

Nugent et al., "Intestinal luminal pH in inflammatory bowel disease: Possible determinants and implications for therapy with aminosalicylates and other drugs," Gut 2001, 48, 571-577.

Ohrem et al., "Why is mannitol becoming more and more popular as a pharmaceutical excipient in solid dosage forms?" Pharm. Dev. Technol. 2014, 19, 257-262.

Pastor et al., "Cellulose acetate phthalate microparticles containing Vibrio cholerae: Steps toward an oral cholera vaccine," J. Drug Target. 2014, 22, 478-487.

Pearson & Lipman, "Improved tools for biological sequence comparison," Proc. Nat'l. Acad. Sci. USA 85:2444 (Apr. 1988).

Pineton de Chambrun et al., "Current evidence supporting mucosal healing and deep remission as important treatment goals for inflammatory bowel disease," Expert Rev. Gastroenterol. Hepatol. 2016, 10, 915-927.

Rowe et al., "Handbook of Pharmaceutical Excipients;" Libros Digitales-Pharmaceutical Press: London, UK, 2009.

Royal et al., "Repeated Oral Administration of a KDEL-tagged Recombinant Cholera Toxin B Subunit Effectively Mitigates DSS Colitis Despite a Robust Immunogenic Response," Toxins 2019, 11, 678. (Nov. 20, 2019).

Royal et al., "Therapeutic Potential of Cholera Toxin B Subunit for the Treatment of Inflammatory Diseases of the Mucosa," Toxins 2017, 9, 379. (Nov. 23, 2017).

Royal et al., "A modified cholera toxin B subunit containing an ER retention motif enhances colon epithelial repair via an unfolded protein response," FASEB J. 2019, 33, 13527-13545.

Smith & Waterman, "Comparison of Biosequences," Adv. Appl. Math. 2:482 (1981).

Sollohub et al., "Spray drying technique: II. Current applications in pharmaceutical technology," J. Pharm. Sci. 2010, 99, 587-597.

Surewicz et al., "Structure, stability, and receptor interaction of cholera toxin as studied by Fourier-transform infrared spectroscopy," Biochemistry 1990, 29, 8106-8111.

Tian et al., "Calorimetric investigation of protein/amino acid interactions in the solid state," Int. J. Pharm. 2006, 310, 175-186.

The Facts about Inflammatory Bowel Diseases; Crohn's & Colitis Foundation: New York, NY, USA, 2014.

Tripathi et al., "New developments in ulcerative colitis: Latest evidence on management, treatment, and maintenance," Drugs Context 2019, 8, 212572.

Wirtz et al., "Chemically induced mouse models of acute and chronic intestinal inflammation," Nat. Protoc. 2017, 12, 1295-1309.

Yadav et al., "Gastrointestinal stability of therapeutic anti-TNF α IgG1 monoclonal antibodies," Int. J. Pharm. 2016, 502, 181-187.

Zhang et al., "The 2.4 A crystal structure of cholera toxin B subunit pentamer: Choleragenoid," J. Mol. Biol. 1995, 251, 550-562.

Zhang et al., "Inflammatory bowel disease: Pathogenesis," World J. Gastroenterol. 2014, 20, 91-99. (Jan. 7, 2014).

F. F. Anhe et al, A polyphenol-rich cranberry extract protects from diet-induced obesity, insulin resistance and intestinal inflammation in association with increased Akkermansia spp. population in the gut microbiota of mice. Gut 64, 872-883 (2015).

Arakawa, et al. (1997). "Expression of cholera toxin B subunit oligomers in transgenic potato plants," Transgenic Research, vol. 6, pp. 403-413.

(56) References Cited

OTHER PUBLICATIONS

Asford, C. Thivolet. Nasal administration of CTB-insulin induces active tolerance against autoimmune diabetes in non-obese diabetic (NOD) mice. Clin Exp Immunol 130. 204-211 (2002).
Baldauf, et al., "Cholera toxin B: one subunit with many pharmaceutical applications," Toxins (Basel) 7, 974-996 (2015).
S. Baindur-Hudson, A L. Edkins, G. L. Blatch, Hsp70/Hsp90 organising protein (hop): beyond interactions with chaperones and prion proteins. Subcell Biochem 78, 69-90 (2015).
P. Balogh, S. Katz, A. L. Kiss, "The role of endocytic pathways in TGF-beta signaling," Pathol Oncol Res 19, 141-148 (2013).
Balzarini J., "Targeting the glycans of glycoproteins: a novel paradigm for antiviral therapy," Nat Rev Microbiol. 2007; 5(8): 583-97.
G. Bamias, G. Kaltsa, S. D. Ladas, Cytokines in the pathogenesis of ulcerative colitis. DiscovMed 11, 459-467 (2011).
Bezzio, F. Furfaro, R. de Franchis, G. Maconi, A. K. Asthana, S. Ardizzone. Ulcerative colitis: current pharmacotherapy and future directions. Expert Opin Pharmacother 15. 1659-1670 (2014).
P. Biancheri et al., "The role of transforming growth factor (TGF)-beta in modulating the immune response and fibrogenesis in the gut. Cytokine Growth Factor Rev 25," 45-55 (2014).
Boirivant M., et al., "Oral Administration of Recombinant Cholera Toxn Subunit B Inhibits IL-12-Mediated Murine Experimental (Trinitrobenzene Sulfonic Acide) Colitis", The Journal ofimmunology, 166(5): 3522-2532, Mar. 1, 2001.
K. Bulut et al, Glucagon-like peptide 2 improves intestinal wound healing through induction of epithelial cell migration in vitro-evidence for a TGF-beta-mediated effect. RegulPept 111, 137-143 (2004).
V. Burkart et al, Cholera toxin B pretreatment of macrophages and monocytes diminishes their proinflammatory responsiveness to lipopolysaccharide. J Immunol 168, 1730-1737 (2002).
J. S. Chen et al., Secreted heat shock protein 90alpha induces colorectal cancer cell invasion through CD91/LRP-1 and NF-kappaB-mediated integrin alphaV expression. The Journal ofbiological chemistry 285, 25458-25466 (2010).
Clemens, et al., "New-generation vaccines against cholera," Nature reviews. Gastroenterology & hepatology 8, 701-710 (2011).
Coccia, E.M., et al., "Cholera toxin subunit B inhibits IL-12 and IFN-y production and signaling in experimental colitis and Crohn's disease", Gut, 54(11): 1558-1564, Nov. 1, 2005.
R. Cutroneo, TGF-beta-induced fibrosis and SMAD signaling: oligo decoys as natural therapeutics for inhibition of tissue fibrosis and scarring. Wound Repair Regen 15 Suppl 1, S54-60 (2007).
J. Dabritz et al., Reprogramming of monocytes by GM-CSF contributes to regulatory immune functions during intestinal inflammation. J Immunol 194, 2424-2438 (2015).
D'Ambrosio, M. Colucci, 0. Pugliese, F. Quintieri, M. Boirivant, Cholera toxin B subunit promotes the induction of regulatory T cells by preventing human dendritic cell maturation. JLeukoc Biol 84, 661-668 (2008).
J. M. Davies, M. T. Abreu. The innate immune system and inflammatory bowel disease. Scand J Gastroenterol 50. 24-33 (2015).
P. Desreumaux, S. Ghosh, Review article: mode of action and delivery of 5-aminosalicylic acid—new evidence. Aliment Pharmacol Ther 24 Suppl 1, 2-9 (2006).
A. Dieleman et al, Chronic experimental colitis induced by dextran sulphate sodium (DSS) is characterized by Th1 and Th2 cytokines. Clin Exp Immunol 114, 385-391 (1998).
Doulberis et al, Cholera-toxin suppresses carcinogenesis in a mouse model of inflammation-driven sporadic colon cancer. Carcinogenesis 36, 280-290 (2015).
Dowdy and Wearden, Statistics for Research, John Wiley & Sons, New York, 1983.
Emedicine health, https://www.emedicinehealth.com/colon_cancer_symptoms_vs ulcerative_colitis/topic-guide .htm, accessed on Dec. 18, 2019 (Year: 2019).

A. Engel, M. Khalil, M. F. Neurath, Highlights in inflammatory bowel disease-from bench to bedside. Clinical chemistry and laboratory medicine: CCLM / FESCC 50, 1229-1235 (2012).
Fensterle, J., et al., "Cancer immunotherapy based on recombinant *Salmonella enterica* serovar Typhimurium aroA strains secreting prostate-specific antigen and cholera toxin subunit B", Cancer Gene Therapy, (2008) 15, 85-93.
F. Furfaro, C. Bezzio, S. Ardizzone, A Massari, R. de Franchis, G. Maconi. Overview of biological therapy in ulcerative colitis: current and future directions. J Gastrointestin Liver Dis 24. 203-213 (2015).
Geremia, P. Biancheri, P. Allan, G. R. Corazza, A. Di Sabatino, Innate and adaptive immunity in inflammatory bowel disease. Autoimmun Rev 13, 3-10 (2014).
Gleba et al., "Magnifection—a new platform for expressing recombinant vaccines in plants," Vaccine. 2005; 23(17-18): 2042-8.
M. Globig et al, Comprehensive intestinal T helper cell profiling reveals specific accumulation of IFN-gamma IL-17 coproducing CD4+ T cells in active inflammatory bowel disease. Inflamm Bowel Dis 20, 2321-2329 (2014).
Gloudemans et al., "The mucosal adjuvant cholera toxin B instructs non-mucosal dendritic cells to promote IgA production via retinoic acid and TGF-bcta," PLoS One 8, c59822 (2013).
Gonzalez, et al., "Signaling mechanisms of the epithelial-mesenchymal transition," Science signaling 7, re8 (2014).
M. Gross, T. Jvi. Salame, S. Jung. Guardians of the Gut—Murine Intestinal Macrophages and Dendritic Cells. Frontiers in immunology 6. 254 (2015).
Guo et al., "Prophylactic and therapeutic efficacy of the epitope vaccine CTB-UA against Helicobacter pylori infection in a BALB/c mice model," Applied microbiology and biotechnology 95, 1437-1444 (2012).
F. Gutierrez-Orozco et al, Intestinal microbial dysbiosis and colonic epithelial cell hyperproliferation by dietary alpha-mangostin is independent of mouse strain. Nutrients 7, 764-784 (2015).
Hameedaldeen, J. Liu, A. Batres, G. S. Graves, D. T. Graves, FOXO1, TGF-beta regulation and wound healing. International journal of molecular sciences 15, 16257-16269 (2014).
Holmgren et al., "Mucosa! adjuvants and anti-infection and anti-immunopathology vaccines based on cholera toxin, cholera toxin B subunit and CpG DNA," Immunology letters 97, 181-188 (2005).
Immobilized Cells And Enzymes, IRL Press, 1986.
Irache JM, et al., "Mannose-targeted systems for the delivery of therapeutics," Expert Opin Drug Deliv. 2008; 5(6): 703-24.
A. Irizarry, B. Hobbs, F. Collin, Y. D. Beazer-Barclay, K. J. Antonellis, U. Scherf, T. P. Speed. Exploration, normalization, and summaries of high density oligonucleotide array probe level data. Biostatistics 4. 249-264 (2003).
G. Jego, A Hazoume, R. Seigneuric, C. Garrido, Targeting heat shock proteins in cancer. Cancer Lett 332, 275-285 (2013).
Jelinek, et al., "Vaccination with Dukoral against travelers' diarrhea (ETEC) and cholera," Expert Rev Vaccines 7, 561-567 (2008).
Jiang et al (Transgenic Res., 2007, 16:169-175) (Year: 2007).
Y. L. Jones-Hall, M. B. Grisham. Immunopathological characterization of selected mouse models of inflammatory bowel disease: Comparison to human disease. Pathophysiology 21. 267-288 (2014).
Y. Jung, M. E. Rothenberg, Roles and regulation of gastrointestinal eosinophils in immunity and disease. J Immunol 193, 999-1005 (2014).
Kang et al (Molecular Breeding, 2004, 13:143-153).
M. Kaplan, B. B. Mentes, E. Tatlicioglu, B. Kayhan, C. Aybay, Effect of mucosal immunomodulation with fed cholera toxin on healing of experimental colonic anastomosis. Discases of the colon and rectum 45, 819-825 (2002).
K. Karlinger, T. Gyorke, E. Mako, A. Mester, Z. Tarjan, The epidemiology and the pathogenesis of inflammatory bowel disease. European journal of radiology 35, 154-167 (2000).
T. Kayashima et al., Consumption of vitamin B6 reduces colonic damage and protein expression ofHSP70 and HO-1, the anti-tumor targets, in rats exposed to 1,2-dimethylhydrazine. Oncol Lett 2, 1243-1246 (2011).
Keler T, et al., "Mannose receptor-targeted vaccines," Expert opinion on biological therapy. 2004; 4(12): 1953-62.

(56) References Cited

OTHER PUBLICATIONS

V. Khattar, J. Fried, B. Xu, J. V. Thottassery, Cksl proteasomal degradation is induced by inhibiting Hsp90-mediated chaperoning in cancer cells. Cancer Chemother Pharmacol 75, 411-420 (2015).
Kiesler, I. J. Fuss, W. Strober. Experimental Models of Inflammatory Bowel Diseases. Cell Mol Gastroenterol Hepatol 1. 154-170 (2015).
P.H. Kim, L. Eckmann, W. J. Lee, W. Han, M. F. Kagnoff, Cholera toxin and cholera toxin B subunit induce IgA switching through the action of TGF-beta 1. J Immunol 160, 1198-1203 (1998).
Kothary, et al., "Purification and characterization of a Chinese hamster ovary cell elongation factor of Vibrio hollisae," Infection and immunity 63, 2418-2423 (1995).
D. C. Lacey et al, Defining GM-CSF- and macrophage-CSP-dependent macrophage responses by in vitro models. J Immunol 188, 5752-5765 (2012).
G. Latella, C. Papi, Crucial steps in the natural history of inflammatory bowel disease. World J Gastroenterol 18, 3790-3799 (2012).
Lebens, M., et al., "Synthesis of Hybrid Molecules between Heat-Labile Enterotoxin and Cholera Toxins B Subunits: Potential for Use in a Broad-Spectrum Vaccine", Infection and Immunity, Jun. 1996, 64(6); 2144-2150.
G. D. Lianos et al, The role of heat shock proteins in cancer. Cancer Lett 360, 114-118 (2015).
W. Liu et al, A novel benzo[d]imidazole derivate prevents the development of dextran sulfate sodium-induced murine experimental colitis via inhibition ofLRP3 inflammasome. Biochem Pharmacol 85, 1504-1512 (2013).
T. Lysakova-Devine, C. O'Farrelly. Tissue-specific NK cell populations and their origin. JLeukoc Biol 96. 981-990 (2014).
D. Ma, D. Wolvers, A. M. Stanisz, J. Bienenstock. Interleukin-IO and nerve growth factor have reciprocal upregulatory effects on intestinal epithelial cells. Am J Physiol Regul Integr Comp Physiol ' 284. R1323-1329 (2003).
Marillonnet S, et al., "In planta engineering of viral RNA replicons: efficient assembly by recombination of DNA modules delivered by Agrobacterium," Proc Natl Acad Sci US A. 2004; 101(18): 6852-7.
Matoba N,, et al., "A mucosally targeted subunit vaccine candidate eliciting HIV-I transcytosis-blocking Abs," Proc Natl Acad Sci US A. 2004; 101(37): 13584-9.
Matoba N, et al., "Transcytosis-blocking Abs elicited by an oligomeric immunogen based on the membrane proximal region of HIV-I gp41 target non-neutralizing epitopes," Curr HIV Res. 2008; 6(3): 218-29.
Matoba N, et al., "Recombinant Protein Expression in Nicotiana," Methods Mol Biol. 2011; 701: 199-219.
Matoba N, et al., "Humoral immune responses by prime-boost heterologous route immunizations with CTB-MPR(649-684), a mucosal subunit HIV/AIDS vaccine candidate," Vaccine. 2006; 24(23): 5047-55.
Matoba N, et al., "Biochemical and immunological characterization of the plant-derived candidate human immunodeficiency virus type 1 mucosal vaccine CTB-MPR(649-684),". Plant Biotechnol J. 2009; 7(2): 129-45.
Matos, AF. Bento, R. Marcon, R. F. Claudino, J.B. Calixto, Preventive and therapeutic oral administration of the pentacyclic triterpene alpha,beta-amyrin ameliorates dextran sulfate sodium-induced colitis in mice: the relevance of cannabinoid system. Mol Immunol 54, 482-492 (2013).
Mikschofsky, et al. (2009). "Cholera toxin B (CTB) is functional as an adjuvant for cytoplasmic proteins if directed to the endoplasmic reticulum (ER), but not to the cytoplasm of plants," Plant Science, vol. 177, pp. 35-42.
Mishra et al (Journal of Biotechnology, 2006, 127(1 ): 95-108).
G. Monteleone, R. Caruso, F. Pallone, Targets for new immunomodulation strategies in inflammatory bowel disease. Autoimmun Rev 13, 11-14 (2014).
P. Munkholm, Review article: the incidence and prevalence of colorectal cancer in inflammatory bowel disease. Aliment Pharmacol Ther 18 Suppl 2, 1-5 (2003).

M. F. Neurath. New targets for mucosal healing and therapy in inflammatory bowel diseases. Mucosal Immunol 7. 6-19 (2014).
Ordas, I, Eckmann, L., Talamini, M., Baumgart, DC, & Sandborn, WJ. Ulcerative Colitis. Lancet. 380(9853), 1606-19 (2012).
H. Oshima, M. Nakayama, T. S. Han, K. Naoi, X. Ju, Y. Maeda, S. Robine, K. Tsuchiya, T. Sato, H. Sato, 1\tI. M. Taketo, M. Oshima. Suppressing TGFbeta signaling in regenerating epithelia in an inflammatory microenvironment is sufficient to cause invasive intestinal cancer. Cancer Res 75. 766-776 (2015).
A Phipps, M. R. Stanford, J.B. Sun, B. G. Xiao, J. Holmgren, T. Shinnick, A Hasan, Y. Mizushima, T. Lehner. Prevention of mucosally induced uveitis with a HSP60-derived peptide linked to cholera toxin B subunit. Eur J Immunol 33. 224-232 (2003).
J. E. Qualls, H. Tuna, A. M. Kaplan, D. A Cohen. Suppression of experimental colitis in mice by CDI lc+ dendritic cells. Inflamm Bowel Dis 15 236-247 (2009).
E. Ruckova, P. JVIuller, R. Nenutil, B. Vojtesek. Alterations of the Hsp70/Hsp90 chaperone and the HOP/CHIP co-chaperone system in cancer. Cell Mol Biol Lett 17. 446-458 (2012).
Sanchez, et al., "Cholera toxin structure, gene regulation and pathophysiological and immunological aspects," Cell Mo! Life Sci 65, 1347-1360 (2008).
Sheng KC, et al., "Delivery of antigen using a novel mannosylated dendrimer potentiates immunogenicity in vitro and in vivo," Eur J Immunol. 2008; 38(2): 424-36.
R. Siegel, D. Naishadham, A. Jemal, Cancer statistics, 2012. CA Cancer J Clin 62, 10-29 (2012).
M. H. Zaki, M. Lamkanfi, T. D. Kanneganti, The Nlrp3 inflammasome: contributions to intestinal homeostasis. Trends Immunol 32, 171-179 (2011).
H. H. Smits et al., Cholera toxin B suppresses allergic inflammation through induction of secretory IgA. Mucosal Immunol 2, 331-339 (2009).
Sola et al (Biodrugs, 2010, 24(1): 9-21) (Year: 2010).
M. Stahle-Backdahl, J. Maim, B. Veress, C. Benoni, K. Bruce, A Egesten. Increased presence of eosinophilic granulocytes expressing transforming growth factor-beta! in collagenous colitis. Scand J Gastroenterol 35. 742-746 (2000).
Stal, P., et al., "Clinical trial: the safety and short-term efficacy of recombinant cholera toxin B subunit in the treatment of active Crohns' disease", Alimentary Pharmacology & Therapeutics, 31:3 387-395, Feb. 1, 2010.
Stanford et al., "Oral tolerization with peptide 336-351 linked to cholera toxin B subunit in preventing relapses ofuveitis in Behcet's disease," Clin Exp Immunol 137, 201-208 (2004).
Sturm, AU. Dignass, Epithelial restitution and wound healing in inflammatory bowel discasc. World J Gastroenterol 14, 348-353 (2008).
Sun, et al., "Mucosally induced immunological tolerance, regulatory T cells and the adjuvant effect by cholera toxin B subunit," Scand J Immunol 71, 1-11 (2010).
J.B. Sun, B. G. Xiao, M. Lindblad, B. L. Li, H. Link, C. Czerkinsky, J. Holmgren. Oral administration of cholera toxin B subunit conjugated to myelin basic protein protects against experimental autoimmune encephalomyelitis by inducing transforming growth factor-beta-secreting cells and suppressing chemokine expression. Int Immunol 12. 1449-1457 (2000).
J.B. Sun, B. L. Li, C. Czerkinsky, J. Holmgren. Enhanced immunological tolerance against allograft rejection by oral administration of allogeneic antigen linked to cholera toxin B subunit. Clin Immunol 91. 130-139 (2000).
K. Suzuki, X. Sun, M. Nagata, T. Kawase, H. Yamaguchi, V. Sukumaran, Y. Kawauchi, H. Kawachi, T. Nishino, K. Watanabe, H. Yoneyama, H. Asakura. Analysis of intestinal fibrosis in chronic colitis in mice induced by dextran sulfate sodium. Pathol Int 61. 228-238 (2011).
B. P. Vaughn, S. Shah, AS. Cheifetz. The role of mucosal healing in the treatment of patients with inflammatory bowel disease. Curr Treat Options Gastroenterol 12. 103-117 (2014).
Y. Wang et al, Tumor-derived GM-CSF promotes inflammatory colon carcinogenesis via stimulating epithelial release of VEGF. Cancer Res 74, 716-726 (2014).

(56) References Cited

OTHER PUBLICATIONS

N. A Williams, T. R. Hirst, T. 0. Nashar, Immune modulation by the cholera-like enterotoxins: from adjuvant to therapeutic. Immunology today 20, 95-101 (1999).
N. A Williams, Immune modulation by the cholera-like enterotoxin B-subunits: from adjuvant to immunotherapeutic. International journal of medical microbiology: IJMM 290, 447-453 (2000).
S. Wirtz, C. Neufert, B. Weigmann, M. F. Neurath, Chemically induced mouse models of intestinal inflammation. Nature protocols 2, 541-546 (2007).
Yue, Z. Shen, C.H. Yu, H. Ye, Y. M. Li, The therapeutic role of oral tolerance in dextran sulfate sodium-induced colitis via Thl-Th2 balance and gammadelta T cells. Journal of digestive diseases 14, 543-551 (2013).
Yuki et al., "Oral MucoRice expressing double-mutant cholera toxin A and B subunits induces toxin-specific neutralizing immunity", Vaccine, 2009; 27: 5982-5988 (Year: 2009).
Zhang et al., "The 2.4 A crystal structure of cholera toxin B subunit pentamer: choleragenoid," Journal of molecular biology 251, 550-562 (1995).
GENBANK® accession No. P27932; Retrieved Jul. 29, 2021.
GENBANK® accession No. Z71395; Retrieved Jul. 28, 2021.
GENBANK® accession No. P48978; Retrieved Jul. 28, 2021.
GENBANK® accession No. CAX51374; Retrieved Jul. 28, 2021.
GENBANK® Accession No. AY475128; Retrieved Jul. 28, 2021.
GENBANK® Accession No. AAC60441; Retrieved Jul. 28, 2021.
GENBANK® accession No. U25679, nucleotide 1 to 63; Retrieved Jul. 28, 2021.
Sigma-Aldrich #G-7641; Retrieved Jul. 28, 2021.
Sigma-Aldrich, #C9903; Retrieved Jul. 28, 2021.
Clontech No. 635670; Retrieved Jul. 28, 2021.
List Biological Laboratories# 703; Retrieved Jul. 29, 2021.
Tris Glycine gels (Catalog No. 58510); Retrieved Jul. 28, 2021.
Sigma, Catalog No. A5420; Retrieved Jul. 28, 2021.
TMB Super Sensitive HRP Substrate, BioFX Laboratories# TMBS-1000-01 (Jan. 22, 2007).
Dulbecco's PBS (Gibco No. 14190); 1954.
Cayman Chemical Company No. 10009437; Retrieved Jul. 28, 2021.
New England BioLabs (Catalog No. P0703S); Retrieved Jul. 28, 2021.
New England BioLabs (Catalog No. P0704S); Retrieved Jul. 28, 2021.
ISA/KR. International Preliminary Report on Patentability and Written Opinion issued in related international application No. PCT/US2012/029072, issued Sep. 17, 2013.
ISA/KR, International Search Report issued in related international application No. PCT/US2012/029072, mailed Sep. 24, 2012.
Office Action for U.S. Appl. No. 14/005,388, "Polypeptides Having Immunoactivating Activity And Methods Of Producing The Same" dated Dec. 19, 2016.
Final Office Action for U.S. Appl. No. 14/005,388, "Polypeptides Having Immunoactivating Activity And Methods Of Producing The Same" dated Apr. 7, 2017.
Office Action for U.S. Appl. No. 14/005,388, "Polypeptides Having Immunoactivating Activity And Methods Of Producing The Same" dated Jan. 25, 2018.
Notice of Allowance for U.S. Appl. No. 14/005,388, "Polypeptides Having Immunoactivating Activity And Methods Of Producing The Same" dated Aug. 9, 2018.
Office Action for U.S. Appl. No. 16/201,585, "Polypeptides Having Immunoactivating Activity And Methods Of Producing The Same," dated Apr. 29, 2021.
Supplemental European Search Report for EP Application No. 16818658, "Compositions And Methods For Treating Cancer And Promoting Wound Healing", dated Dec. 19, 2018.
International Search Report and Written Opinion for International Application No. PCT/US2016/040041, entitled "Compositions And Methods For Treating Cancer And Promoting Wound Healing," consisting of 4 pages. Date of Mailing: Dec. 5, 2016.
International Preliminary Report on Patentability and Written Opinion for International Application No. PCT/US2016/040041, entitled "Compositions And Methods For Treating Cancer And Promoting Wound Healing," Date of Mailing: Dec. 5, 2016.
Non-Final Office Action for U.S. Appl. No. 15/740,622, entitled "Compositions And Methods For Treating Cancer And Promoting Wound Healing," dated May 13, 2019.
Final Office Action for U.S. Appl. No. 15/740,622, entitled "Compositions And JVIethods For Treating Cancer And Promoting Wound Healing," dated Dec. 26, 2019.
Notice of Allowance for U.S. Appl. No. 15/740,622, entitled "Compositions And Methods For Treating Cancer And Promoting Wound Healing," dated Apr. 3, 2020.
Final Office Action for U.S. Appl. No. 16/201,585, entitled "Polypeptides Having Immunoactivating Activity And Methods Of Producing The Same," dated Nov. 12, 2021.
2012. Global report: UNAIDS report on the global AIDS epidemic { 2012. Joint United Nations Programme on HIV/AIDS.
Abdool Karim Q, et al. 2010. Effectiveness and safety of tenofovir gel, an antiretroviral microbicide, for the prevention of HIV infection in women. Science 329:1168-1174.
Abela IA, et al. 2012. Cell-cell transmission enables HIV-1 to evade inhibition by potent CD4bs directed antibodies. PLoS Pathog. 8:e1002634.
Alexandre KB, et al. 2011. Binding of the Mannose-Specific Lectin, Griffithsin, to HIV-1 gp120 Exposes the CD4-Binding Site. J. Virol. 85:9039-9050.
Blish CA, et al. 2009. Cross-subtype neutralization sensitivity despite monoclonal antibody resistance among early subtype A, C, and D envelope variants of human immunodeficiency virus type 1. J. Virol. 83:7783-7788.
Bosch D, et al. 2010. Plant glycans: friend or foe in vaccine development? Expert Rev. Vaccines 9:835-842.
Buckheit KW, et al. 2012. Factors Important to the Prioritization and Development of Successful Topical Microbicides for HIV-1. Mol. Biol. Int. 2012:781305. doi:10.1155/2012/781305.
Burton DR, et al. 2011. Limited or no protection by weakly or nonneutralizing antibodies against vaginal SHIV challenge of macaques compared with a strongly neutralizing antibody. Proc. Natl. Acad. Sci. U.S.A. 108:11181-11186.
Castilho A,et al. 2011. Rapid high yield production of different glycoforms of Ebola virus monoclonal antibody. PLoS One 6:e26040.
Clapham PR, Lu S., Vaccinology: Precisely tuned antibodies nab HIV, Nature. Sep. 21, 2011, 416-17 and supplementary information, 477(7365).
Deng H, et al. 1996. Identification of a major co-receptor for primary isolates of HIV-1. Nature 381:661-666.
Diskin R, et al. 2011. Increasing the potency and breadth of an HIV antibody by using structure-based rational design. Science 334:1289-1293.
Fields J, et a., (1960) "Synthetic polyelectrolyte4s as tumour inhibitors" Nature 186: 778-780.
Forthal DN, et al. 2009. Fc receptor-mediated antiviral antibodies. Cur. Opin. HIV AIDS 4:388-393.
Forthal DN, et al. 2010. Fc-glycosylation influences Fcgamma receptor binding and cell-mediated anti-HIV activity of monoclonal antibody 2G12. J. Immunol. 185:6876-6882.
GenBank Accession No. CAA00098.1 (published Dec. 2005).
GenBankAccession No. AAD51360.1 (published Nov. 1999).
Giritch A, et al. 2006. Rapid high-yield expression of full-size IgG antibodies in plants coinfected with noncompeting viral vectors. Proc. Natl. Acad. Sci. U.S.A. 103:14701-14706.
Goodin et al. "Nicotiana benthamiana: Its History and Future as a Model for Plant—Pathogen Interactions", Mol. Plant-Micobe Interact. 2008; 21(9): 1015-1026.
Hessell AJ, et al. 2007. Fc receptor but not complement binding is important in antibody protection against HIV. Mature 449:101-104.
Hessell AJ, et al. 2009. Broadly neutralizing human anti-HIV antibody 2G12 is effective in protection against mucosal SHIV challenge even at low serum neutralizing titers. PLoS Pathog. 5:e1000433.
Hessell AJ, et al. 2010. Broadly Neutralizing Monoclonal Antibodies 2F5 and 4E10, Directed Against the Human Immunodeficiency

(56) References Cited

OTHER PUBLICATIONS

Virus Type 1 (HIV-1) gp41 Membrane Proximal External Region (MPER), Protect Against SHIVBa-L Mucosal Challenge. J. Virol. 84:1302-1313.
Holmes D. 2012. FDA treads carefully with PrEP. Lancet Infect. Dis. 12:515-516.
Hong, Li , et al. (1996). "Immunocytochemical Characterization of CD44 Molecules Expressed in Human Brain Metastases." Pharmeuropa. vol. 8, No. 2.
Huang J, et al. Broad and potent neutralization of HIV-1 by a gp41-specific human antibody. Nature 2012 491:406-412.
Huang Z, et al. 2009. High-level rapid production of full-size monoclonal antibodies in plants by a single-vector DNA replicon system. Biotechnol. Bioeng. 106:9-17.
International Preliminary Report on Patentability received for PCT Patent Application No. PCT/US2014/015861, mailed on Aug. 20, 2015, 30 pages.
International Search Report and Written Opinion received for PCT Patent Application No. PCT/US2014/015861, mailed on May 24, 2014, 17 pages.
J. B. Sun, C. Czerkinsky, J. Holmgren. B Lymphocytes Treated In Vitro with Antigen Coupled to Cholera Toxin B Subunit Induce Antigen-Specific Foxp3(+) Regulatory T Cells and Protect against Experimental Autoimmune Encephalomyelitis. Journal of Immunology '188. 1686-1697 (2012).
Jin C, et al. 2008. A plant-derived human monoclonal antibody induces an anti-carbohydrate immune response in rabbits. Glycobiology 18:235-241.
Kinal H, et al. 1995. Processing and secretion of a virally encoded antifungal toxin in transgenic tobacco plants: evidence for a Kex2p pathway in plants. Plant Cell 7:677-688.
Klein F, et al. 2012. HIV therapy by a combination of broadly neutralizing antibodies in humanized mice. Nature 492:118-122.
Klinman et al., (1996). "Cpg motifs present in bacterial DNA rapidly induce lymphocytes to secrete interleukin 6, interleukion 12, and interferon •. " Proc. Natl. Acad. Sci., USA, 93:2879-2883. WO98/16247.
Ko, Brodzik, & Steplewski, Production of Antibodies in Plants: Approaches and Perspectives. A.V. Karasev (ed.) Plant-produced Microbial Vaccines. 55, Current Topics in Microbiology and Immunology 332 @ Springer-Verlag Berlin Heidelberg 2009.
Korean Intellectual Property Office, International Search Report issued in corresponding Application No. PCT/US2014/015861, dated May 28, 2014.
Kouokam JC, et al. 2011. Investigation of griffithsin's interactions with human cells confirms its outstanding safety and efficacy profile as a microbicide candidate. PLoS One 6:e22635.
Landau NR, et al. 1992. Packaging system for rapid production of murine leukemia virus vectors with variable tropism. J. Virol. 66:5110-5113.
Li M, et al. 2006. Genetic and Neutralization Properties of Acute and Early Subtype C Human Immunodeficiency Virus Type 1 Molecular env Clones from Heterosexually Acquired Infections in Southern Africa. J. Virol. 80:11776-11790.
Ma JK, et al. 2003. The production of recombinant pharmaceutical proteins in plants. Nat. Rev. Genet. 4:794-805.
Macklin R, et al. 2012. Given financial constraints, it would be unethical to divert antiretroviral drugs from treatment to prevention. Health Aff. 31:1537-1544.
Marillonnet S, et al. 2005. Systemic Agrobacterium tumefaciens-mediated transfection of viral replicons for efficient transient expression in plants. Nat. Biotechnol. 23:718-723.
Matoba N, et al. 2010. HIV-1 neutralization profile and plant-based recombinant expression of actinohivin, an Envglycan-specific lectin devoid of T-cell mitogenic activity. PLoS One 5:e11143.
Mcgowan I. 2010. Microbicides for HIV prevention: reality or hope? Curr. Opin. Infect. Dis. 23:26-31.

Moldt B, et al. 2012. Highly potent HIV-specific antibody neutralization in vitro translates into effective protection against mucosal SHIV challenge in vivo. Proc. Natl. Acad. Sci. U.S.A. 109:18921-18925.
Monel B, et al. 2012. HIV cell-to-cell transmission requires the production of infectious virus particles and does not proceed through env-mediated fusion pores. J. Virol. 86:3924-3933.
Muynck et al. "Production of antibodies in plants: status after twenty years", Plant Biotech. J. 2010; 8: 529-563.
NCBI, GenBank accession No. CAA00066.1 (Dec. 1, 2005).
Neff CP, et al. 2011. A topical microbicide gel formulation of CCR5 antagonist maraviroc prevents HIV-1 vaginal transmission in humanized RAG-hu mice. PLoS One 6:e20209.
O'Keefe BR, et al. 2009. Scaleable manufacture of HIV-1 entry inhibitor griffithsin and validation of its safety and efficacy as a topical microbicide component. Proc. Natl. Acad. Sci. U.S.A. 106:6099-6104.
Parrish NF, et al. 2012. Transmitted/founder and chronic subtype C HIV-1 use CD4 and CCR5 receptors with equal efficiency and are not inhibited by blocking the integrin alpha4beta7. PLoS Pathog. 8:e1002686.
PCT International Preliminary Report on Patentability for International Application No. PCT/US2012/029072, entitled "Polypeptides Having Immunoactivating Activity and Methods of Producing the Same," mailed on Sep. 17, 2013.
PCT International Search Report and Written Opinion for International Application No. PCT/US2012/029072, entitled "Polypeptides Having Immunoactivating Activity and Methods of Producing the Same," mailed on Sep. 24, 2012.
Pirrone V, et al. 2011. Combinatorial approaches to the prevention and treatment of HIV-1 infection. Antimicrob. Agents Chemother. 55:1831-1842.
Pogue GP, et al. 2010. Production of pharmaceutical-grade recombinant aprotinin and a monoclonal antibody product using plant-based transient expression systems. Plant Biotechnol. J. 8:638-654.
Provine NM, et al. 2012. The neutralization sensitivity of viruses representing human immunodeficiency virus type 1 variants of diverse subtypes from early in infection is dependent on producer cell, as well as characteristics of the specific antibody and envelope variant. Virology 427:25-33.
Robinson HL. 2012. Non-neutralizing antibodies in prevention of HIV infection. Expert Opin. Biol. Ther. 13:197-207.
Sainsbury F, et al. 2009. pEAQ: versatile expression vectors for easy and quick transient expression of heterologous proteins in plants. Plant Biotechnol. J. 7:682-693.
Sattentau Q. 2008. Avoiding the void: cell-to-cell spread of human viruses. Nat. Rev. Microbiol. 6:815-826.
Selhorst P, et al. 2012. In vitro activities of candidate microbicides against cell-associated HIV. Antimicrob. Agents Chemother. 56:805-815.
Strasser R, et al. 2008. Generation of glyco-engineered Nicotiana benthamiana for the production of monoclonal antibodies with a homogeneous human-like N-glycan structure. Plant Biotechnol. J. 6:392-402.
Throsby M, et al. 2008. Heterosubtypic neutralizing monoclonal antibodies cross-protective against H5N1 and H1N1 recovered from human IgM+ memory B cells. PLoS One 3:e3942.
Van Damme L, et al. 2012. Current status of topical antiretroviral chemoprophylaxis. Curr. Opin. HIV AIDS 6:520-525.
Veazey RS, et al. 2003. Prevention of virus transmission to macaque monkeys by a vaginally applied monoclonal antibody to HIV-1 gp120. Nat. Med. 9:343-346.
Veselinovic M, et al. 2012. Topical gel formulation of broadly neutralizing anti-HIV-1 monoclonal antibody VRC01 confers protection against HIV-1 vaginal challenge in a humanized mouse model. Virology 432:505-510.
Vezina LP, et al. 2009. Transient co-expression for fast and high-yield production of antibodies with human-like N-glycans in plants. Plant Biotechnol. J. 7:442-455.
Walker LM, et al. 2011. Broad neutralization coverage of HIV by multiple highly potent antibodies. Nature 477:466-470.

(56) References Cited

OTHER PUBLICATIONS

Watkins JD, et al. 2011. An anti-HIV-1 V3 loop antibody fully protects cross-clade and elicits T-cell immunity in macaques mucosally challenged with an R5 clade C SHIV. PLoS One 6:e18207.

Wilen CB, et al. 2011. Phenotypic and immunologic comparison of clade B transmitted/founder and chronic HIV-1 envelope glycoproteins. J. Virol. 85:8514-8527.

Wu X, et al. 2010. Rational design of envelope identifies broadly neutralizing human monoclonal antibodies to HIV-1. Science 329:856-861.

Wu X, et al. 2012. Selection Pressure on HIV-1 Envelope by Broadly Neutralizing Antibodies to the Conserved CD4-Binding Site. J. Virol. 86:5844-5856.

Zeitlin L, et al. 2011. Enhanced potency of a fucose-free monoclonal antibody being developed as an Ebola virus immunoprotectant. Proc. Natl. Acad. Sci. U.S.A. 108:20690-20694.

Zhang B, et al. 2011. Coordinate expression of multiple proteins in plant cells by exploiting endogenous kex2p-like protease activity. Plant Biotechnol. J. 9:970-981.

Zhang PF, et al. 1999. Primary virus envelope cross-reactivity of the broadening neutralizing antibody response during early chronic human immunodeficiency virus type 1 infection. J. Virol. 73:5225-5230.

\* cited by examiner

SPRAY DRIED FORMULATION OF A CHOLERA TOXIN B SUBUNIT VARIANT

RELATED APPLICATION

This application claims the benefit of U.S. Provisional Application No. 63/147,521, filed on Feb. 9, 2021. The entire teachings of the above application are incorporated herein by reference.

GOVERNMENT SUPPORT

This invention was made with government support under DK123712 from U.S. National Institute of Health and under U01 HL127518 from the National Institutes of Health. The government has certain rights in the invention.

INCORPORATION BY REFERENCE OF MATERIAL IN ASCII TEXT FILE

This application incorporates by reference the Sequence Listing contained in the following ASCII text file being submitted concurrently herewith:
 a) File name: 56001009001.txt; created Jan. 6, 2022, 24,000 Bytes in size.

BACKGROUND

Ulcerative colitis (UC) is a major form of inflammatory bowel disease (IBD), characterized by chronic and relapsing inflammation of the innermost layer of the colon and rectal mucosa [1,2]. Its etiology remains poorly understood and the onset is associated with a complicated interplay of genetic and environmental factors as well as gut microbiota [3]. The disease often manifests as symptoms including: bloody diarrhea, rectal bleeding, fatigue, and weight loss [4]. However, symptom presentation often varies among patients and may change over time with increasing severity of disease [5]. The Crohn's and Colitis Foundation estimates that approximately 1.6 million Americans suffer from IBD with a total US annual financial burden between USD 14.6 billion and 31.6 billion. UC accounts for 907,000 of these cases with an annual incidence of 12.2 per 100,000 people [5]. Current Food and Drug Administration approved ulcerative colitis (UC) drugs aim to treat existing symptoms, maintain remission, and improve quality of life. Despite multiple treatment options available to UC patients, none of them can cure the disease, and up to a third of those with 30+ years of the disease will require surgical removal of the colon and rectum [5].

There are several classes of drugs used to treat UC [5]. Typically, UC treatment follows a step-up approach in which drug class utilization is dependent upon disease severity and response to prior therapies. The final step of this treatment strategy is surgical intervention [6,7]. Treatment with 5-aminosalicylates (5-ASAs) has long been the mainstay first-line therapy for mild-to-moderate UC [5,8]. This inflammation-blunting class of therapeutics are preferred for early-stage UC because of their generally innocuous side effect profiles, although moderate UC is often unresponsive to these agents [7]. The mild side effect profile is counteracted by the ability of patients to develop tolerance during remission maintenance and require new treatment strategies. Failure to achieve or maintain remission with 5-ASAs is typically followed by treatment with corticosteroids and steroid-sparing immunomodulators. An estimated two-thirds of patients receiving short-term steroid treatment for moderate to severe UC achieve remission. However, the risk of serious adverse effects limits long-term use of these agents [6-9]. Biologics (e.g., anti-TNFα and anti-integrin monoclonal antibodies) have traditionally been the final agents utilized to treat severe UC prior to surgical resection of the colon and rectum, although recent literature suggests the benefit of using biologics in earlier stages [10]. These drugs are effective in remission induction and maintenance in patients following previous treatment failures but are partnered with the serious side effects including severe infection and increased cancer risk [8,9]. Of particular note, fewer than half of patients treated with biologics are able to achieve mucosal healing, an endoscopic marker found to be highly predictive of sustained clinical remission, better quality of life, and decreased risk for colitis-associated colorectal cancer [11,12]. Further, biologics are typically more expensive than other therapeutic agents [13].

SUMMARY

There is an unmet need in ulcerative colitis (UC) therapy: agents that can directly restore the damaged epithelial barrier and facilitate mucosal healing without suppressing immune function.

In one aspect, the disclosure provides a powder comprising a spray-dried formulation of a cholera toxin B subunit variant and a saccharide excipient.

In another aspect, the disclosure provides a pharmaceutical composition for oral administration, comprising a cholera toxin B subunit variant and a saccharide excipient, wherein the pharmaceutical composition is spray-dried.

In another aspect, the disclosure provides a method of treating a disease, the method comprises administering to a subject in need thereof an effective amount of a pharmaceutical composition comprising a cholera toxin B subunit variant and a saccharide excipient, wherein the pharmaceutical composition is spray-dried.

In another aspect, the disclosure provides a method of enhancing wound healing, the method comprises administering to a subject in need thereof an effective amount of a pharmaceutical composition comprising a cholera toxin B subunit variant and a saccharide excipient, wherein the pharmaceutical composition is spray-dried.

In another aspect, the disclosure provides a method of producing an oral formulation of a cholera toxin B subunit variant, comprising:
 a) mixing a phosphate-buffered saline solution of the cholera toxin B subunit variant with a saccharide excipient; and
 b) spray drying the solution in an air stream.

In another aspect, the disclosure provides a liquid composition, wherein the liquid composition comprises a cholera toxin B subunit variant and mannitol.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

(FIG. 3A) Study design. (FIG. 3B) Mice were dosed with an EPT capsule (n=10), pre-dissolved EPT powder following gastric acid neutralization (EPT powder solution; n=9), or capsule vehicle control (n=10) on day 7 following DSS exposure. DAI scores were determined on day 14 as a combined measure of body weight recovery, stool consistency, and blood in stool; data are shown as mean±SEM. * $p<0.05$, *** $p<0.001$, one-way ANOVA with Bonferroni's multiple comparisons test.

(FIG. 4A) Representative 4× (left) and 20× (right) photomicrographs of H&E-stained distal colon tissues from each treatment group. (FIG. 4B) Histological damage scores of each treatment group in the DSS acute colitis study. * $p<0.05$, ** $p<0.01$; one-way repeated measures ANOVA with Bonferroni's multiple comparisons test.

FIG. 5A: GM1-CTB ELISA. STD EPT in pentamer has a much higher EC50 to GM1 than acid-exposed EPT which contains EPT in monomer form. FIG. 5B: CTB sandwich ELISA. STD EPT in pentamer form and acid exposed EPT monomer form can be detected in a similar manner demonstrating capacity to detect both GM1-binding pentamer and disassembled CTB molecular species. FIG. 5C: Size Exclusion (SEC)-HPLC. STD EPT elutes in pentamer form at a 17.1-minute retention time whereas acid exposed EPT elutes in monomer form at 19.3 minutes, whereby demonstrating acid dissociates pentamer EPT into monomer EPT.

DETAILED DESCRIPTION

Figure 1A:
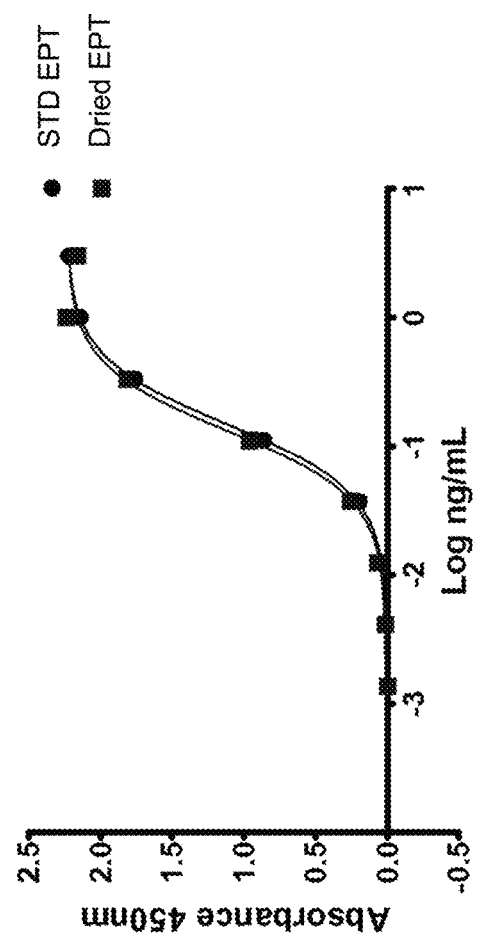
FIGS. 1A-1H depict stability assessment of spray dried EPT. The production of EPT standard is described in the methods section. The stability of dried EPT post-drying and after 9 months was assessed by GM1-capture KDEL-detection ELISA and SEC-HPLC. A representative binding curve of spray dried EPT is shown for one day post-drying (FIGS. 1A and 1E), and after 9 months stored at 23° C. in a desiccator (FIGS. 1B and 1F), compared to an EPT standard. SEC-HPLC chromatogram of non-dried EPT (FIGS. 1C and 1G) and EPT one day post-drying and dried EPT (green) after 9 months stored at 23° C. in a desiccator (FIGS. 1D and 1H). After 9 months dried EPT contained 91.8% pentamer and 8.2% monomer (* represents a line drop as the two peaks are not completely resolved). The resolution value of the two peaks is 1.6 (determined by OpenLab CDS 2.1 software, Agilent Technologies, Santa Clara, CA, USA).
Figure 1B:
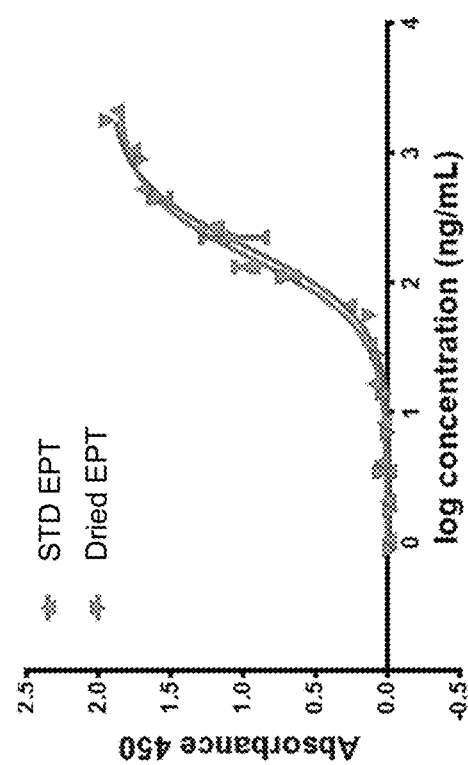
Figure 1C:
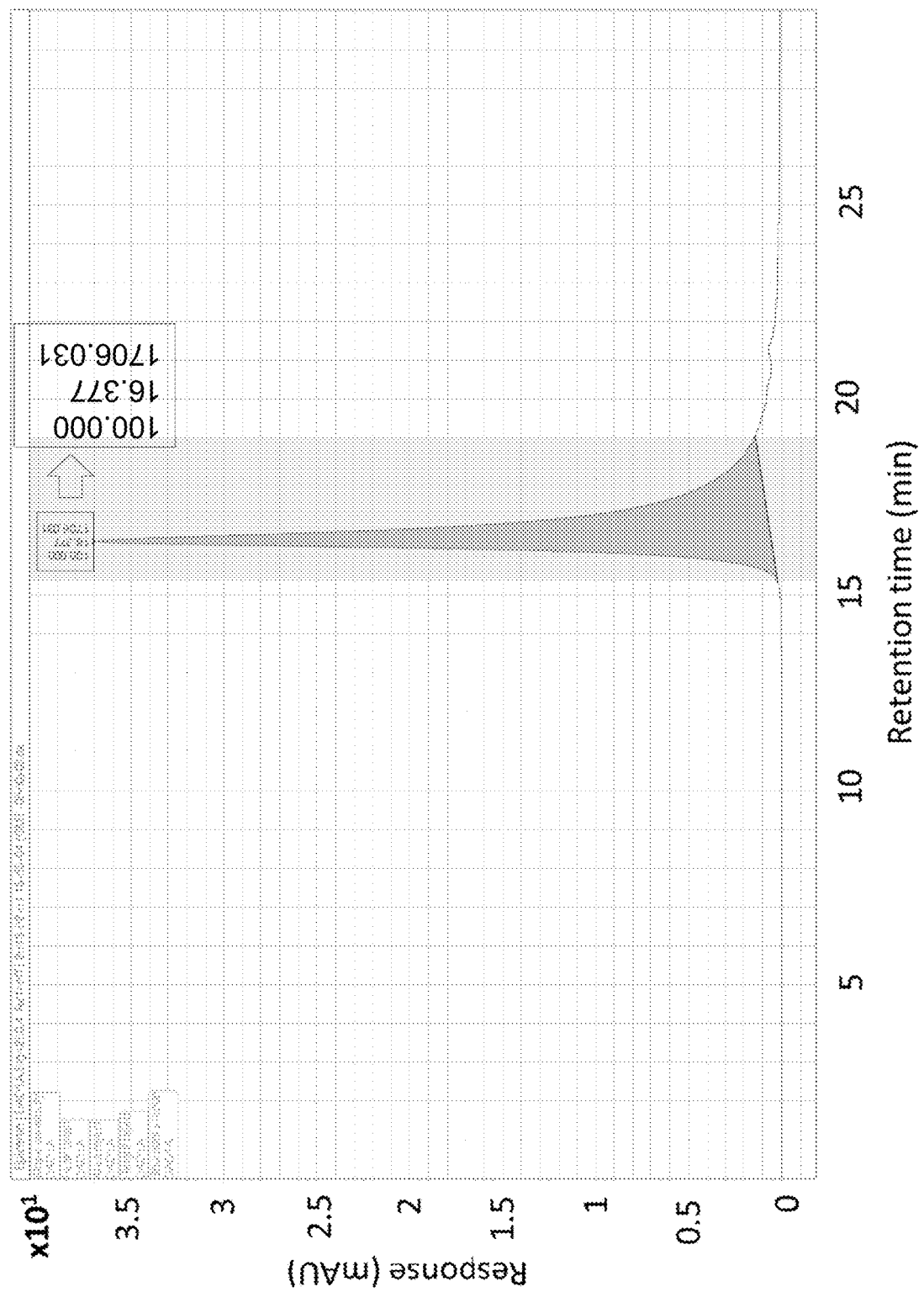
Figure 1D:
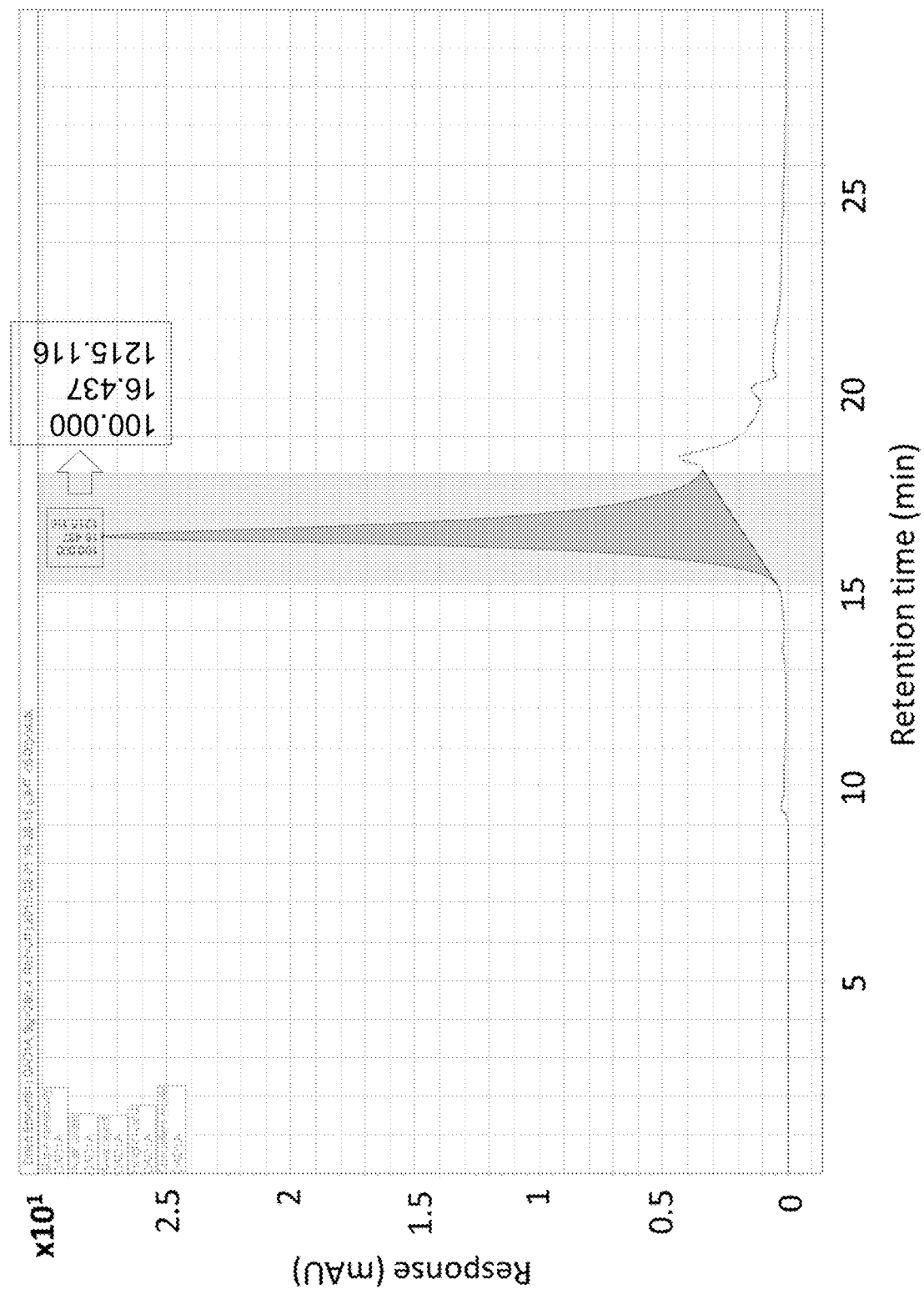
Figure 1E:
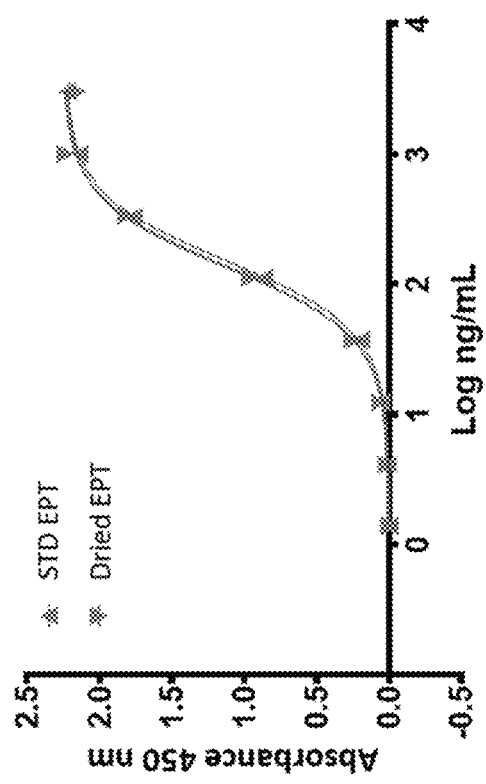
Figure 1F:
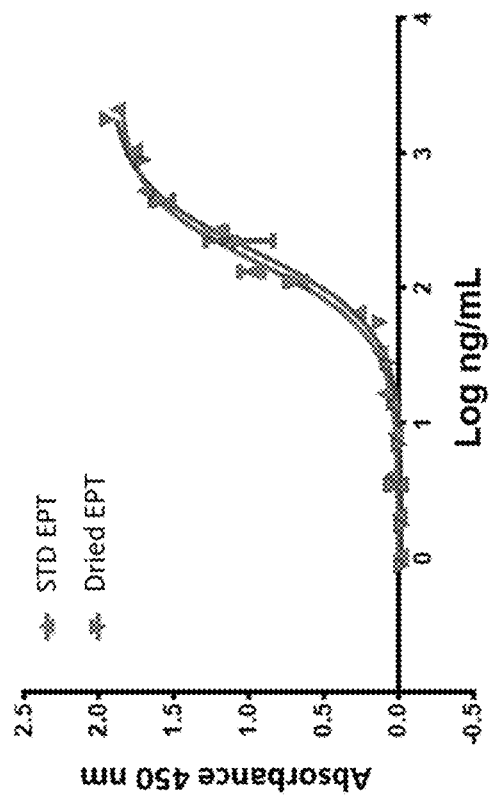
Figure 1G:
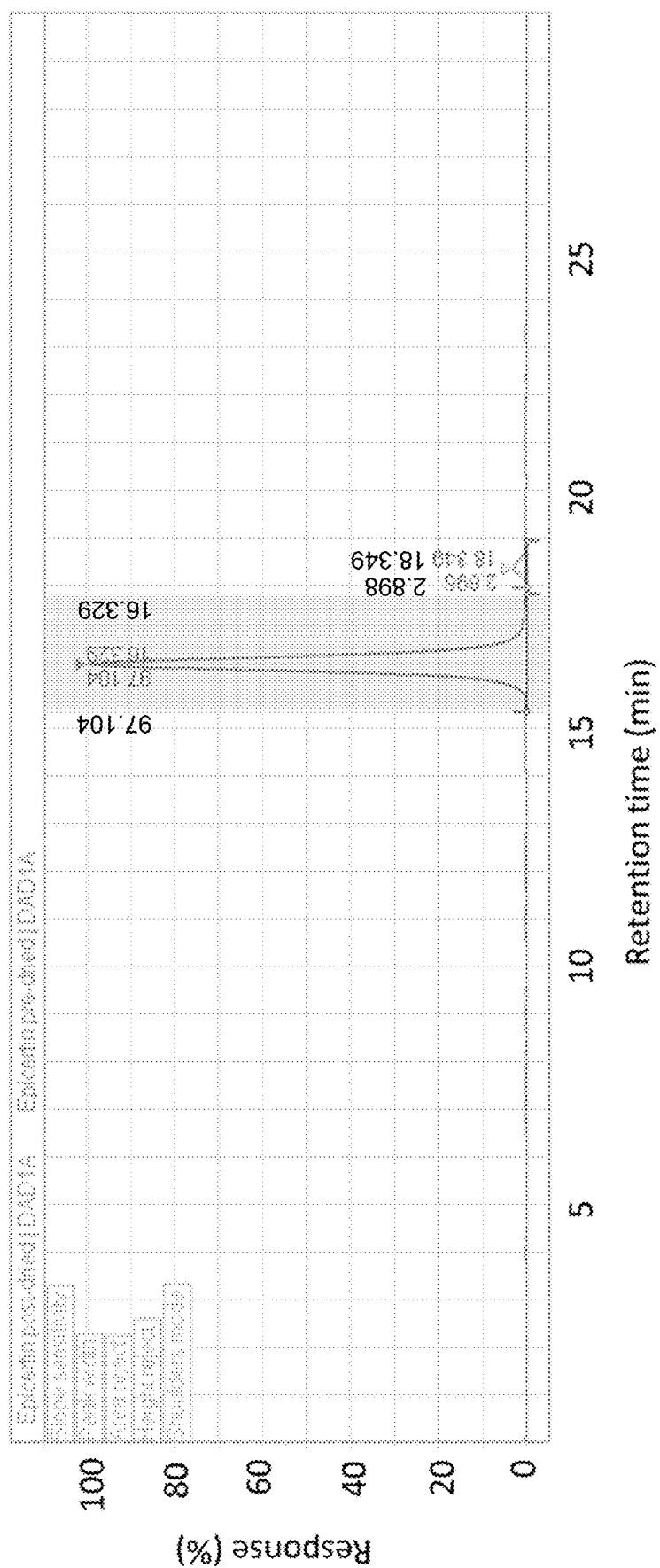
Figure 1H:
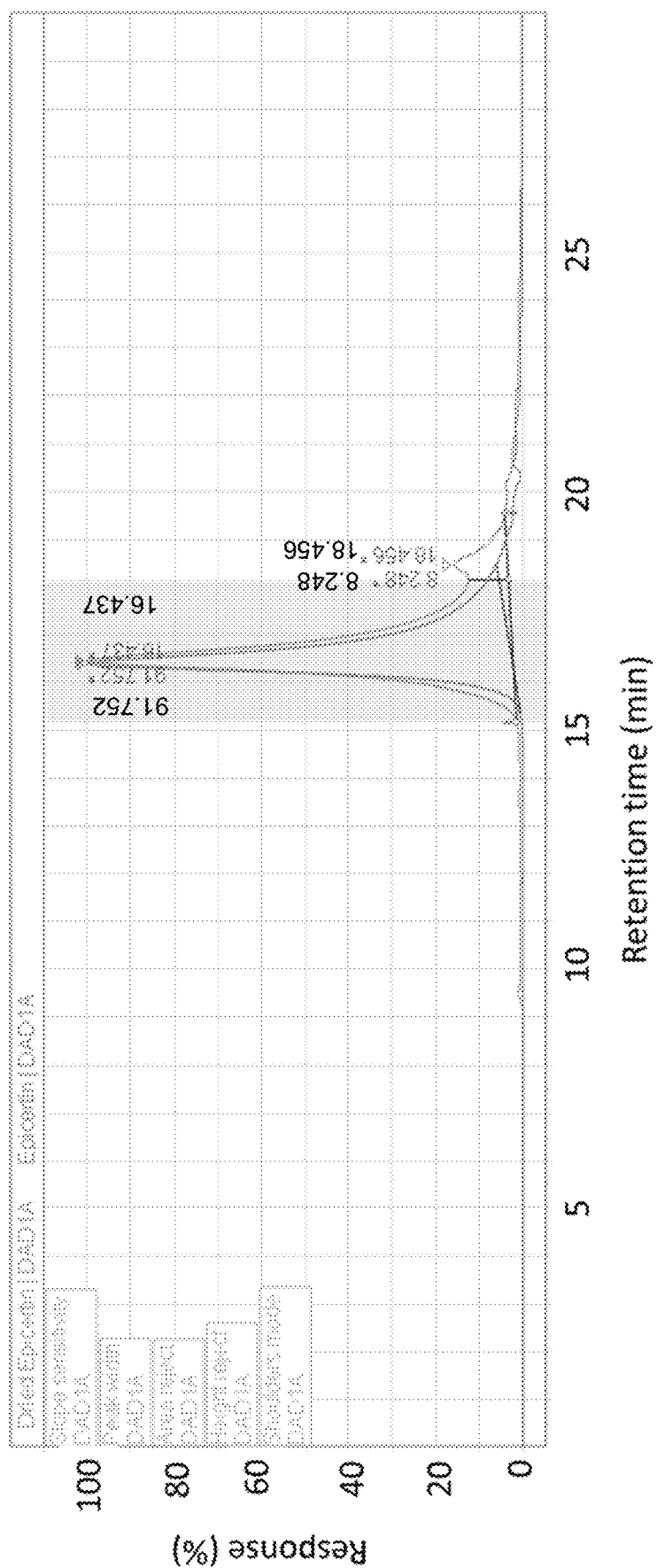

A description of example embodiments follows.

The subject matter disclosed herein is based, in part, on the discovery of Epicertin (EPT), a dry formulated plant made cholera toxin B subunit CTB$^{KDEL}$, as a novel, safe, effective and patient accepted treatment for mucosal inflammatory disorders including UC and mucositis.

Non-limiting benefits of dry-formulated Epicertin include improved patient adherence due to ease of administration and mitigate bad taste or smell; effortless formulation for targeted delivery; avoiding cold chain requirements; and improved product shelf life. Longer processing times, smaller dryer size, batch mode of production, and chill injury are considerable disadvantages of freezing drying process. In addition, the capital and operational costs of the spray drying process are ⅛ and ⅙, respectively, compared with those of freeze drying industrial technique.

Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly-used dictionaries, should be interpreted as having a meaning that is consistent with their meaning in the context of the relevant art and/or as otherwise defined herein.

The terminology used herein is for the purpose of describing particular embodiments only and is not intended to be limiting.

As would be recognized by those of ordinary skill in the art, cholera toxin is an oligomeric protein complex, which is secreted by the bacterium *Vibrio cholerae* and is thought to be responsible for the enteric symptoms characteristic of a cholera infection. The cholera toxin itself is generally composed of six protein subunits, namely a single copy of the A subunit, which is thought to be the toxic portion of the molecule responsible for its enzymatic action; and five copies of the B subunit, which form a pentameric ring and are thought to comprise the non-toxic portions of the molecule responsible for binding to receptors, such as the GM1 ganglioside receptor, which contains a glycosphingolipid (e.g., a ceramide and oligosaccharide) with one sialic acid and which is attached to the surface of a host cell. As such, the term "cholera toxin B subunit" is used herein to refer to a single B subunit of the cholera toxin as well as to B subunits of the cholera toxin in the form of multimers (e.g., in a pentameric form). Exemplary nucleic acid and amino acid sequence of a native cholera toxin B subunit polypeptide from wild-type *Vibrio cholerae* are provided herein in SEQ ID NOs:1 and 2 (see the section entitled "Sequences").

As used herein, the term "variant" refers to a polypeptide comprising an amino acid sequence that has at least about 70% sequence identity to a reference sequence, i.e., a wild type cholera toxin B subunit.

The term "polypeptide" "peptide" or "protein" denotes a polymer of at least two amino acids covalently linked by an amide bond, regardless of length or post-translational modification (e.g., glycosylation or phosphorylation). A protein, peptide or polypeptide can comprise any suitable L- and/or D-amino acid, for example, common α-amino acids (e.g., alanine, glycine, valine), non-α-amino acids (e.g., β-alanine, 4-aminobutyric acid, 6-aminocaproic acid, sarcosine, statine), and unusual amino acids (e.g., citrulline, homocitrulline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and methods for adding or removing protecting groups are known in the art and are disclosed in, for example, Green and Wuts, "*Protecting Groups in*

*Organic Synthesis*," John Wiley and Sons, 1991. The functional groups of a protein, peptide or polypeptide can also be derivatized (e.g., alkylated) or labeled (e.g., with a detectable label, such as a fluorogen or a hapten) using methods known in the art. A protein, peptide or polypeptide can comprise one or more modifications (e.g., amino acid linkers, acylation, acetylation, amidation, methylation, terminal modifiers (e.g., cyclizing modifications), N-methyl-α-amino group substitution), if desired. In addition, a protein, peptide or polypeptide can be an analog of a known and/or naturally-occurring peptide, for example, a peptide analog having conservative amino acid residue substitution(s).

As used herein, the term "sequence identity," refers to the extent to which two nucleotide sequences, or two amino acid sequences, have the same residues at the same positions when the sequences are aligned to achieve a maximal level of identity, expressed as a percentage. For sequence alignment and comparison, typically one sequence is designated as a reference sequence, to which a test sequences are compared. The sequence identity between reference and test sequences is expressed as the percentage of positions across the entire length of the reference sequence where the reference and test sequences share the same nucleotide or amino acid upon alignment of the reference and test sequences to achieve a maximal level of identity. As an example, two sequences are considered to have 70% sequence identity when, upon alignment to achieve a maximal level of identity, the test sequence has the same nucleotide or amino acid residue at 70% of the same positions over the entire length of the reference sequence.

Alignment of sequences for comparison to achieve maximal levels of identity can be readily performed by a person of ordinary skill in the art using an appropriate alignment method or algorithm. In some instances, the alignment can include introduced gaps to provide for the maximal level of identity. Examples include the local homology algorithm of Smith & Waterman, *Adv. Appl. Math.* 2:482 (1981), the homology alignment algorithm of Needleman & Wunsch, *J. Mol. Biol.* 48:443 (1970), the search for similarity method of Pearson & Lipman, *Proc. Nat'l. Acad. Sci. USA* 85:2444 (1988), computerized implementations of these algorithms (GAP, BESTFIT, FASTA, and TFASTA in the Wisconsin Genetics Software Package, Genetics Computer Group, 575 Science Dr., Madison, Wis.), and visual inspection (see generally Ausubel et al., *Current Protocols in Molecular Biology*).

When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters. A commonly used tool for determining percent sequence identity is Protein Basic Local Alignment Search Tool (BLASTP) available through National Center for Biotechnology Information, National Library of Medicine, of the United States National Institutes of Health. (Altschul et al., *Basic local alignment search tool. J Mot Biol.* 215(3):403-10 (1990)).

The term "conservative amino acid substitution(s)" or "conservative substitution(s)" refers to an amino acid substitution having a value of 0 or greater in BLOSUM62.

The term "highly conservative amino acid substitution(s)" or "highly conservative substitution(s)" refers to an amino acid substitution having a value of at least 1 (e.g., at least 2) in BLOSUM62.

As used herein, the term "pharmaceutically acceptable excipient" includes, e.g., suitable solvents, dispersion media, coatings, antibacterial agents and antifungal agents, isotonic agents, and absorption delaying agents. The use of such media and agents for pharmaceutically active substances is known in the art.

As used herein, the terms "treatment" or "treating" relate to any treatment of a disease of a subject, including, but not limited to, prophylactic treatment and therapeutic treatment. As such, the terms treatment or treating include, but are not limited to: preventing a disease or the development of a disease; inhibiting the progression of a disease; arresting or preventing the development of a disease; reducing the severity of a disease; ameliorating or relieving symptoms associated with a disease; and causing a regression of the disease or one or more of the symptoms associated with the disease.

The term "cancer" refers to all types of cancer or neoplasm or malignant tumors found in a subject, including leukemias, lymphomas, myelomas, carcinomas, melanomas, teratomas, and sarcomas. Examples of cancers include cancer of the liver, pancreas, esophagus, brain, bladder, breast, central nervous system (e.g., spine), cervix, colon, rectum, head and neck, kidney, lung, ovary, prostate, sarcoma, stomach, uterus, leukemias, lymphomas, myelomas, and melanomas.

The term "inflammatory disorder" includes diseases or disorders which are caused, at least in part, or exacerbated, by inflammation, which is generally characterized by increased blood flow, edema, activation of immune cells (e.g., proliferation, cytokine production, or enhanced phagocytosis), heat, redness, swelling, pain and/or loss of function in the affected tissue or organ. The cause of inflammation can be due to physical damage, chemical substances, microorganisms, tissue necrosis, cancer, or other agents or conditions.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they can last several weeks. Characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some inflammatory disorders fall within one or more categories.

Non-limiting examples of inflammatory disorders include atherosclerosis, arthritis, asthma, autoimmune uveitis, adoptive immune response, dermatitis, multiple sclerosis, diabetic complications, osteoporosis, Alzheimer's disease, cerebral malaria, hemorrhagic fever, autoimmune disorders, and inflammatory bowel disease. In some embodiments, the term "inflammatory disorder" is further inclusive of inflammation-promoted cancers, such that the term "inflammatory disorder" can be used to refer to cancers caused or promoted by inflammation, such as colon cancer.

The term "colitis" refers to an inflammation of the colon which may be acute or chronic.

The term "subject" refers to a mammal (e.g., human, dog, cat, horse, cow, mouse, rat). Preferably, the subject is a human (e.g., a human who has, or is at risk for developing cancer). A "subject in need thereof" refers to a subject who has, or is at risk for developing, cancer. A skilled medical professional (e.g., physician) can readily determine whether a subject (e.g., a patient) has, or is at risk for developing, cancer.

"A therapeutically effective amount" is an amount effective, at dosages and for periods of time necessary, to achieve a desired therapeutic result (e.g., treatment, healing, inhibition or amelioration of physiological response or condition, etc.). Example indicators of a "therapeutically effect amount" include, e.g., improved well-being of the patient, reduction of tumor burden, arrested or slowed growth of a tumor, or absence of metastasis of cancer cells, or a combination thereof.

"In combination with" means that two or more therapeutics can be administered to a subject together in a mixture or composition, concurrently as single agents, or sequentially as single agents in any order.

As used herein, the indefinite articles "a," "an" and "the" should be understood to include plural reference unless the context clearly indicates otherwise.

Throughout this specification and the claims which follow, unless the context requires otherwise, the word "comprise," and variations such as "comprises" and "comprising", will be understood to imply the inclusion of, e.g., a stated integer or step or group of integers or steps, but not the exclusion of any other integer or step or group of integer or step. When used herein, the term "comprising" can be substituted with the term "containing" or "including."

As used herein, "consisting of" excludes any element, step, or ingredient not specified in the claim element. When used herein, "consisting essentially of" does not exclude materials or steps that do not materially affect the basic and novel characteristics of the claim. Any of the terms "comprising," "containing," "including," and "having," whenever used herein in the context of an aspect or embodiment of the invention, can in some embodiments, be replaced with the term "consisting of," or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and, therefore, satisfy the requirement of the term "and/or" as used herein. Concurrent applicability of more than one of the options is also understood to fall within the meaning, and, therefore, satisfy the requirement of the term "and/or."

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Spray-Dried Powders

In one aspect, the disclosure provides a powder comprising a spray-dried formulation of a cholera toxin B subunit variant and a saccharide excipient.

Cholera Toxin B Subunit Variants

In some embodiments, the cholera toxin B subunit variant has at least about 80% sequence identity to a wild-type cholera toxin B subunit (e.g., SEQ ID NO:2), for example, having at least about: 85%, 90%, 91%, 92%, 93%, 94%, 95%, 96%, 97%, 98% or 99% sequence identity or having about: 80-99%, 85-99%, 90-99%, 91-99%, 92-99%, 93-99%, 94-99%, 95-99%, 96-99%, 97-99% or 98-99% sequence identity.

In particular embodiments, the cholera toxin B subunit variant comprises an endoplasmic reticulum (ER) retention sequence attached to its C-terminus. In some embodiments, the C-terminal ER retention sequence comprises SEKDEL (SEQ ID NO:30), KDEL (SEQ ID NO:31), SEHDEL (SEQ ID NO:32) or HDEL (SEQ ID NO:33).

In certain embodiments, the cholera toxin B subunit variant comprises an amino acid sequence that has at least about 80% sequence identity to at least one sequence set forth in SEQ ID NOs: 4, 6, 8, 10, 12, 14, 16, 25-29 and 34 (see the section entitled "Sequences"), for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:4, 6, 8, 10, 12, 14, 16, 25-29 and 34.

In particular embodiments, the cholera toxin B subunit variant comprises secretory signal peptide (e.g., a N-terminal secretory signal peptide). In some embodiments, the secretory signal peptide is a rice alpha-amylase secretory signal peptide, a *Nicotiana plumbagenifolia* calreticulin secretory signal peptide, an apple pectinase secretory signal peptide, or a barley alpha-amylase secretory signal peptide. In some embodiments, the secretory signal peptide sequence comprises SEQ ID NO:18, 20, 22 or 24.

In certain embodiments, the cholera toxin B subunit variant comprises an amino acid sequence that has at least about 80% sequence identity to at least one sequence set forth in SEQ ID NOs:16, 26-29 and 34, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:16, 26, 27, 28, 29 or 34.

In some embodiments, the cholera toxin B subunit variant comprises an amino acid sequence that has at least about 80% sequence identity to SEQ ID NO:4 and/or SEQ ID NO:34, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:4 or SEQ ID NO:34.

In some embodiments, the cholera toxin B subunit variant comprises an amino acid sequence that has at least about 80% sequence identity to SEQ ID NO:4, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:4.

In certain embodiments, the cholera toxin B subunit variant comprises an amino acid sequence that has at least about 80% sequence identity to SEQ ID NO:6, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:6.

In some embodiments, the cholera toxin B subunit variant comprises an amino acid sequence that has at least about 80% sequence identity to SEQ ID NO:8, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:8.

In certain embodiments, the cholera toxin B subunit variant comprises an amino acid sequence that has at least about 80% sequence identity to SEQ ID NO:10, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:10.

In some embodiments, the cholera toxin B subunit variant comprises an amino acid sequence that has at least about 80% sequence identity to SEQ ID NO:12, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:12.

In certain embodiments, the cholera toxin B subunit variant comprises an amino acid sequence that has at least about 80% sequence identity to SEQ ID NO:14, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:14.

In some embodiments, the cholera toxin B subunit variant comprises an amino acid sequence that has at least about 80% sequence identity to SEQ ID NO:16, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:16.

In certain embodiments, the cholera toxin B subunit variant comprises an amino acid sequence that has at least about 80% sequence identity to SEQ ID NO:25, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:25.

In some embodiments, the cholera toxin B subunit variant comprises an amino acid sequence that has at least about 80% sequence identity to SEQ ID NO:26, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:26.

In certain embodiments, the cholera toxin B subunit variant comprises an amino acid sequence that has at least about 80% sequence identity to SEQ ID NO:27, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:27.

In some embodiments, the cholera toxin B subunit variant comprises an amino acid sequence that has at least about 80% sequence identity to SEQ ID NO:28, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:28.

In certain embodiments, the cholera toxin B subunit variant comprises an amino acid sequence that has at least about 80% sequence identity to SEQ ID NO:29, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:29.

In some embodiments, the cholera toxin B subunit variant comprises an amino acid sequence that has at least about 80% sequence identity to SEQ ID NO:34, for example, having at least about: 85%, 90%, 91%, 92%, 93%, 94%, 95%, 96%, 97%, 98%, 99% or 100% sequence identity or having about: 80-100%, 85-100%, 90-100%, 91-100%, 92-100%, 93-100%, 94-100%, 95-100%, 96-100%, 97-100% or 98-100% sequence identity. In particular embodiments, the cholera toxin B subunit variant comprises an amino acid sequence set forth in SEQ ID NO:34.

In certain embodiments, the cholera toxin B subunit variant comprises at least one amino acid substitution, insertion, or deletion relative to a wild-type cholera toxin B subunit (e.g., SEQ ID NO:2). For example, the cholera toxin B subunit variant comprises at least: 2, 3, 4, 5, 6, 7, 8, 9, 10, 11, 12, 13, 14, 15, 16, 17, 18, 19 or 20 amino acid substitutions relative to a wild-type cholera toxin B subunit. In some embodiments, the cholera toxin B subunit variant comprises about: 1-20, 1-18, 2-18, 2-15, 3-15, 3-12, 4-12, 4-10, 5-10, 5-8 or 6-8 amino acid substitutions, relative to the reference sequence. In some embodiments, the amino acid substitutions include at least one conservative substitution. In certain embodiments, the amino acid substitutions include at least one highly conservative substitution.

In particular embodiments, the cholera toxin B subunit variant comprises an Asn4 to Ser mutation.

In some embodiments, the one or more modification (amino acid substitution, insertion, and/or deletion) facilitates recombinant production of the cholera toxin B subunit variant. In certain embodiments, the cholera toxin B subunit variant has an increased level of expression in a plant cell than the corresponding wild-type cholera toxin B subunit. In particular embodiments, the cholera toxin B subunit variant is substantially immunologically identical to a wild-type cholera toxin B subunit.

In some embodiments, the powder comprises one cholera toxin B subunit variant. In other embodiments, the powder comprises two or more cholera toxin B subunit variants, for example, 2, 3, 4, 5 or more cholera toxin B subunit variants.

Saccharide Excipients

Non-limiting examples of saccharide excipients suitable for use in the disclosure include monosaccharides, disaccharides, polysaccharides and alditols.

In some embodiments, the saccharide excipient comprises an alditol. Non-limiting examples of alditols include lactitol, maltitol, mannitol, myoinositol, pyranosyl sorbitol, xylitol, xylitol sorbitol (glucitol), and combinations thereof. In particular embodiments, the saccharide excipient comprises mannitol.

In certain embodiments, the saccharide excipient comprises a monosaccharide. Non-limiting examples of monosaccharides include dextrose, fructose, maltose, galactose, glucose, D-mannose, sorbose, and combinations thereof. In particular embodiments, the saccharide excipient comprises dextrose.

In some embodiments, the saccharide excipient comprises a disaccharide. Non-limiting examples of disaccharides include lactose, sucrose, trehalose, cellobiose, and combinations thereof. In particular embodiments, the saccharide excipient comprises lactose, trehalose, or both.

In certain embodiments, the saccharide excipient comprises a polysaccharide. Non-limiting examples of polysaccharides include raffinose, melezitose, maltodextrins, dextrans, starches, and combinations thereof.

In some embodiments, the saccharide excipient is thermoprotective. In certain embodiments, the saccharide excipient comprises mannitol, dextrose, trehalose, lactose, or a combination thereof. In some embodiments, the saccharide excipient comprises mannitol, lactose, or both.

In some embodiments, the saccharide excipient is inert (e.g., has a relatively low hygroscopicity, is relatively less likely to react with active pharmaceutical ingredients, or both).

In some embodiments, the powder comprises one saccharide excipient. In other embodiments, the powder comprises two or more saccharide excipients, for example, 2, 3, 4, 5 or more saccharide excipients.

Pharmaceutical Compositions

In some embodiments, a powder of the disclosure is formulated into a pharmaceutical composition suitable for administration (e.g., for oral administration) to a subject such as a mammal, e.g., a human patient.

In another aspect, the disclosure provides a pharmaceutical composition for oral administration, comprising a cholera toxin B subunit variant and a saccharide excipient, wherein the pharmaceutical composition is spray-dried.

The cholera toxin B subunit variant can be any one or more of the cholera toxin B subunit variants described herein. In some embodiments, the cholera toxin B subunit variant comprises an amino acid sequence that has at least about 80% sequence identity to SEQ ID NO:4 and/or SEQ ID NO:34. In certain embodiments, the cholera toxin B subunit variant comprises an amino acid sequence set forth in SEQ ID NO:4 or SEQ ID NO:34.

The saccharide excipient can be any one or more of the saccharide excipients described herein. In particular embodiments, the saccharide excipient comprises mannitol.

In certain embodiments, the pharmaceutical composition further comprises one or more pharmaceutically acceptable excipients.

A pharmaceutical composition of the disclosure can be formulated to be compatible with its intended route of administration. For example, oral compositions can include an inert diluent or an edible carrier. They can be enclosed in gelatin capsules or compressed into tablets. The pharmaceutical composition can be in the form of tablets, troches, or capsules. In certain embodiments, the pharmaceutical composition is in the form of a capsule.

In some embodiments, the pharmaceutical composition (e.g., capsule) is enteric-coated.

In certain embodiments, the capsule (e.g., the cap, the body joints, or both) comprises a polymer that degrades at a desired pH. In some embodiments, the desired pH is between about pH 6.7 and about pH 6.9, for example, about pH 6.7, pH 6.8 or pH 6.9. In some embodiments, the capsule comprises a polymer that degrades at about pH 6.8. In particular embodiments, the capsule comprises Eudragit® L100 anionic polymer.

In particular embodiments, the pharmaceutical composition is encapsulated at about pH 1 and gradually released at about pH 6.8.

In certain embodiments, the pharmaceutical composition:
a) comprises no more than about 25% monomer;
b) comprises no more than about 10% moisture; or
c) exhibits about 100±20% solubility, or
a combination thereof.

In some embodiments, the pharmaceutical composition comprises no more than about 25% monomer, for example, no more than about: 20%, 18%, 15%, 12%, 10%, 9%, 8%, 7%, 6%, 5%, 4%, 3.5%, 3%, 2%, 1.5% or 1% monomer. In certain embodiments, the pharmaceutical composition comprises no more than about 10% monomer. In certain embodiments, the pharmaceutical composition comprises less than about 5% monomer. In some embodiments, the pharmaceutical composition comprises less than about 3.5% monomer. In particular embodiments, the pharmaceutical composition comprises less than about 1.5% monomer.

In certain embodiments, the pharmaceutical composition comprises about 1-20% monomer, for example, about: 1-18%, 1-15%, 1-12%, 1-10%, 1-9%, 1-8%, 1-7%, 1-6%, 1-5%, 1-4%, 1-3%, 1-2%, 2-20%, 2-18%, 2-15%, 2-12%, 2-10%, 2-9%, 2-8%, 2-7%, 2-6%, 2- 5%, 2-4%, 2-3%, 3-20%, 3-18%, 3-15%, 3-12%, 3-10%, 3-9%, 3-8%, 3-7%, 3-6%, 3-5%, 3-4%, 4-20%, 4-18%, 4-15%, 4-12%, 4-10%, 4-9%, 4-8%, 4-7%, 4-6% or 4-5% monomer. In particular embodiments, the pharmaceutical composition comprises about 1-3.5% monomer.

In certain embodiments, the pharmaceutical composition comprises no more than about 10% moisture, for example, no more than about: 9%, 8%, 7%, 6%, 5%, 4%, 4%, 2% or 1% moisture. In particular embodiments, the pharmaceutical composition comprises about 1-10% moisture, for example, about: 1-9%, 1-8%, 1-7%, 1-6%, 1-5%, 1-4%, 1-3%, 1-2%, 2-10%, 2-9%, 2-8%, 2-7%, 2-6%, 2-5%, 2-4%, 2-3%, 3-10%, 3-9%, 3-8%, 3-7%, 3-6%, 3-5%, 3-4%, 4-10%, 4-9%, 4-8%, 4-7%, 4-6%, 4-5%, 5-10%, 5-9%, 5-8%, 5-7%, 5-6%, 6-10%, 6-9%, 6-8% or 6-7% moisture.

In some embodiments, the pharmaceutical composition exhibits about 100±20% solubility, for example, about: 100±18%, 100±15%, 100±12%, 100±10%, 100±9%, 100±8%, 100±7%, 100±6% or 100±5% solubility. In particular embodiments, the pharmaceutical composition exhibits about 100±10% solubility.

In certain embodiments, the pharmaceutical composition:
a) comprises no more than about 5% monomer;
b) comprises no more than about 10% moisture; or
c) exhibits about 100±10% solubility, or
a combination thereof.

In some embodiments, less than about 10%, for example, less than about: 9%, 8%, 7%, 6%, 5%, 4%, 3%, 2% or 1% or about: 1-10%, 1-5%, 1-3%, 3-10%, 3-5% or 5-10%, of the cholera toxin B subunit variant pentamer in the pharmaceutical composition degrades after a 9-month post-drying storage at about 22-24° C. In certain embodiments, less than about 5% of the cholera toxin B subunit variant pentamer in the pharmaceutical composition degrades after a 9-month post-drying storage at about 23° C. In particular embodiments, less than about 3% of the cholera toxin B subunit variant pentamer in the pharmaceutical composition degrades after a 9-month post-drying storage at about 23° C.

Methods of Treatment

In another aspect, the disclosure provides a method of treating a disease, the method comprises administering to a subject in need thereof an effective amount of a pharmaceutical composition comprising a cholera toxin B subunit variant and a saccharide excipient, wherein the pharmaceutical composition is spray-dried.

In another aspect, the disclosure provides a method of enhancing wound healing, the method comprises administering to a subject in need thereof an effective amount of a pharmaceutical composition comprising a cholera toxin B subunit variant and a saccharide excipient, wherein the pharmaceutical composition is spray-dried.

The cholera toxin B subunit variant can be any one or more of the cholera toxin B subunit variants described herein. In some embodiments, the cholera toxin B subunit variant comprises an amino acid sequence that has at least about 80% sequence identity to SEQ ID NO:4 and/or SEQ ID NO:34. In certain embodiments, the cholera toxin B subunit variant comprises an amino acid sequence set forth in SEQ ID NO:4 or SEQ ID NO:34.

The saccharide excipient can be any one or more of the saccharide excipients described herein. In particular embodiments, the saccharide excipient comprises mannitol.

In some embodiments, the disease is cancer. In certain embodiments, the cancer is colon cancer. In particular embodiments, the colon cancer is colitis-associated colon cancer.

In some embodiments, the disease is an inflammatory disorder. In particular embodiments, the inflammatory disorder is sepsis, septic shock, colitis, colon cancer or arthritis. In certain embodiments, the inflammatory disorder is an inflammatory bowel disease, a gastrointestinal inflammation and/or injury, a mucosal inflammation, or a combination thereof.

In some embodiments, the inflammatory bowel disease comprises ulcerative colitis, Crohn's disease, or both. In certain embodiments, the inflammatory bowel disease comprises Crohn's disease. In particular embodiments, the inflammatory bowel disease comprises ulcerative colitis. In some embodiments, the inflammatory bowel disease comprises ulcerative colitis and Crohn's disease.

Non-limiting examples of gastrointestinal inflammations and/or injuries include celiac disease, irritable bowel syndrome, radiation-induced colitis, infection-induced colitis, and combinations thereof.

Non-limiting examples of mucosal inflammations and/or injuries include asthma, airway burns, corneal injury, vaginosis, and combinations thereof.

In some embodiments, the disease is a mucosal inflammatory disorder. In certain embodiments, the disease comprises ulcerative colitis, mucositis or both. In some embodiments, the disease comprises ulcerative colitis and mucositis. In particular embodiments, the disease comprises mucositis.

In particular embodiments, the pharmaceutical composition is administered in combination with one or more additional therapeutics. In some embodiments, the pharmaceutical composition and the one or more additional therapeutics are administered together. In other embodiments, the pharmaceutical composition and the one or more additional therapeutics are administered separately.

Methods of Making

In another aspect, the disclosure provides a method of producing an oral formulation of a cholera toxin B subunit variant, comprising:

a) mixing a phosphate-buffered saline solution of the cholera toxin B subunit variant with a saccharide excipient; and b) spray drying the solution in an air stream.

The cholera toxin B subunit variant can be any one or more of the cholera toxin B subunit variants described herein. In some embodiments, the cholera toxin B subunit variant comprises an amino acid sequence that has at least about 80% sequence identity to SEQ ID NO:4 and/or SEQ ID NO:34. In certain embodiments, the cholera toxin B subunit variant comprises an amino acid sequence set forth in SEQ ID NO:4 or SEQ ID NO:34.

The saccharide excipient can be any one or more of the saccharide excipients described herein. In some embodiments, the saccharide excipient comprises mannitol. In certain embodiments, the method comprises mixing a phosphate-buffered saline solution of the cholera toxin B subunit variant (e.g., at about 1 mg/mL) with about 100 mM mannitol. In particular embodiments, the method comprises mixing a phosphate-buffered saline solution of the cholera toxin B subunit variant (e.g., at about 1 mg/mL) with about 100 mM mannitol at about pH 7.2.

In some embodiments, spray drying the solution uses:
a) an inlet air temperature of about 116-122° C.;
b) an outlet air temperature of about 64-78° C.; or
c) an inlet to outlet air temperature ratio of about 1.7-2.1,
or
a combination thereof.

In particular embodiments, spray drying the solution uses:
a) an inlet air temperature of about 116-122° C.;
b) an outlet air temperature of about 64-67° C.; or
c) an inlet to outlet air temperature ratio of about 1.7-2.1,
or
a combination thereof.

In certain embodiments, spray drying the solution uses an inlet air temperature of about 116-122° C., for example, an inlet air temperature of about: 116° C., 117° C., 118° C., 119° C., 120° C., 121° C. or 122° C.

In particular embodiments, spray drying the solution uses an outlet air temperature of about 64-78° C., for example, an outlet air temperature of about: 64° C., 65° C., 66° C., 67° C., 68° C., 69° C., 70° C., 71° C., 72° C., 73° C., 74° C., 75° C., 76° C., 77° C. or 78° C., or an outlet air temperature of about: 64-78° C., 64-77° C., 64-76° C., 64-75° C., 64-74° C., 64-73° C., 64-72° C., 64-71° C., 64-70° C., 64-69° C., 64-68° C. or 64-67° C. In some embodiments, spray drying the solution uses an inlet air temperature of about 64-67° C.

In certain embodiments, spray drying the solution uses an inlet to outlet air temperature ratio of about 1.7-2.1, for example, an inlet to outlet air temperature ratio of about: 1.7, 1.8, 1.9, 2.0 or 2.1 or an inlet to outlet air temperature ratio of about: 1.7-2.0, 1.7-1.9, 1.7-1.8, 1.8-2.1, 1.8-2.0, 1.8-1.9, 1.9-2.1, 1.9-2.0 or 2.0-2.1.

In some embodiments, the Q-flow (drying gas flow rate) is about 34 or 35 g/min. In certain embodiments, the Q-flow is about 34 g/min. In particular embodiments, the Q-flow is about 35 g/min.

In certain embodiments, spray drying the solution uses an aspirator setting of about 80 to 95, for example, about: 80, 85, 90 or 95, or about 80-90, 80-85, 85-95, 85-90 or 90-95.

In certain embodiments, spray drying the solution uses a pump setting of about 20-30, for example, about: 20, 21, 22, 23, 24, 25, 26, 27, 28, 29 or 30, or about 20-28, 20-25, 20-22, 22-30, 22-28, 22-25, 25-30, 25-28 or 28-30.

Liquid Compositions

In another aspect, the disclosure provides a liquid composition, wherein the liquid composition comprises a cholera toxin B subunit variant and mannitol.

The cholera toxin B subunit variant can be any one or more of the cholera toxin B subunit variants described herein. In some embodiments, the cholera toxin B subunit variant comprises an amino acid sequence that has at least about 80% sequence identity to SEQ ID NO:4 and/or SEQ ID NO:34. In certain embodiments, the cholera toxin B subunit variant comprises an amino acid sequence set forth in SEQ ID NO:4 or SEQ ID NO:34.

In some embodiments, the liquid composition comprises about 100 mM mannitol. In certain embodiments, the liquid composition further comprises phosphate buffered saline (PBS).

In certain embodiments, the liquid composition comprises about 2.7 mM KCl, about 1.5 mM $KH_2PO_4$, about 136.9 mM NaCl, about 8.9 mM $Na_2HPO4 \cdot 7H_2O$, about 100 mM mannitol, or a combination thereof. In particular embodiments, the liquid composition comprises about 2.7 mM KCl, about 1.5 mM $KH_2PO_4$, about 136.9 mM NaCl, about 8.9 mM $Na_2HPO4 \cdot 7H_2O$ and about 100 mM mannitol.

EXAMPLES

Mucosal healing is a major treatment goal for UC patients [11,12,14,15]. It is a complex and dynamic process involving multiple cell types including epithelial, stromal and immune cells [14]. Epithelial repair plays a crucial role in mucosal healing by rebuilding the intestinal barrier to inhibit inflammation caused by entry of bacteria into the mucosa. Since inflammation in UC is limited to the innermost layer of the colon and rectal mucosa, epithelial repair may be key to achieving mucosal healing in this subset of IBD patients [5,11]. Thus, an epithelial repair agent may fill a current treatment gap for UC. We previously found that oral administration of a plant-made recombinant variant of cholera toxin B subunit (CTB) facilitates epithelial repair and mucosal healing in dextran sulfate sodium (DSS)-induced acute and chronic colitis mouse models [15,16]. CTB is the nontoxic homopentameric component of the cholera toxin with high binding affinity to GM1 ganglioside on epithelial cells [17]. This variant, $CTB^{KDEL}$, henceforth designated Epicertin (EPT), has a major modification from the parent molecule; the C-terminal hexapeptide extension containing a KDEL endoplasmic reticulum (ER) retention motif [18, 19]. While the alteration did not affect the GM1-binding affinity, molecular stability or oral immunogenicity of the original molecule [18], EPT, but not wild-type CTB, induced mucosal healing in the DSS colitis model. This unique new activity, which stems from EPT's capacity to interact with the KDEL receptor and subsequently activate the inositol-requiring enzyme 1/X-box binding protein 1 arm of an unfolded protein response in colon epithelial cells [20], lends support for the development of EPT as a new class of oral therapeutics for UC.

EPT may be administered to the colon topically or by oral gavage to alleviate DSS induced colitis in mice [20]. Although oral medications are generally preferred by patients and increase patient adherence to treatment regimens [3,21,22], oral administration of EPT solution requires neutralization of stomach acid to prevent degradation of the protein. This is similar to the World Health Organization prequalified oral cholera vaccine, Dukoral™, which is administered in a solution following stomach neutralization with a sodium bicarbonate solution. Considering potential long-term treatment necessary for the management of UC

[21], this neutralization step could be disadvantageous as it would likely lower patient adherence and ease of administration. To address this limitation, we describe here the development of a prototype enteric-coated oral formulation of EPT that allows for pH-dependent release of the drug substance in the colon, wherein the protein was spray dried and encapsulated in a gelatin capsule coated with an anionic polymer. Our results provide a foundation for further development of a novel oral biologic to facilitate colon mucosal healing in UC.

Example 1

Materials and Methods

Animals

Eight-week-old C57BL/6J, female mice were obtained from Jackson Laboratories (Bar Harbor, ME). The University of Louisville's Institutional Animal Care and Use Committee approved all animal studies conducted herein.

EPT Production

EPT was produced in *Nicotiana benthamiana* using a transient overexpression system and purified to >95% homogeneity with an endotoxin level of <3 endotoxin units per mg as described previously [19,22,23]. EPT was ultra-filtrated/diafiltrated into various buffers (Tables 1A-1B) using 30,000 MWCO centrifugal devices. Phosphate buffered saline (PBS) with 100 mM mannitol was found to be the optimal buffer for spray drying of EPT. EPT at 1 mg/mL in PBS with 100 mM mannitol excipient (pH 7.2) was dehydrated using a Büchi B-290 mini spray drier with an inlet temperature of 125° C. and an outlet temperature maintained between 65° C. and 67° C. The Q-Flow was 35 mm, aspirator was 90% and pump 20%. EPT powder was stored in conical tubes wrapped in parafilm under desiccation at room temperature (20-25° C.) until use. Standard EPT used for the GM1/KDEL ELISA and SEC-HPLC was produced in *Nicotiana benthamiana* using a transient overexpression system and purified to >95% homogeneity with an endotoxin level of <3 endotoxin units per mg as described previously [19,22,23].

TABLE 1A

Determination of optimal buffer excipient for $CTB^{KDEL}$ (EPT) powder production.

| Buffer | % Monomer | % Moisture | % Loss | % Solubility |
|---|---|---|---|---|
| PBS | 4.9 | 2.9 | 29.3 | 106 |
| PBS, 20 mM Mannitol | 4.5 | 10.3 | 56.6 | 94 |
| PBS, 100 mM Mannitol | 3.1 | 0 | 60.4 | 97 |
| PBS, 250 mM Mannitol | 9.1 | 7.5 | 80.4 | 99 |
| PBS, 250 mM Mannitol | 6.4 | 4.1 | 68.1 | 87 |
| 30 mM Phosphate, pH 7 | 3.2 | 31.5 | 38.5 | 67 |
| 30 mM Phosphate, 20 mM Mannitol, pH 7 | 1.1 | 14.7 | 79.5 | 81 |
| 30 mM Phosphate, 250 mM Mannitol, pH 7 | 5.8 | 2.3 | 28.9 | 97 |
| 30 mM Phosphate, 250 mM Mannitol, pH 7 | 5.8 | 3.9 | 43.5 | 96 |
| 30 mM Phosphate, 250 mM Mannitol, pH 7 | 6.7 | 5.4 | 33.2 | 91 |
| 30 mM Phosphate, pH 7.5 | 6.1 | 20 | 73.1 | 79 |
| 30 mM Phosphate, 20 mM Mannitol, pH 7.5 | 2.4 | 21.3 | 63.6 | 82 |
| 30 mM Phosphate, 250 mM Mannitol, pH 7.5 | 5.2 | 1 | 28.5 | 88 |
| 30 mM Phosphate, 250 mM Mannitol, pH 7.5 | 7.0 | 2.1 | 34.4 | 92 |
| 30 mM Phosphate, 250 mM Mannitol, pH 7.5 | 7.3 | 3.1 | 50.2 | 64 |
| 88 mM Phosphate, 20 mM Mannitol, pH 7 | 2.1 | 18.4 | 43.7 | 96 |
| TARGET | <5% | <10% | <40% | 100 ± 10 |

TABLE 1B

Determination of optimal buffer excipient for $CTB^{KDEL}$ (EPT) powder production.

| Buffer | % Monomer | % Moisture | % Loss | % Solubility |
|---|---|---|---|---|
| PBS | 12.3 | 9.7 | 36.2 | 97 |
| PBS | 5.9 | 4.5 | 34.5 | 101 |
| PBS | 3.2 | 32.3 | 29.3 | 101 |
| PBS | 8.0 | 3.7 | 36.2 | 99 |
| PBS | 4.9 | 2.9 | 29.3 | 106 |
| PBS, 20 mM Mannitol | 4.5 | 10.3 | 56.6 | 94 |
| PBS, 100 mM Mannitol | 4.4 | 3.9 | 60.4 | 101 |
| PBS, 100 mM Mannitol | 3.1 | 0 | 60.4 | 97 |
| PBS, 250 mM Mannitol | 9.1 | 7.5 | 80.4 | 99 |
| PBS, 250 mM Mannitol | 6.4 | 4.1 | 68.1 | 87 |
| 30 mM Phosphate, pH 7 | 3.2 | 31.5 | 38.5 | 67 |
| 30 mM Phosphate, 20 mM Mannitol, pH 7 | 1.1 | 14.7 | 79.5 | 81 |
| 30 mM Phosphate, 250 mM Mannitol, pH 7 | 5.8 | 2.3 | 28.9 | 97 |
| 30 mM Phosphate, 250 mM Mannitol, pH 7 | 5.8 | 3.9 | 43.5 | 96 |
| 30 mM Phosphate, 250 mM Mannitol, pH 7 | 6.7 | 5.4 | 33.2 | 91 |
| 30 mM Phosphate, pH 7.5 | 6.1 | 20 | 73.1 | 79 |
| 30 mM Phosphate, 20 mM Mannitol, pH 7.5 | 2.4 | 21.3 | 63.6 | 82 |
| 30 mM Phosphate, 250 mM Mannitol, pH 7.5 | 5.2 | 1 | 28.5 | 88 |
| 30 mM Phosphate, 250 mM Mannitol, pH 7.5 | 7.0 | 2.1 | 34.4 | 92 |
| 30 mM Phosphate, 250 mM Mannitol, pH 7.5 | 7.3 | 3.1 | 50.2 | 64 |

TABLE 1B-continued

Determination of optimal buffer excipient for CTB$^{KDEL}$ (EPT) powder production.

| Buffer | % Monomer | % Moisture | % Loss | % Solubility |
|---|---|---|---|---|
| CHT, 42.5% B (diafiltrated) | 1.0 | 4.2 | 56.3 | 141 |
| CHT, 42.5% B (diafiltrated) | 5.0 | 10.7 | 48.5 | 149 |
| CHT, 42.5% B (diafiltrated) | 3.0 | 6.6 | 41.1 | 121 |
| CHT, 42.5% B (diafiltrated) + 100 Mannitol | 2.0 | 4.6 | 44.4 | 119 |
| CHT, 40% B (eluted) | 2.6 | 2.8 | 45 | 143 |
| CHT, 40% B (eluted) | 3.0 | 6.7 | 41.9 | 139 |
| CHT, 47.5% B (eluted) | 2.6 | 15.6 | 48.8 | 132 |
| CHT, 47.5% B (eluted) | 2.6 | 11.7 | 53.1 | 132 |
| CHT, 33% B (diafiltrated) | 5.0 | 23.1 | 43.9 | 140 |
| CHT, 47.5% B (diafiltrated) | 3.1 | 12.7 | 47 | 132 |
| 88 mM Phosphate, 20 mM Mannitol, pH 7 | 2.1 | 18.4 | 43.7 | 96 |
|  | <5% | <10% | <40% | 100 ± 10 |

EPT Powder Characterization

To measure residual moisture, a 5.9-mg portion of dried powder was incubated at 70° C. for 16 h, and the weight difference before and after heating was used to calculate moisture content. To determine solubility, dried powder was weighed and a calculated volume of milli Q water was added to reconstitute EPT powder to 1 mg/mL. The concentration of the reconstitute solution was measured by Nanodrop (Thermo Fisher Scientific; Waltham, MA, USA) using an extinction coefficient at A280 of 0.7857. The percent solubility was calculated based on the difference in 1 mg/mL versus the determined nanodrop concentration.

Percent monomer was determined by size-exclusion high performance liquid chromatography (SEC-HPLC). SEC-HPLC was run as previously described [17]. Briefly, reconstituted EPT at 1 mg/mL was applied to a Tosoh TSKgel SuperSW3000 column using 100 mM sodium phosphate, pH 7.2, 150 mM sodium chloride running buffer. EPT standard (a bulk solution prepared in PBS before spray drying) was used as a control.

GM1-Capture KDEL-Detection (GM1/KDEL)-ELISA

The assay was done as described in Morris et al. [24]. Plates were coated with 100 per well of 2 µg/mL GM1 ganglioside (Sigma Aldrich; St. Louis, MO, USA) diluted in a coating solution consisting of 3 mM sodium azide, 15 mM sodium carbonate, 35 mM sodium bicarbonate, pH 9.6. After overnight incubation (16 to 18 h) at 4° C., plates were washed three times with PBST (0.05% Tween 20 in 1×PBS) and blocked with a blocking solution (5% non-fat dry milk, 0.05% Tween 20 in 1×PBS) for 1 h at room temperature, then washed with PBST thrice. Three-fold serially diluted, duplicate samples (100 µL/well) were added to plates in 1% PBSTM (1% dry milk, 0.05% Tween 20 in 1×PBS). Samples were incubated on plates for 1 h at 37° C. Plates were washed and mouse anti-KDEL monoclonal antibody (Enzo Life Sciences; Farmingdale, NY, USA) diluted 1:1,000 in 1% PBSTM (100 µL/well) was added; plates were then incubated at 37° C. for 1 h. Plates were washed and goat anti-mouse IgG-HRP (Southern Biotech; Birmingham, AL, USA) diluted 1:5,000 in 1% PBSTM was added, followed by incubation at 37° C. for 1 h. Plates were washed a final time and developed with 3,3',5,5'-tetramethylbenzidine substrate (TMB). The reaction was stopped with 2 N sulfuric acid and the absorbance at 450 nm was immediately measured with a BioTek plate reader.

EPT Capsule Package and Preparation

Torpac size M gelatin capsules were packed with 2.3-2.8 mg dried EPT product per capsule (corresponding to 5±1 μg of EPT) using the ProFunnel capsule filling system (Torpac; Fairfield, NJ, USA). Capsule cap and body joints were painted with 4% Eudragit L100 anionic polymer coating solution and allowed to dry for 20 min. Capsules were loaded into a size M capsule holder and dipped just past the cap and body joints into 4% Eudragit L100 coating solution (recipe recommended by Torpac) and allowed to dry for 25 min according to the capsule manufacturer instructions. Capsules were flipped and reloaded into the holder and dipped past the cap and body joints into 4% Eudragit L100 coating solution. Dipping of capsules was repeated with 20% Eudragit L100 coating solution. Eudragit L100 was the chosen polymer due to its degradation at pH 6.8, the approximate pH of the proximal colon.

Capsule Disintegration Test

Individual EPT-containing enteric-coated capsules (n=5) were submerged in 1 N hydrochloric acid for 2 h at room temperature. Acid submerging each capsule was removed and stored separately. Capsules were washed briefly with sodium phosphate buffer (pH 6.0) followed by submersion in sodium phosphate buffer (pH 6.8). Aliquots were removed from each tube following light vortexing at 5, 10, 15, 30, 60, 90, 120, and 180 min and stored individually. EPT release from individual capsules was analyzed by CTB sandwich ELISA.

CTB Sandwich ELISA

The concentration of EPT standard was measured by Nanodrop (Thermo Fisher Scientific; Waltham, MA, USA). Plates were coated with 100 μL per well of 2.5 μg/mL of the rat anti-CTB monoclonal antibody 7A12B3 diluted in PBS. After overnight incubation (16 to 24 h) at 4° C., plates were washed three times with PBST (0.05% Tween 20 in 1×PBS) and blocked with a blocking solution (3% bovine serum albumin, 0.05% Tween 20 in 1×PBS) for 2 h at room temperature, then washed with PBST in triplicate. Three-fold serially diluted, duplicate standard samples (100 μL/well) were added to plates in dilution buffer (1% bovine serum albumin, 0.05% Tween 20 in 1×PBS). Unknown samples were diluted 1:10 in dilution buffer and added to plates in duplicate (100 μL/well). Samples were incubated on plates for 1 h at room temperature. Plates were washed and rabbit anti-CTB polyclonal antibody (Abcam; Cambridge, UK) diluted 1:20,000 in dilution buffer (100 μL/well) was added; plates were then incubated at room temperature for 1 h. Plates were washed and goat anti-rabbit IgG-HRP (Southern Biotech; Birmingham, AL, USA) diluted 1:100,000 in dilution buffer was added, followed by incubation at room temperature for 1 h. Plates were washed a final time and developed with TMB. The reaction was stopped with 2 N sulfuric acid and the absorbance at 450 nm was immediately measured with a BioTek plate reader. Percent release was determined by extrapolation of calculated EPT concentrations using CTB sandwich ELISA compared to a known fixed mass of 5 μg EPT per capsule.

Acute DSS Colitis Model and EPT Treatment

Groups of 10 female C57BL/6 mice, randomly assigned, were used. 3% (w/v) DSS (M.W. 36,000-50,000; M.P. Biomedicals; Santa Ana, CA, USA) was administered in drinking water ad libitum for 7 days. Body weights were monitored daily from the start of DSS exposure to sacrifice on day 14. On the last day of DSS exposure, animals were orally gavaged 100 μL PBS, 100 μL of EPT powder dissolved in PBS (0.03 mg/mL solution) after administration of sodium bicarbonate (200 μL of 30 mg/mL solution) as described previously, or enteric coated capsules filled with 5 μg EPT (described above) [15]. Animals recovered with normal drinking water for 7 days. Disease activity index (DAI) scores, consisting of body weight loss, fecal consistency and occult blood tests, were recorded following sacrifice and performed as previously described [25]. Distal colon tissues were fixed in neutral buffered formalin and stained with hematoxalin and eosin (H&E). Histopathological scores, a combination score comprised of crypt architecture, inflammatory infiltrate, muscle thickening and goblet cell presences scores, were determined as previously described [24,25]. Each category was ranked on a scale from 0 to 3 and summed to obtain a single histopathological damage score for each tissue.

Statistics

For all data, outliers were determined by statistical analysis using the Grubb's test and excluded from further analysis if $p<0.05$. Graphs were prepared and analyzed using Graphpad Prism version 5.0 (Graphpad Software; La Jolla, CA, USA). To compare two data sets, an unpaired, two-tailed Student's t test was used. To compare three or more data sets, one-way ANOVA with Bonferroni's multiple-comparison post-test.

Example 2. Pre-Formulation Analysis

Buffers and excipients were screened to determine a combination producing optimal EPT powder. This was determined by assessing pentamer disassembly into monomer, residual moisture, yield, and solubility of powder in water, with a target product profile (TPP) of <5% monomer, <10% moisture, and 100±10% solubility (Table 1). Of the buffers tested, PBS and PBS+100 mM mannitol were chosen from the screened buffers based on the TPP values set for the aforementioned parameters. To assess stability of the chosen buffers, pentamer degradation and water-solubility of EPT formulated in PBS or PBS+100 mM mannitol were analyzed over a period of three weeks (Table 2). The screened and finalized drying conditions are summarized in Table 3. Given the importance of pentamer stability to the epithelial repair activity of EPT [20], PBS+100 mM mannitol was used to optimize drying conditions and subsequent experiments. A variety of inlet and outlet temperature range combinations were assessed to determine which would result in optimal pentamer stability. A lower inlet temperature range (116-122° C.) and higher outlet temperature range (64-67° C.) were found to result in the lowest degree of pentamer degradation. Therefore, these conditions were utilized for subsequent batch productions.

TABLE 2

Stability of EPT powder in chosen buffer excipients

| Buffer | % Monomer | % Moisture | % Loss | % Solubility |
|---|---|---|---|---|
| PBS | 4.9 | 2.9 | 29.3 | 106 |
| PBS, 100 mM Mannitol | 3.1 | 0 | 60.4 | 97 |
| CHT, 42.5% B (diafiltrated) | 3.0 | 6.6 | 41.1 | 121 |
| CHT, 42.5% B (diafiltrated) + 100 Mannitol | 2.0 | 4.6 | 44.4 | 119 |
| 1 Week | | | | |
| PBS | 5.9 | | | 110 |
| PBS, 100 mM Mannitol | 4.0 | | | 97 |
| CHT, 42.5% B (diafiltrated) | 3.6 | | | 132 |
| CHT, 42.5% B (diafiltrated) + 100 Mannitol | 2.3 | | | 114 |
| 2 Weeks | | | | |
| PBS | 4.8 | | | 110 |
| PBS, 100 mM Mannitol | 3.3 | | | 99 |
| CHT, 42.5% B (diafiltrated) | 2.8 | | | 137 |
| CHT, 42.5% B (diafiltrated) + 100 Mannitol | 3.0 | | | 110 |
| 3 Weeks | | | | |
| PBS | 5.9 | | | 110 |
| PBS, 100 mM Mannitol | 3.4 | | | 99 |
| CHT, 42.5% B (diafiltrated) | 3.5 | | | 137 |
| CHT, 42.5% B (diafiltrated) + 100 Mannitol | 3.0 | | | 110 |

TABLE 3

Optimization of spray-dry parameters

| Buffer | % Monomer | % Moisture | % Loss | % Solubility | Q-Flow | Inlet | Outlet | Aspirator | Pump |
|---|---|---|---|---|---|---|---|---|---|
| PBS | 12.3 | 9.7 | 36.2 | 97 | — | 121 | 66-67 | 90 | 20 |
| PBS | 5.9 | 4.5 | 34.5 | 101 | — | 137-140 | 63-65 | 80 | 30 |
| PBS | 3.2 | 32.3 | 29.3 | 101 | — | 119-128 | 61-67 | 90 | 24 |
| PBS | 8.0 | 3.7 | 36.2 | 99 | — | 120 | 61-64 | 90 | 20 |
| PBS | 4.9 | 2.9 | 29.3 | 106 | 35 | 118-125 | 61-65 | 90 | 20 |
| PBS | 11 | — | 51.7 | 99 | 34 | 121-123 | 61-63 | 90 | 20 |
| PBS, 100 mM Mannitol | 4.4 | 3.9 | 60.4 | 101 | | 137-140 | 63-66 | 80 | 30 |
| PBS, 100 mM Mannitol | 3.1 | 0 | 60.4 | 97 | 35 | 120-123 | 62-64 | 90 | 20 |
| PBS, 100 mM Mannitol | 1.0 | 9.5 | 54.2 | 97 | 35 | 116-122 | 64-67 | 95 | 20 |
| PBS, 100 mM Mannitol @ 5 mg/ml | 1.1 | 4.9 | 69.8 | 96 | 35 | 118-122 | 61-63 | 90 | 20 |
| PBS, 100 mM Mannitol | 9 | — | 55 | 119 | 34 | 121-124 | 63-66 | 90 | 20 |

*Finalized drying conditions

Example 3. Stability and Disintegration Testing of EPT Capsules

To demonstrate the stability of the chosen prototype EPT powder immediately after spray-drying, a GM1/KDEL-ELISA and SEC-HPLC were performed to detect the presence of intact KDEL sequence and the conformational state of CTB pentamer, which are crucial for the mucosal healing activity of EPT. This immunoassay and analytical analysis were repeated at 9 months post-spray dry with EPT powder stored under desiccation at 23° C. in parafilm-wrapped tubes. GM1/KDEL-ELISA results demonstrate that GM1 binding affinity of spray dried EPT was unchanged after drying (FIGS. 1A and 1E) and 9 months post-drying when stored under desiccation at 23° C. (FIGS. 1B and 1F). SEC-HPLC chromatograms illustrate the stability of EPT pentamers in 9 months post-drying (FIGS. 1C, 1D, 1G and 1H). The small peak of 8.2% at a retention time of ~18.5 min correlates to EPT monomers (see FIG. 5C), indicating only slight pentamer degradation after 9 months post-drying stored under desiccation at 23° C. (FIGS. 8D and 8I).

Following packing of EPT powder into gelatin capsules and coating with an enteric coating solution, pH-dependent release of EPT was assessed by a capsule disintegration assay. Capsules were coated with Eudragit S100 coating solution to prevent the release of EPT prior to arrival at the proximal colon where the intraluminal pH has increased to ~pH 6.8 after transiting through the stomach and small intestine [26,27]. The capsule disintegration assay simulated passage of the capsule through gastric acid and allowed analysis of the release profile of EPT following exposure to pH 6.8. Recovery of EPT from capsules was determined by a CTB detection sandwich ELISA, which has the capacity to detect both GM1-binding pentamer and disassembled CTB molecular species unlike GM1-capture ELISA (FIGS. 5A-5C), as EPT dissociation could occur if the capsule content was prematurely discharged and exposed to low pH conditions (FIG. 5C). The data revealed that EPT was released from the polymer-coated capsules in a pH-dependent manner (FIG. 2). No EPT was detectable at pH 1.0, suggesting that the enteric coating prevented the release of EPT from capsules prior to expected release at pH 6.8. The same coating solution and method was used to prepare capsules used in the following acute colitis model.

Example 4. Efficacy of EPT Enteric-Coated Capsules in an Acute Colitis Model

It has been demonstrated that oral administration of EPT mitigates mucosal damage and inflammation in preclinical colitis and oral mucositis models. For the preclinical colitis study, a liquid EPT formulation was administered orally after neutralization of gastric acid by pre-administration of a large volume of bicarbonate containing solution because the protein is acid labile.

The efficacy of EPT delivered by this oral capsule formulation was assessed compared to standard EPT in an acute DSS colitis mouse model [15,20]. In this model, animals were exposed to 3% DSS ad libitum in drinking water for 7 days at which time mice were dosed 5 μg resuspended dried EPT (EPT powder solution) or PBS via oral gavage after administration of sodium bicarbonate. A third group of mice were dosed with an enteric-coated capsule containing 5 μg EPT with no administration of sodium bicarbonate. All animals were monitored an additional 7 days following DSS cessation. Compared to PBS, DAI scores were decreased in mice administered a EPT capsule directly as well as sodium bicarbonate followed by reconstituted EPT powder ($p<0.05$ and $p<0.001$, respectively) (FIGS. 3A-3B). To corroborate the aforementioned results, we performed a histopathological evaluation to assess the presence of hallmark colitis markers, such as alterations in crypt height and loss, epithelial barrier disruption, and immune cell infiltration, in hematoxalin and eosin (H&E) stained tissues. EPT powder solution administration following gastric acid neutralization and encapsulated EPT similarly protected mice from DSS-induced acute colitis. Treatment with EPT by capsule administration or oral gavage following gastric acid neutralization protected mice from crypt loss and distortion, inflammatory cell infiltrates, muscle thickening, and goblet cell loss (FIGS. 4A-4B). However, few crypt structural alterations, primarily crypt branching, were noted in tissues from both EPT treatment groups. Taken together, these results support equivalence between EPT treatment in solution following acid neutralization and encapsulated EPT treatment.

EPT is a variant of the nontoxic component of the cholera toxin that exhibits unique mucosal healing activity in the colon [16,18, 21]. Previous studies examining the therapeutic potential of EPT in mouse colitis models have primarily focused on one route of administration: oral gavage. An issue with this route of administration, however, is the need to neutralize gastric acid with sodium bicarbonate prior to gavage as CTB is acid labile. This is a drawback when moving forward with development of EPT as a therapeutic for UC and determining a final drug product formulation. Although oral agents are typically preferred by patients undergoing treatment for chronic diseases such as UC, gastric acid neutralization requirements could potentially affect patient outcomes by lowering adherence and ease of administration. Therefore, a prototype solid oral formulation that would allow EPT to circumvent gastric acid degradation and allow for topical administration to affected areas was developed. Described herein is an encapsulated spray-dried drug substance coated with an enteric coating to allow for pH-dependent release of EPT at the colon.

A major technical advance made in the present study towards a solid oral formulation is the establishment of the method of drying the drug substance. Drying of pharmaceuticals is a long-implemented practice commonly used to enhance final drug product for a variety of purposes; examples of the benefits of biopharmaceutical dehydration include: handling and storage improvement, decrease in transportation cost, improved stability and aid in development of modified or delayed release particles [28,29]. It is known that proteins are more stable in solid rather than liquid form [30-33]. Use of solid formulations can greatly increase shelf-life and reduce storage regulations, saving patients and manufacturers money in lost production costs due to expired product. Further, oral capsules filled with dried protein may be coated with a time- or pH-dependent coating to allow for targeted release in the GI tract [29]. This is especially useful when administering CTB orally as it allows for release at the affected site. Without this coating, orally administered pentameric CTB would degrade into nonfunctional monomers upon exposure to the stomach acid. Dehydrating CTB is one solution to this issue.

Previously, CTB has been dehydrated by a variety of methods. A freeze-dried inactivated whole-cell oral cholera vaccine was formulated in attempts to optimize delivery of mass quantities of vaccine to low-income countries [34]. This formulation elicited strong serum and gut mucosal anti-LPS antibody responses in immunized mice; these responses were comparable to those achieved with equivalent liquid formulation [34]. The dry formulation is beneficial in substantially reducing package volumes and weights when delivering product to areas in need of mass vaccination. Further, CTB has been successfully spray-dried in the form of heat-killed *Vibrio cholerae*-containing microparticles [35]. The benefits of the spray-drying process with EPT was utilized to develop a more optimal oral formulation of the protein. When a protein is spray-dried, conditions need to be tailored to the protein being dried since materials undergo some thermal stress which can result in protein degradation; hence, identification of ideal heating conditions is critical. CTB pentamer degradation occurs approximately between 66° C. and 78° C. [36-38]. Here, outlet temperatures range between 61° C. and 67° C. to maintain stability of functional EPT pentamer were screened. Since optimal TPP parameters were achieved with outlet temperatures closer to 67° C., testing outlet temperatures closer to 78° C. could possibly result in a further improved powder by solubility or moisture content. The most relevant source of stress during spray-drying results from the dehydration process, therefore the addition of excipients to the liquid solution prior to spray drying is crucial to replace the hydrogen bonding that exists in an aqueous environment [29]. In this study, a screen was developed to identify optimal excipient conditions to improve target profile parameters.

A buffer and excipient screen to produce an ideal dried EPT powder based on a set TPP (<5% monomer, <10% moisture, and 100±10% solubility). Addition of mannitol decreased the presence of EPT monomer from approximately 5% to 3% (Tables 2 and 3). As such, addition of mannitol, which is thermostable [39-41], improved stability of EPT pentamer. Because PBS+100 mM mannitol outperformed all other screened buffers in the aforementioned TPP categories, it was therefore chosen as the formulation buffer. All TPP categories were met, however, loss of drug product was a consistent problem as 70% was the maximum recovery among all buffers tested (data not shown). Other studies using this particular spray drier consistently report yields below 50% [42]. Although one issue with this instrument is in aspects of the design, another manageable issue is identifying an ideal inlet to outlet temperature ratio for the protein of interest [42].

Stability of EPT powder produced in the chosen buffer was confirmed by measuring monomer content and percent solubility each week for a total of three weeks (Tables 2 and 3). Low hygroscopicity of mannitol likely had a positive impact on moisture content; it is known that mannitol is an ideal excipient to minimize moisture in a dried formulation [40,41]. Monomer content and solubility remained stable around 3% and 98%, respectively, over the course of three weeks. Mannitol seems to have a protective effect on EPT pentamers, possibly due its thermostability. Other thermoprotective agents, such as dextrose, trehalose and lactose, may also serve as an excipient. Lactose is the most commonly utilized excipient in spray drying [39,43]. mannitol and lactose are both attractive excipients as they are soluble in water and are non-toxic. Lactose has an advantage to mannitol as it is more economical, although it should be noted that lactose has a higher hygroscopicity which can hinder stability of the dried product [39,41]. Further, lactose is more likely to react with active pharmaceutical ingredients as it is a reducing sugar, whereas mannitol exhibits a strong inertness [39].

Upon selection of buffer composition, spray dry parameters were further investigated. Spray dry parameters were optimized by screening a combination of inlet and outlet temperatures to determine a combination producing EPT powder with the best possible TPP values (Table 3). It has been suggested that a high inlet temperature to outlet temperature ratio might be the key to maximizing yield. Our results are consistent with this claim as the highest inlet: outlet temperature condition tested achieved optimal TPP values (Table 3). We also demonstrated via SEC-HPLC and GM1-KDEL detection ELISA that spray dried EPT maintains GM1 binding affinity and remains stable under dry conditions for up to 9 months (FIGS. 1A-1H). This combination of factors indicates that EPT powder encapsulated immediately post-dry and after 9 months should exhibit similar effects upon administration.

Figure 2:
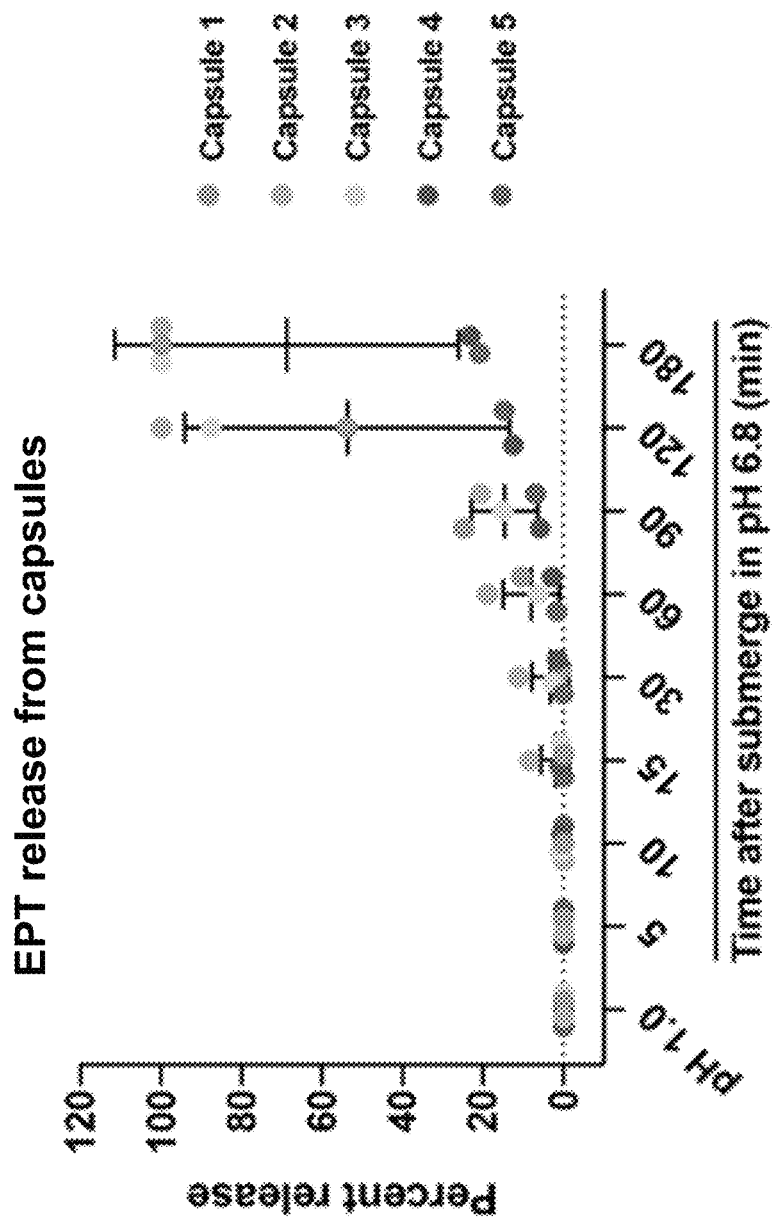
FIG. 2 shows that EPT released from enteric-coated capsules is pH-dependent. Release of EPT was measured by CTB sandwich ELISA. EPT releases from capsules only after submersion at pH 6.8. Percent of EPT release from capsules after 2 h submersion in 0.1 N HCl, and at t=5, 10, 15, 30, 60, 90, 120, and 180 min after pH shift to 6.8. n=5. Percent release was determined by extrapolation of calculated EPT concentrations using CTB sandwich ELISA compared to a known fixed mass of 5 µg EPT per capsule.
Figure 3A:
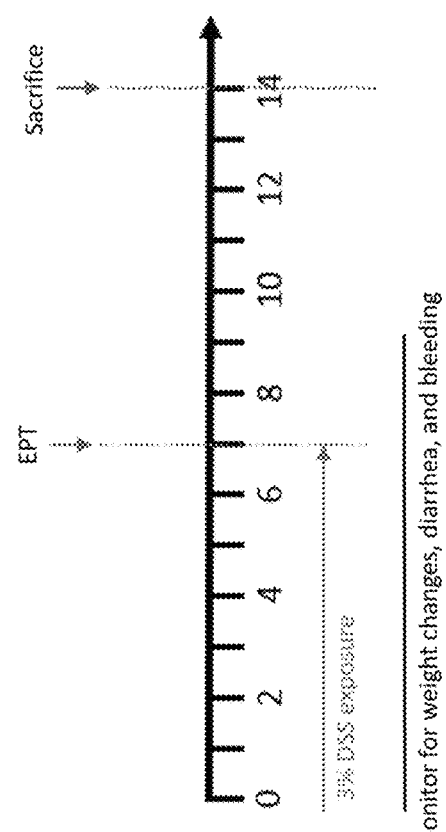
FIGS. 3A-3B. Enteric-coated EPT capsules mitigate acute DSS colitis in mice.
Figure 3B:
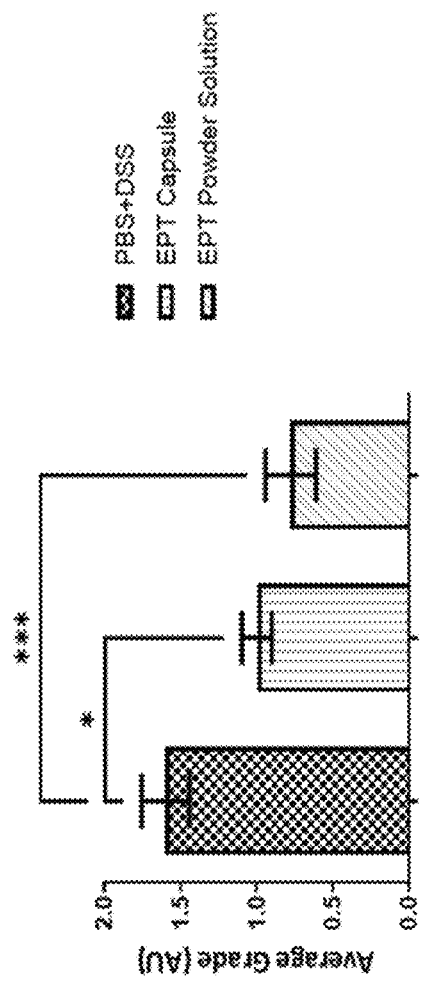
Figure 4A:
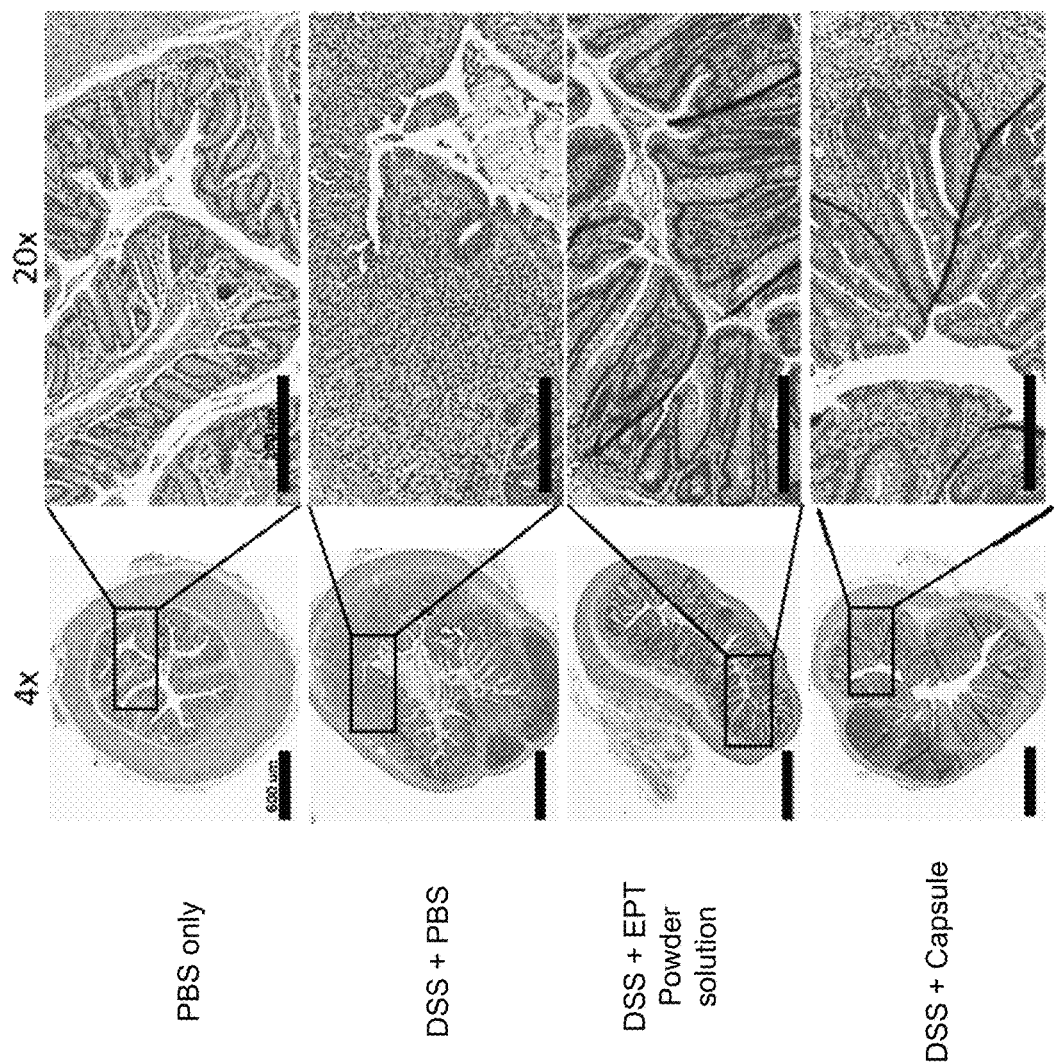
FIGS. 4A-4B. Treatment with encapsulated EPT mitigates acute colitis in mice. Encapsulated EPT (DSS+Capsule) treatment protected mice from histological damage similarly to treatment with EPT powder solution following gastric acid neutralization (DSS+EPT powder solution).
Figure 4B:
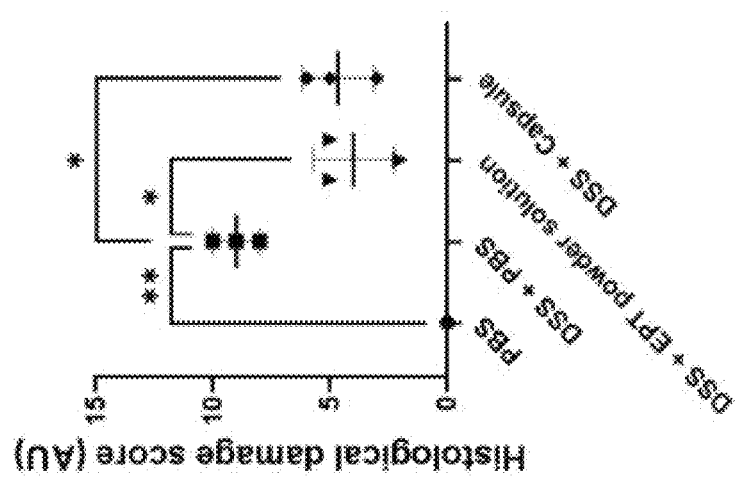
Figure 5A:
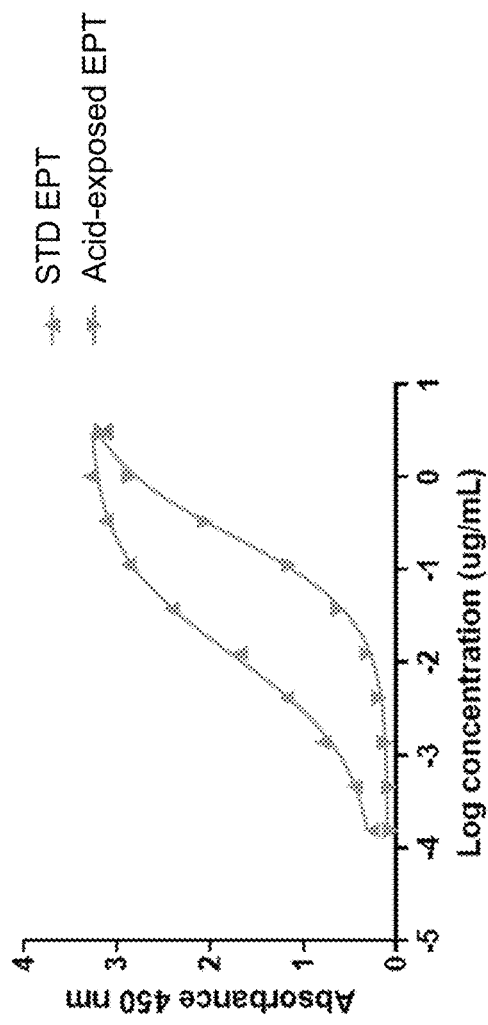
FIGS. 5A-5C. Evidence for EPT degradation at pH 1.0, These results demonstrate the need for a pH-dependent oral formulation of EPT.
Figure 5B:
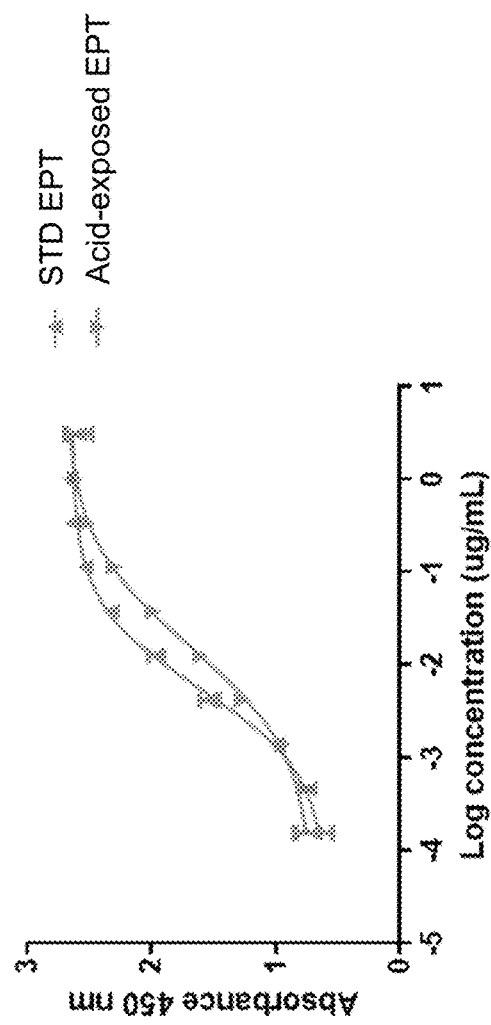
Figure 5C:
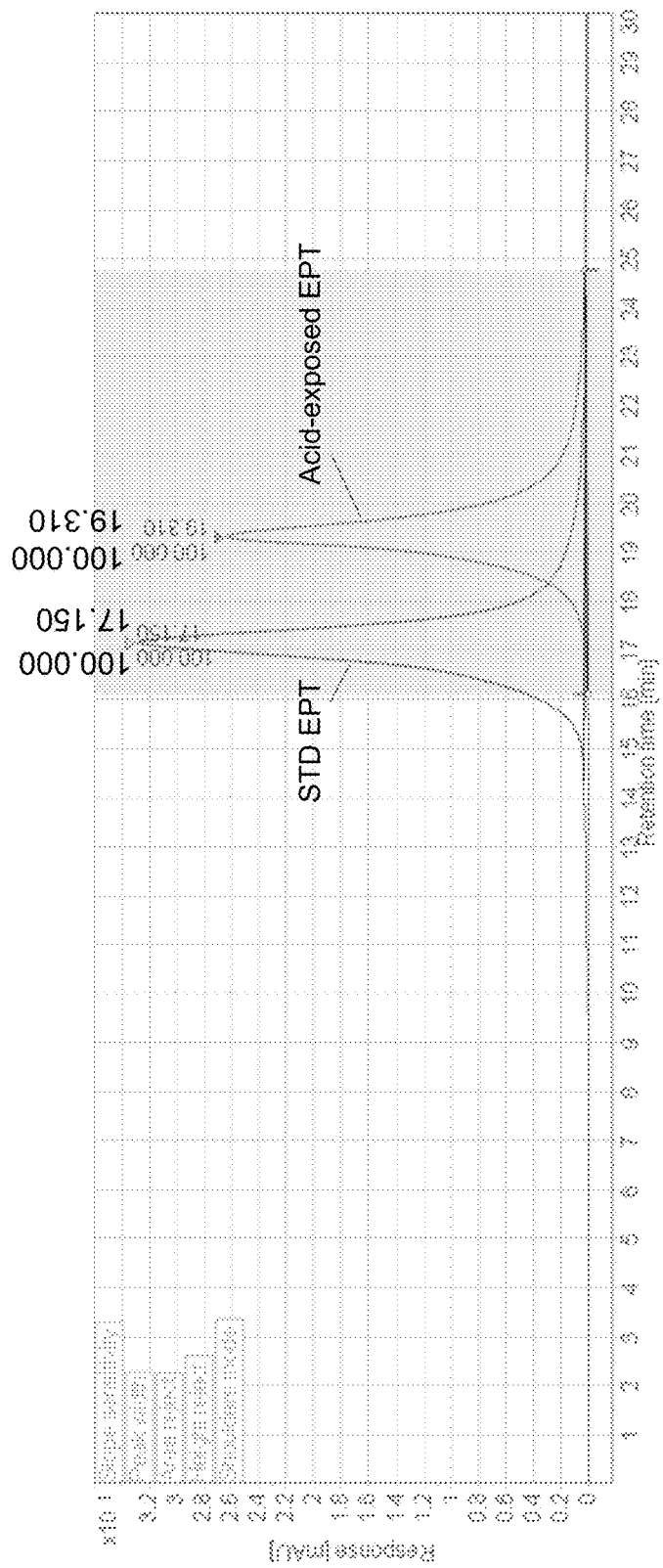

The oral formulation presented here was designed for direct delivery of EPT to the target site by utilizing an anionic polymer coating that makes pH-dependent release at the colon possible. The in vitro disintegration test suggested that not all capsules released 100% of encased EPT (FIG. 2). It is possible that there are inconsistencies in the thickness of the enteric coating around the capsules, leading to variations in release profiles. The combination of dipping capsules by and viscosity of the solution could lead to disparities between capsule coatings. This could be ameliorated by coating the capsules using an automated system that would likely be utilized when coating capsules at an industrial scale. Further, it was observed during disintegration testing that capsules tend to fold in on themselves when freefloating in solution. This is an unlikely issue in vivo as movement through the GI tract would prevent the folding over of capsules. In support of this hypothesis, the acute DSS study showed that the enteric-coated EPT capsule ameliorated acute DSS-induced colitis, indicating that the protein was successfully released from the capsules at the site of mucosal damage (FIGS. 3A-4B). The histopathological results described here are also consistent with previous findings in acute and chronic DSS colitis studies evaluating EPT treatment [16,17,21]. Taken together, these results show that treatment using the capsule formulation described herein does not require gastric acid neutralization, and would theoretically ease difficulty of administration and boost patient adherence in UC patients.

EPT is a recombinant variant of the cholera toxin B subunit, modified with a C-terminal KDEL endoplasmic reticulum retention motif. EPT has therapeutic potential for ulcerative colitis treatment. Previously, orally administered EPT demonstrated colon epithelial repair activity in dextran sodium sulfate (DSS)-induced acute and chronic colitis in mice. However, the oral dosing requires cumbersome pretreatment with sodium bicarbonate to conserve the acid-labile drug substance while transit through the stomach, hampering its facile application in chronic disease treatment. Here, we developed a solid oral formulation of EPT that circumvents degradation in gastric acid. EPT was spray-dried and packed into enteric-coated capsules to allow for pH-dependent release in the colon. A GM1-capture KDEL-detection ELISA and size-exclusion HPLC indicated that EPT powder maintains activity and structural stability for up to 9 months. Capsule disintegration tests showed that EPT remained encapsulated at pH 1 but was released over 180 min at pH 6.8, the approximate pH of the proximal colon. An acute DSS colitis study confirmed the therapeutic efficacy of encapsulated EPT in C57BL/6 mice upon oral administration without gastric acid neutralization pretreatment compared to vehicle-treated mice (p<0.05). These results provide a foundation for an enteric-coated oral formulation of spray-dried EPT.

Dry formulation has several advantages for storage, drug compounding, drug delivery system development. The development and demonstration of this technology is another critical step towards commercialization of EPT for human therapeutic use. No products currently available for UC or in development possess the combination of attributes that this product would offer. It is anticipated that the combination of EPT's unique wound healing effect and the convenience of a solid dosage form will represent a highly desired "first in class" treatment with the potential to transform UC standard of care.

The developed dry formulated EPT allows for effortless formulation for targeted delivery, ease of administration and higher patient acceptance, which will in turn help assure higher treatment compliance in chronic therapy scenarios.

While example embodiments have been particularly shown and described, it will be understood by those skilled in the art that various changes in form and details may be made therein without departing from the scope of the embodiments encompassed by the appended claims.

Sequences

A nucleic acid sequence of a wild-type cholera toxin B subunit from *Vibrio cholerae*:

(SEQ ID NO: 1)
accccacaaaacatcactgacttgtgtgctgagtaccacaacacccaaa tccacaccctcaatgacaagatctttagctacaccgagagccttgctgg caagagggagatggctatcatcaccttcaagaatggtgctaccttccaa gtggaggtgcctggaagccaacacattgatagccaaaagaaggccattg agaggatgaaggacacacttaggatagcttacctcactgaggctaaggt ggagaagctttgtgtgtggaacaacaagaccccccatgctattgctgcc atcagcatggccaac.

An amino acid sequence of a wild-type cholera toxin B subunit from *Vibrio cholerae*.

(SEQ ID NO: 2)
TPQNITDLCAEYHNTQIHTLNDKIFSYTESLAGKREMAIITFKNGATFQ

VEVPGSQHIDSQKKAIERMKDTLRIAYLTEAKVEKLCVWNNKTPHAIAA

ISMAN.

A nucleic acid sequence encoding a cholera toxin B subunit variant polypeptide modified to include a C-terminal endoplasmic reticulum signal and to include no N-linked glycosylation sequons at Asn4:

(SEQ ID NO: 3)
accccacaaagcatcactgacttgtgtgctgagtaccacaacacccaaa tccacaccctcaatgacaagatctttagctacaccgagagccttgctgg caagagggagatggctatcatcaccttcaagaatggtgctaccttccaa gtggaggtgcctggaagccaacacattgatagccaaaagaaggccattg agaggatgaaggacacacttaggatagcttacctcactgaggctaaggt ggagaagctttgtgtgtggaacaacaagaccccccatgctattgctgcc atcagcatggccaactccgagaaggatgaactc.

An amino acid sequence of a cholera toxin B subunit variant polypeptide modified to include a C-terminal endoplasmic reticulum signal and to include no N-linked glycosylation sequons at Asn4:

(SEQ ID NO: 4)
TPQSITDLCAEYHNTQIHTLNDKIFSYTESLAGKREMAIITFKNGATFQ

VEVPGSQHIDSQKKAIERIVIKDTLRIAYLTEAKVEKLCVWNNKTPHAI

AAISMANSEKDEL.

A nucleic acid sequence encoding a cholera toxin B subunit variant polypeptide modified to include a C-terminal endoplasmic reticulum retention signal and having one N-linked glycosylation sequon at Asn4:

(SEQ ID NO: 5)
accccacaaaacatcactgacttgtgtgctgagtaccacaacacccaaa tccacaccctcaatgacaagatctttagctacaccgagagccttgctgg

```
caagagggagatggctatcatcaccttcaagaatggtgctaccttccaa gtggaggtgcctggaagccaacacattgatagccaaaagaaggccattg agaggatgaaggacacacttaggatagcttacctcactgaggctaaggt ggagaagctttgtgtgtggaacaacaagaccccccatgctattgctgcc atcagcatggccaactccgagaaggatgaactc.
```

An amino acid sequence of a cholera toxin B subunit variant polypeptide modified to include a C-terminal endoplasmic reticulum retention signal and having one N-linked glycosylation sequon at Asn4:

```
                                          (SEQ ID NO: 6)
TPQNITDLCAEYHNTQIHTLNDKIFSYTESLAGKREMAIITFKNGATFQ

VEVPGSQHIDSQKKAIERMKDTLRIAYLTEAKVEKLCVWNNKTPHAIAA

ISMANSEKDEL.
```

A nucleic acid sequence encoding a cholera toxin B subunit variant polypeptide modified to include a C-terminal endoplasmic reticulum retention signal and to include two N-linked glycosylation sequons at Asn4 and Asn103:

```
                                          (SEQ ID NO: 7)
accccacaaaacatcactgacttgtgtgctgagtaccacaacacccaaa tccacaccctcaatgacaagatctttagctacaccgagagccttgctgg caagagggagatggctatcatcaccttcaagaatggtgctaccttccaa gtggaggtgcctggaagccaacacattgatagccaaaagaaggccattg agaggatgaaggacacacttaggatagcttacctcactgaggctaaggt ggagaagctttgtgtgtggaacaacaagaccccccatgctattgctgcc atcagcatggccaacgttactaaggatgaactc.
```

An amino acid sequence of a cholera toxin B subunit variant polypeptide modified to include a C-terminal endoplasmic reticulum retention signal and to include two N-linked glycosylation sequons at Asn4 and Asn103:

```
                                          (SEQ ID NO: 8)
TPQNITDLCAEYHNTQIHTLNDKIFSYTESLAGKREMAIITFKNGATFQ

VEVPGSQHIDSQKKAIERMKDTLRIAYLTEAKVEKLCVWNNKTPHAIAA

ISMANVTKDEL.
```

A nucleic acid sequence encoding another cholera toxin B subunit variant polypeptide modified to include a C-terminal endoplasmic reticulum retention signal and to include two N-linked glycosylation sequons at Asn4 and Asn21:

```
                                          (SEQ ID NO: 9)
accccacaaaacatcactgacttgtgtgctgagtaccacaacacccaaa tccacaccctcaatgacactatctttagctacaccgagagccttgctgg caagagggagatggctatcatcaccttcaagaatggtgctaccttccaa gtggaggtgcctggaagccaacacattgatagccaaaagaaggccattg agaggatgaaggacacacttaggatagcttacctcactgaggctaaggt ggagaagctttgtgtgtggaacaacaagaccccccatgctattgctgcc atcagcatggccaactccgagaaggatgaactc.
```

An amino acid sequence of another cholera toxin B subunit variant polypeptide modified to include a C-terminal endoplasmic reticulum retention signal and to include two N-linked glycosylation sequons at Asn4 and Asn21:

```
                                          (SEQ ID NO: 10)
TPQNITDLCAEYHNTQIHTLNDTIFSYTESLAGKREMAIITFKNGATFQ

VEVPGSQHIDSQKKAIERMKDTLRIAYLTEAKVEKLCVWNNKTPHAIAA

ISMANSEKDEL.
```

A nucleic acid sequence encoding a cholera toxin B subunit variant polypeptide modified to include a C-terminal endoplasmic reticulum retention signal and to include three N-linked glycosylation sequons at Asn4, Asn21, and Asn103:

```
                                          (SEQ ID NO: 11)
accccacaaaacatcactgacttgtgtgctgagtaccacaacacccaaa tccacaccctcaatgacactatctttagctacaccgagagccttgctgg caagagggagatggctatcatcaccttcaagaatggtgctaccttccaa gtggaggtgcctggaagccaacacattgatagccaaaagaaggccattg agaggatgaaggacacacttaggatagcttacctcactgaggctaaggt ggagaagctttgtgtgtggaacaacaagaccccccatgctattgctgcc atcagcatggccaacgttactaaggatgaactc.
```

An amino acid sequence of a cholera toxin B subunit variant polypeptide modified to include a C-terminal endoplasmic reticulum retention signal and to include three N-linked glycosylation sequons at Asn4, Asn21, and Asn103:

```
                                          (SEQ ID NO: 12)
TPQNITDLCAEYHNTQIHTLNDTIFSYTESLAGKREMAIITFKNGATFQ

VEVPGSQHIDSQKKAIERIVIKDTLRIAYLTEAKVEKLCVWNNKTPHAI

AAISMANVTKDEL.
```

A nucleic acid sequence encoding another cholera toxin B subunit variant polypeptide modified to include a C-terminal endoplasmic reticulum retention signal and to include three N-linked glycosylation sequons at Asn4, Asn21, and Asn103:

```
                                          (SEQ ID NO: 13)
accccacaaaacatcactgacttgtgtgctgagtaccacaacacccaaa tccacaccctcaatgacactatctttagctacaccgagagccttgctgg caagagggagatggctatcatcaccttcaagaatggtgctaccttccaa gtggaggtgcctggaagccaacacattgatagccaaaagaaggccattg agaggatgaaggacacacttaggatagcttacctcactgaggctaaggt ggagaagctttgtgtgtggaacaacaagaccccccatgctattgctgcc
```

-continued atcagcatggccaacgttactggtggtggaggatccgagaaggatgaac tc.

An amino acid sequence of another cholera toxin B subunit variant polypeptide modified to include a C-terminal endoplasmic reticulum retention signal and to include three N-linked glycosylation sequons at Asn4, Asn21, and Asn103:

(SEQ ID NO: 14)
TPQNITDLCAEYHNTQIHTLNDTIFSYTESLAGKREMAIITFKNGATFQ

VEVPGSQHIDSQKKAIERMKDTLRIAYLTEAKVEKLCTPHAIAAISMAN

VTGGGGSEKDEL.

A nucleic acid sequence encoding a cholera toxin B subunit variant polypeptide with an N-terminal secretory signal from *Vibrio cholerae* and a C-terminal endoplasmic reticulum retention signal:

(SEQ ID NO: 15)
atggctatcaagctcaagtttggagtgttcttcactgtgctcttagct ctgcctatgcacatggcaccccacaaaacatcactgacttgtgtgctga gtaccacaacacccaaatccacaccctcaatgacaagatctttagctac accgagagccttgctggcaagagggagatggctatcatcaccttcaaga atggtgctaccttccaagtggaggtgcctggaagccaacacattgatag ccaaaagaaggccattgagaggatgaaggacacacttaggatagcttac ctcactgaggctaaggtggagaagctttgtgtgtggaacaacaagaccc cccatgctattgctgccatcagcatggccaactccgagaaggatgaact c.

An amino acid sequence of a cholera toxin B subunit variant polypeptide including an N-terminal secretory signal from *Vibrio cholerae* and a C-terminal endoplasmic reticulum retention signal:

(SEQ ID NO: 16)
MAIKLKFGVFFTVLLSSAYAHGTPQNITDLCAEYHNTQIHTLNDKIFSYT

ESLAGKREMAIITFKNGATFQVEVPGSQHIDSQKKAIERMKDTLRIAYLT

EAKVEKLCVWNNKTPHAIAAISMANSEKDEL.

A nucleic acid sequence encoding a rice alpha-amylase secretory signal peptide:

(SEQ ID NO: 17)
atggggaagcaaatggccgccctgtgtggctttctcctcgtggcgttgct ctggctcacgcccgacgtcgcgcatggt.

An amino acid sequence of a rice alpha-amylase secretory signal peptide:

(SEQ ID NO: 18)
MGKQMAALCGFLLVALLWLTPDVAHG.

A nucleic acid sequence encoding a *Nicotiana* plumbagenifolia calreticulin secretory signal peptide:

(SEQ ID NO: 19)
atggctactcaacgaagggcaaaccctagctctctccatctaattactgt attctctctgctcgtcgctgtcgtctcaggt An amino acid sequence of a *Nicotiana* plumbagenifolia calreticulin secretory signal peptide:

(SEQ ID NO: 20)
MATQRRANPSSLHLITVFSLLVAVVSG.

A nucleic acid sequence encoding an apple pectinase secretory signal peptide:

(SEQ ID NO: 21)
atggcattgaagacacagttgttgtggtcattcgtggttgtgttcgttgt gtccttcagtacaacttcatgctcaggt.

An amino acid sequence of an apple pectinase secretory signal peptide:

(SEQ ID NO: 22)
MALKTQLLWSFVVVFVVSFSTTSCSG.

A nucleic acid sequence encoding a barley alpha-amylase secretory signal peptide:

(SEQ ID NO: 23)
atggcgaacaaacacttgtccctctccctcttcctcgtcctccttggcct gtcggccagcttggcctcaggt.

An amino acid sequence encoding a barley alpha-amylase secretory signal peptide:

(SEQ ID NO: 24)
MANKHLSLSLFLVLLGLSASLASG.

An amino acid sequence of a cholera toxin B subunit variant polypeptide including a Ser26-to-Cys and an Ala102-to-Cys mutation:

(SEQ ID NO: 25)
TPQNITDLCAEYHNTQIHTLNDKIFCYTESLAGKREMAIITFKNGATFQV

EVPGSQHIDSQKKAIERMKDTLRIAYLTEAKVEKLCVWNNKTPHAIAAIS

MCNSEKDEL.

An amino acid sequence of a cholera toxin B subunit variant polypeptide including a rice alpha-amylase N-terminal secretory signal peptide and a C-terminal endoplasmic reticulum retention signal peptide:

(SEQ ID NO: 26)
MGKQMAALCGFLLVALLWLTPDVAHGTPQNITDLCAEYHNTQIHTLNDKI

FSYTESLAGKREMAIITFKNGATFQVEVPGSQHIDSQKKAIERMKDTLRI

AYLTEAKVEKLCVWNNKTPHAIAAISMANSEKDEL.

An amino acid sequence of a cholera toxin B subunit variant polypeptide including a *Nicotiana* plumbagenifolia calreticulin N-terminal secretory signal peptide and a C-terminal endoplasmic reticulum retention signal peptide:

(SEQ ID NO: 27)
MATQRRANPSSLHLITVFSLLVAVVSGTPQNITDLCAEYHNTQIHTLNDK

IFSYTESLAGKREMAIITFKNGATFQVEVPGSQHIDSQKKAIERMKDTLR

IAYLTEAKVEKLCVWNNKTPHAIAAISMANSEKDEL.

An amino acid sequence of a cholera toxin B subunit variant polypeptide including an apple pectinase N-terminal secretory signal peptide and a C-terminal endoplasmic reticulum retention signal peptide:

(SEQ ID NO: 28)
MALKTQLLWSFVVVFVVSFSTTSCSGTPQNITDLCAEYHNTQIHTLNDKI

FSYTESLAGKREMAIITFKNGATFQVEVPGSQHIDSQKKAIERMKDTLRI

AYLTEAKVEKLCVWNNKTPHAIAAISMANSEKDEL.

An amino acid sequence of a cholera toxin B subunit variant polypeptide including a barley alpha-amylase N-terminal secretory signal peptide and a C-terminal endoplasmic reticulum retention signal peptide:

(SEQ ID NO: 29)
MANKHLSLSLFLVLLGLSASLASGTPQNITDLCAEYHNTQIHTLNDKIFS

YTESLAGKREMAIITFKNGATFQVEVPGSQHIDSQKKAIERMKDTLRIAY

LTEAKVEKLCVWNNKTPHAIAAISMANSEKDEL.

Amino acids of non-limiting examples of endoplasmic reticulum retention signal peptides, with or without a two-amino acid linker, SE: SEKDEL (SEQ ID NO: 30), KDEL (SEQ ID NO: 31), SEHDEL (SEQ ID NO: 32), and HDEL (SEQ ID NO: 33).

An amino acid sequence of a cholera toxin B subunit variant polypeptide including a rice alpha-amylase N-terminal secretory signal peptide and a C-terminal endoplasmic reticulum retention signal peptide:

(SEQ ID NO: 34)
MGKQMAALCGFLLVALLWLTPDVAHGTPQSITDLCAEYHNTQIHTLNDKI

FSYTESLAGKREMAIITFKNGATFQVEVPGSQHIDSQKKAIERMKDTLRI

AYLTEAKVEKLCVWNNKTPHAIAAISMANSEKDEL.

REFERENCES

1. Zhang, Y. Z.; Li, Y. Y. Inflammatory bowel disease: Pathogenesis. World J. Gastroenterol. 2014, 20, 91-99.
2. The Facts about Inflammatory Bowel Diseases; Crohn's & Colitis Foundation: New York, NY, USA, 2014.
3. Lautenschlager, C.; Schmidt, C.; Fischer, D.; Stallmach, A. Drug delivery strategies in the therapy of inflammatory bowel disease. Adv. Drug Deliv. Rev. 2014, 71, 58-76.
4. Anwer, M. K.; Ahmed, M. M.; Aldawsari, M. F.; Alshahrani, S.; Fatima, F.; Ansari, M. N.; Rehman, N. U.; Al-Shdefat, R. I. Eluxadoline Loaded Solid Lipid Nanoparticles for Improved Colon Targeting in Rat Model of Ulcerative Colitis. Pharmaceuticals 2020, 13, 255.
5. Yadav, V.; Varum, F.; Bravo, R.; Furrer, E.; Basit, A. W. Gastrointestinal stability of therapeutic anti-TNFα IgG1 monoclonal antibodies. Int. J. Pharm. 2016, 502, 181-187.
6. Gallo, G.; Kotze, P. G.; Spinelli, A. Surgery in ulcerative colitis: When? How? Best Pract. Res. Clin. Gastroenterol. 2018, 32-33, 71-78.
7. Fell, J. M.; Muhammed, R.; Spray, C.; Crook, K.; Russell, R. K. Management of ulcerative colitis. Arch. Dis. Child. 2016, 101, 469-474.
8. Danese, S.; Fiorino, G.; Peyrin-Biroulet, L. Positioning Therapies in Ulcerative Colitis. Clin. Gastroenterol. Hepatol. 2020, 18, 1280-1290.e1.
9. Tripathi, K.; Feuerstein, J. D. New developments in ulcerative colitis: Latest evidence on management, treatment, and maintenance. Drugs Context 2019, 8, 212572.
10. Feuerstein, J. D.; Moss, A. C.; Farraye, F. A. Ulcerative Colitis. Mayo Clin. Proc. 2019, 94, 1357-1373.
11. Boal Carvalho, P.; Cotter, J. Mucosal Healing in Ulcerative Colitis: A Comprehensive Review. Drugs 2017, 77, 159-173.
12. Pineton de Chambrun, G.; Blanc, P.; Peyrin-Biroulet, L. Current evidence supporting mucosal healing and deep remission as important treatment goals for inflammatory bowel disease. Expert Rev. Gastroenterol. Hepatol. 2016, 10, 915-927.
13. Gunnarsson, C.; Chen, J.; Rizzo, J. A.; Ladapo, J. A.; Lofland, J. H. Direct health care insurer and out-of-pocket expenditures of inflammatory bowel disease: Evidence from a US national survey. Dig. Dis. Sci. 2012, 57, 3080-3091.
14. Leoni, G.; Neumann, P. A.; Sumagin, R.; Denning, T. L.; Nusrat, A. Wound repair: Role of immune-epithelial interactions. Mucosal Immunol. 2015, 8, 959-968.
15. Baldauf, K. J.; Royal, J. M.; Kouokam, J. C.; Haribabu, B.; Jala, V. R.; Yaddanapudi, K.; Hamorsky, K. T.; Dryden, G. W.; Matoba, N. Oral administration of a recombinant cholera toxin B subunit promotes mucosal healing in the colon. Mucosal Immunol. 2017, 10, 887-900.
16. Royal, J. M.; Reeves, M. A.; Matoba, N. Repeated Oral Administration of a KDEL-tagged Recombinant Cholera Toxin B Subunit Effectively Mitigates DSS Colitis Despite a Robust Immunogenic Response. Toxins 2019, 11, 678. [CrossRef]
17. Royal, J. M.; Matoba, N. Therapeutic Potential of Cholera Toxin B Subunit for the Treatment of Inflammatory Diseases of the Mucosa. Toxins 2017, 9, 379.
18. Hamorsky, K. T.; Kouokam, J. C.; Bennett, L. J.; Baldauf, K. J.; Kajiura, H.; Fujiyama, K.; Matoba, N. Rapid and scalable plant-based production of a cholera toxin B subunit variant to aid in mass vaccination against cholera outbreaks. PLoS Negl. Trop. Dis. 2013, 7, e2046.
19. Hamorsky, K. T.; Kouokam, J. C.; Jurkiewicz, J. M.; Nelson, B.; Moore, L. J.; Husk, A. S.; Kajiura, H.; Fujiyama, K.; Matoba, N. N-glycosylation of cholera toxin B subunit in *Nicotiana benthamiana*: Impacts on host stress response, production yield and vaccine potential. Sci. Rep. 2015, 5, 8003.
20. Royal, J. M.; Oh, Y. J.; Grey, M. J.; Lencer, W. I.; Ronquillo, N.; Galandiuk, S.; Matoba, N. A modified cholera toxin B subunit containing an ER retention motif enhances colon epithelial repair via an unfolded protein response. FASEB J. 2019, 33, 13527-13545.
21. Feuerstein, J. D.; Cheifetz, A. S. Ulcerative colitis: Epidemiology, diagnosis, and management. Mayo Clin. Proc. 2014, 89, 1553-1563.
22. Kim, J. J.; Shajib, M. S.; Manocha, M. M.; Khan, W. I. Investigating intestinal inflammation in DSS-induced model of IBD. J. Vis. Exp. 2012, 3678.
23. Cooper, H. S.; Murthy, S. N.; Shah, R. S.; Sedergran, D. J. Clinicopathologic study of dextran sulfate sodium experimental murine colitis. Lab. Investig. 1993, 69, 238-249.

24. Morris, D. A.; Reeves, M. A.; Royal, J. M.; Hamorsky, K. T.; Matoba, N. Isolation and detection of a KDEL-tagged recombinant cholera toxin B subunit from *Nicotiana benthamiana*. Process Biochem. 2021, 101, 42-49.
25. Wirtz, S.; Popp, V.; Kindermann, M.; Gerlach, K.; Weigmann, B.; Fichtner-Feigl, S.; Neurath, M. F. Chemically induced mouse models of acute and chronic intestinal inflammation. Nat. Protoc. 2017, 12, 1295-1309.
26. Nugent, S. G.; Kumar, D.; Rampton, D. S.; Evans, D. F. Intestinal luminal pH in inflammatory bowel disease: Possible determinants and implications for therapy with aminosalicylates and other drugs. Gut 2001, 48, 571-577.
27. Koziolek, M.; Grimm, M.; Becker, D.; Iordanov, V.; Zou, H.; Shimizu, J.; Wanke, C.; Garbacz, G.; Weitschies, W. Investigation of pH and Temperature Profiles in the GI Tract of Fasted Human Subjects Using the Intellicap® System. J. Pharm. Sci. 2015, 104, 2855-2863.
28. Langford, A.; Bhatnagar, B.; Walters, R.; Tchessalov, S.; Ohtake, S. Drying technologies for biopharmaceutical applications: Recent developments and future direction. Dry. Technol. 2018, 36, 677-684.
29. Sollohub, K.; Cal, K. Spray drying technique: II. Current applications in pharmaceutical technology. J. Pharm. Sci. 2010, 99, 587-597.
30. Ajmera, A.; Scherließ, R. Stabilisation of proteins via mixtures of amino acids during spray drying. Int. J. Pharm. 2014, 463, 98-107.
31. Maltesen, M. J.; van de Weert, M. Drying methods for protein pharmaceuticals. Drug Discov. Today Technol. 2008, 5, e81-e88.
32. Liao, Y. H.; Brown, M. B.; Martin, G. P. Investigation of the stabilisation of freeze-dried lysozyme and the physical properties of the formulations. Eur. J. Pharm. Biopharm. 2004, 58, 15-24.
33. Tian, F.; Sane, S.; Rytting, J. H. calorimetric investigation of protein/amino acid interactions in the solid state. Int. J. Pharm. 2006, 310, 175-186.
34. Borde, A.; Larsson, A.; Holmgren, J.; Nygren, E. Preparation and evaluation of a freeze-dried oral killed cholera vaccine formulation. Eur. J. Pharm. Biopharm. 2011, 79, 508-518.
35. Pastor, M.; Esquisabel, A.; Marquinez, I.; Talavera, A.; Pedraz, J. L. Cellulose acetate phthalate microparticles containing *Vibrio cholerae*: Steps toward an oral cholera vaccine. J. Drug Target. 2014, 22, 478-487.
36. Goins, B.; Freire, E. Thermal stability and intersubunit interactions of cholera toxin in solution and in association with its cell-surface receptor ganglioside GM1. Biochemistry 1988, 27, 2046-2052.
37. Zhang, R. G.; Westbrook, M. L.; Westbrook, E. M.; Scott, D. L.; Otwinowski, Z.; Maulik, P. R.; Reed, R. A.; Shipley, G. G. The 2.4 A crystal structure of cholera toxin B subunit pentamer: Choleragenoid. J. Mol. Biol. 1995, 251, 550-562.
38. Surewicz, W. K.; Leddy, J. J.; Mantsch, H. H. Structure, stability, and receptor interaction of cholera toxin as studied by Fourier transform infrared spectroscopy. Biochemistry 1990, 29, 8106-8111.
39. Ohrem, H. L.; Schornick, E.; Kalivoda, A.; Ognibene, R. Why is mannitol becoming more and more popular as a pharmaceutical excipient in solid dosage forms? Pharm. Dev. Technol. 2014, 19, 257-262.
40. Naini, V. Physical and Chemical Stability of Spray Dried Sugars and Protein-Sugar Molecular Mixtures for Inhalation. Ph.D. Thesis, Virginia Commonwealth University, Richmond, VA, USA, 1996.
41. Rowe, R. C.; Sheskey, P.; Quinn, M. Handbook of Pharmaceutical Excipients; Libros Digitales-Pharmaceutical Press: London, UK, 2009.
42. Maury, M.; Murphy, K.; Kumar, S.; Shi, L.; Lee, G. Effects of process variables on the powder yield of spray-dried trehalose on a laboratory spray-dryer. Eur. J. Pharm. Biopharm. 2005, 59, 565-573.
43. Jain, M.; Ganesh, L.; Manoj, B.; Randhir, C.; Shashikant, B.; Chirag, S. Spray Drying in Pharmaceutical Industry: A Review. Res. J. Pharm. Dos. Forms Technol. 2012, 4, 74-79.

The teachings of all patents, published applications and references cited herein are incorporated by reference in their entirety.

What is claimed is:

1. A powder comprising a cholera toxin B subunit variant and mannitol, wherein the cholera toxin B subunit variant and mannitol have a weight ratio of between about 1:3.6 and about 1:45.5.

2. The powder of claim 1, wherein the cholera toxin B subunit variant comprises an amino acid sequence that has at least about 80% sequence identity to at least one sequence set forth in SEQ ID NOs:2, 4, 6, 8, 10, 12, 14, 16, 25-29 and 34.

3. The powder of claim 1, wherein the cholera toxin B subunit variant comprises an endoplasmic reticulum (ER) retention sequence attached to its C-terminus.

4. The powder of claim 3, wherein the ER retention sequence comprises SEKDEL (SEQ ID NO:30), KDEL (SEQ ID NO:31), SEHDEL (SEQ ID NO:32) or HDEL (SEQ ID NO:33).

5. The powder of claim 1, wherein the cholera toxin B subunit variant comprises an amino acid sequence set forth in SEQ ID NO:4 or SEQ ID NO:34.

6. The powder of claim 1, wherein the cholera toxin B subunit variant and mannitol have a weight ratio of between about 1:3.6 and about 1:18.3.

7. The powder of claim 1, wherein the cholera toxin B subunit variant and mannitol have a weight ratio of between about 1:18.2 and about 1:45.5.

8. The powder of claim 1, wherein the cholera toxin B subunit variant and mannitol have a weight ratio of between about 1:18.2 and about 1:18.3.

9. The powder of claim 1, further comprising KCl, $KH_2PO_4$, NaCl, and $Na_2HPO_4$.

10. The powder of claim 1, wherein less than 10% of the cholera toxin B subunit variant is a monomer.

11. The powder of claim 1, wherein less than 5% of the cholera toxin B subunit variant is a monomer.

12. A pharmaceutical composition comprising the powder of claim 1, wherein the pharmaceutical composition is suitable for oral administration to a subject.

13. The pharmaceutical composition of claim 12, wherein the pharmaceutical composition is in a form of a capsule, and wherein the capsule comprises a polymer that degrades at about pH 6.8.

14. A powder comprising:
a) a cholera toxin B subunit variant comprising an amino acid sequence that has at least about 80% sequence identity to at least one sequence set forth in SEQ ID NOs:2, 4, 6, 8, 10, 12, 14, 16, 25-29 and 34, and
b) mannitol,
wherein the cholera toxin B subunit variant and mannitol have a weight ratio of between about 1:3.6 and about 1:45.5.

15. The powder of claim 14, wherein the cholera toxin B subunit variant and mannitol have a weight ratio of between about 1:3.6 and about 1:18.3.

16. The powder of claim 14, wherein the cholera toxin B subunit variant and mannitol have a weight ratio of between about 1:18.2 and about 1:45.5.

17. The powder of claim 14, wherein the cholera toxin B subunit variant and mannitol have a weight ratio of between about 1:18.2 and about 1:18.3.

18. The powder of claim 14, further comprising KCl, $KH_2PO_4$, NaCl, and $Na_2HPO_4$.

19. A powder comprising:
a) a cholera toxin B subunit variant comprising an amino acid sequence that has at least about 80% sequence identity to at least one sequence set forth in SEQ ID NO:4 or SEQ ID NO:34, and
b) mannitol, KCl, $KH_2PO_4$, NaCl, and $Na_2HPO_4$,
wherein the cholera toxin B subunit variant and mannitol have a weight ratio of between about 1:3.6 and about 1:45.5.

20. A method of treating colitis, comprising administering to a subject in need thereof an effective amount of the pharmaceutical composition of claim 12.

* * * * *

SEQUENCE LISTING

```
<160> NUMBER OF SEQ ID NOS: 34

<210> SEQ ID NO 1
<211> LENGTH: 309
<212> TYPE: DNA
<213> ORGANISM: Vibrio cholerae

<400> SEQUENCE: 1
accccacaaa acatcactga cttgtgtgct gagtaccaca acacccaaat ccacaccctc      60
aatgacaaga tctttagcta caccgagagc cttgctggca agagggagat ggctatcatc     120
accttcaaga atggtgctac cttccaagtg gaggtgcctg gaagccaaca cattgatagc     180
caaaagaagg ccattgagag gatgaaggac acacttagga tagcttacct cactgaggct     240
aaggtggaga agctttgtgt gtggaacaac aagaccccc atgctattgc tgccatcagc      300
atggccaac                                                             309

<210> SEQ ID NO 2
<211> LENGTH: 103
<212> TYPE: PRT
<213> ORGANISM: Vibrio cholerae
```

```
<400> SEQUENCE: 2

Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100

<210> SEQ ID NO 3
<211> LENGTH: 327
<212> TYPE: DNA
<213> ORGANISM: Artificial Sequence
<220> FEATURE:
<223> OTHER INFORMATION: modified cholera toxin B subunit variant
      polypeptide

<400> SEQUENCE: 3
accccacaaa gcatcactga cttgtgtgct gagtaccaca acacccaaat ccacaccctc     60
aatgacaaga tctttagcta caccgagagc cttgctggca agagggagat ggctatcatc   120
accttcaaga atggtgctac cttccaagtg gaggtgcctg gaagccaaca cattgatagc   180
caaaagaagg ccattgagag gatgaaggac acacttagga tagcttacct cactgaggct   240
aaggtggaga agctttgtgt gtggaacaac aagaccccccc atgctattgc tgccatcagc   300
atggccaact ccgagaagga tgaactc                                         327

<210> SEQ ID NO 4
<211> LENGTH: 109
<212> TYPE: PRT
<213> ORGANISM: Artificial Sequence
<220> FEATURE:
<223> OTHER INFORMATION: modified cholera toxin B subunit variant
      polypeptide

<400> SEQUENCE: 4

Thr Pro Gln Ser Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Ser Glu Lys Asp Glu Leu
            100                 105
```

```
<210> SEQ ID NO 5
<211> LENGTH: 327
<212> TYPE: DNA
<213> ORGANISM: Artificial Sequence
<220> FEATURE:
<223> OTHER INFORMATION: modified cholera toxin B subunit variant
      polypeptide

<400> SEQUENCE: 5
accccacaaa acatcactga cttgtgtgct gagtaccaca cacccaaat ccacaccctc     60 aatgacaaga tctttagcta caccgagagc cttgctggca agagggagat ggctatcatc    120
accttcaaga atggtgctac cttccaagtg gaggtgcctg gaagccaaca cattgatagc    180
caaaagaagg ccattgagag gatgaaggac acacttagga tagcttacct cactgaggct    240
aaggtggaga agctttgtgt gtggaacaac aagaccccc atgctattgc tgccatcagc     300
atggccaact ccgagaagga tgaactc                                        327

<210> SEQ ID NO 6
<211> LENGTH: 109
<212> TYPE: PRT
<213> ORGANISM: Artificial Sequence
<220> FEATURE:
<223> OTHER INFORMATION: modified cholera toxin B subunit variant
      polypeptide

<400> SEQUENCE: 6

Thr Pro Gln Asn Ile Thr Asp Leu Cys Ala Glu Tyr His Asn Thr Gln
 1               5                  10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Ser Glu Lys Asp Glu Leu
            100                 105

<210> SEQ ID NO 7
<211> LENGTH: 327
<212> TYPE: DNA
<213> ORGANISM: Artificial Sequence
<220> FEATURE:
<223> OTHER INFORMATION: modified cholera toxin B subunit variant
      polypeptide

<400> SEQUENCE: 7
accccacaaa acatcactga cttgtgtgct gagtaccaca cacccaaat ccacaccctc     60 aatgacaaga tctttagcta caccgagagc cttgctggca agagggagat ggctatcatc    120
accttcaaga atggtgctac cttccaagtg gaggtgcctg gaagccaaca cattgatagc    180
caaaagaagg ccattgagag gatgaaggac acacttagga tagcttacct cactgaggct    240
aaggtggaga agctttgtgt gtggaacaac aagaccccc atgctattgc tgccatcagc     300
atggccaacg ttactaagga tgaactc                                        327

<210> SEQ ID NO 8
```

<211> LENGTH: 109
<212> TYPE: PRT
<213> ORGANISM: Artificial Sequence
<220> FEATURE:
<223> OTHER INFORMATION: modified cholera toxin B subunit variant polypeptide

<400> SEQUENCE: 8

```
Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Val Thr Lys Asp Glu Leu
            100                 105
```

<210> SEQ ID NO 9
<211> LENGTH: 327
<212> TYPE: DNA
<213> ORGANISM: Artificial Sequence
<220> FEATURE:
<223> OTHER INFORMATION: modified cholera toxin B subunit variant polypeptide

<400> SEQUENCE: 9

```
accccacaaa acatcactga cttgtgtgct gagtaccaca acacccaaat ccacacccte    60
aatgacacta tctttagcta caccgagagc cttgctggca agagggagat ggctatcatc   120
accttcaaga atggtgctac cttccaagtg gaggtgcctg gaagccaaca cattgatagc   180
caaaagaagg ccattgagag gatgaaggac acacttagga tagcttacct cactgaggct   240
aaggtggaga agctttgtgt gtggaacaac aagacccccc atgctattgc tgccatcagc   300
atggccaact ccgagaagga tgaactc                                       327
```

<210> SEQ ID NO 10
<211> LENGTH: 109
<212> TYPE: PRT
<213> ORGANISM: Artificial Sequence
<220> FEATURE:
<223> OTHER INFORMATION: modified cholera toxin B subunit variant polypeptide

<400> SEQUENCE: 10

```
Thr Pro Gln Asn Ile Thr Asp Leu Cys Ala Glu Tyr His Asn Thr Gln
1               5                   10                  15

Ile His Thr Leu Asn Asp Thr Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80
```

```
Lys Val Glu Lys Leu Cys Val Trp Asn Asn Lys Thr Pro His Ala Ile
            85                  90                  95

Ala Ala Ile Ser Met Ala Asn Ser Glu Lys Asp Glu Leu
            100                 105

<210> SEQ ID NO 11
<211> LENGTH: 327
<212> TYPE: DNA
<213> ORGANISM: Artificial Sequence
<220> FEATURE:
<223> OTHER INFORMATION: modified cholera toxin B subunit variant
      polypeptide

<400> SEQUENCE: 11
accccacaaa acatcactga cttgtgtgct gagtaccaca cacccaaat ccacaccctc      60 aatgacacta tctttagcta caccgagagc cttgctggca agaggagat ggctatcatc     120 accttcaaga atggtgctac cttccaagtg gaggtgcctg gaagccaaca cattgatagc    180
caaaagaagg ccattgagag gatgaaggac acacttagga tagcttacct cactgaggct    240
aaggtggaga agctttgtgt gtggaacaac aagaccccc atgctattgc tgccatcagc     300
atggccaacg ttactaagga tgaactc                                        327

<210> SEQ ID NO 12
<211> LENGTH: 109
<212> TYPE: PRT
<213> ORGANISM: Artificial Sequence
<220> FEATURE:
<223> OTHER INFORMATION: modified cholera toxin B subunit variant
      polypeptide

<400> SEQUENCE: 12

Thr Pro Gln Asn Ile Thr Asp Leu Cys Ala Glu Tyr His Asn Thr Gln
1               5                   10                  15

Ile His Thr Leu Asn Asp Thr Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
            85                  90                  95

Ala Ala Ile Ser Met Ala Asn Val Thr Lys Asp Glu Leu
            100                 105

<210> SEQ ID NO 13
<211> LENGTH: 345
<212> TYPE: DNA
<213> ORGANISM: Artificial Sequence
<220> FEATURE:
<223> OTHER INFORMATION: modified cholera toxin B subunit variant
      polypeptide

<400> SEQUENCE: 13
accccacaaa acatcactga cttgtgtgct gagtaccaca cacccaaat ccacaccctc      60 aatgacacta tctttagcta caccgagagc cttgctggca agaggagat ggctatcatc     120 accttcaaga atggtgctac cttccaagtg gaggtgcctg gaagccaaca cattgatagc    180
caaaagaagg ccattgagag gatgaaggac acacttagga tagcttacct cactgaggct    240
```
aaggtggaga agctttgtgt gtggaacaac aagacccccc atgctattgc tgccatcagc    300
atggccaacg ttactggtgg tggaggatcc gagaaggatg aactc                    345

<210> SEQ ID NO 14
<211> LENGTH: 115
<212> TYPE: PRT
<213> ORGANISM: Artificial Sequence
<220> FEATURE:
<223> OTHER INFORMATION: modified cholera toxin B subunit variant
      polypeptide

<400> SEQUENCE: 14

Thr Pro Gln Asn Ile Thr Asp Leu Cys Ala Glu Tyr His Asn Thr Gln
1               5                   10                  15

Ile His Thr Leu Asn Asp Thr Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Val Thr Gly Gly Gly Ser Glu Lys
            100                 105                 110

Asp Glu Leu
        115

<210> SEQ ID NO 15
<211> LENGTH: 393
<212> TYPE: DNA
<213> ORGANISM: Artificial Sequence
<220> FEATURE:
<223> OTHER INFORMATION: modified cholera toxin B subunit variant
      polypeptide

<400> SEQUENCE: 15
atggctatca agctcaagtt tggagtgttc ttcactgtgc tccttagctc tgcctatgca     60
catggcaccc cacaaaacat cactgacttg tgtgctgagt accacaacac ccaaatccac    120
accctcaatg acaagatctt tagctacacc gagagccttg ctggcaagag ggagatggct    180
atcatcacct tcaagaatgg tgctaccttc caagtggagg tgcctggaag ccaacacatt    240
gatagccaaa agaaggccat tgagaggatg aaggacacac ttaggatagc ttacctcact    300
gaggctaagg tggagaagct ttgtgtgtgg aacaacaaga cccccatgc tattgctgcc    360 atcagcatgg ccaactccga aaggatgaa ctc                                 393

<210> SEQ ID NO 16
<211> LENGTH: 131
<212> TYPE: PRT
<213> ORGANISM: Artificial Sequence
<220> FEATURE:
<223> OTHER INFORMATION: modified cholera toxin B subunit variant
      polypeptide

<400> SEQUENCE: 16

Met Ala Ile Lys Leu Lys Phe Gly Val Phe Phe Thr Val Leu Leu Ser
1               5                   10                  15

Ser Ala Tyr Ala His Gly Thr Pro Gln Asn Ile Thr Asp Leu Cys Ala
            20                  25                  30

Glu Tyr His Asn Thr Gln Ile His Thr Leu Asn Asp Lys Ile Phe Ser
        35                  40                  45

Tyr Thr Glu Ser Leu Ala Gly Lys Arg Glu Met Ala Ile Ile Thr Phe
    50                  55                  60

Lys Asn Gly Ala Thr Phe Gln Val Glu Val Pro Gly Ser Gln His Ile
65                  70                  75                  80

Asp Ser Gln Lys Lys Ala Ile Glu Arg Met Lys Asp Thr Leu Arg Ile
                85                  90                  95

Ala Tyr Leu Thr Glu Ala Lys Val Glu Lys Leu Cys Val Trp Asn Asn
            100                 105                 110

Lys Thr Pro His Ala Ile Ala Ala Ile Ser Met Ala Asn Ser Glu Lys
        115                 120                 125

Asp Glu Leu
    130

<210> SEQ ID NO 17
<211> LENGTH: 78
<212> TYPE: DNA
<213> ORGANISM: Oryza sativa

<400> SEQUENCE: 17
atggggaagc aaatggccgc cctgtgtggc tttctcctcg tggcgttgct ctggctcacg      60
cccgacgtcg cgcatggt                                                    78

<210> SEQ ID NO 18
<211> LENGTH: 26
<212> TYPE: PRT
<213> ORGANISM: Oryza sativa

<400> SEQUENCE: 18

Met Gly Lys Gln Met Ala Ala Leu Cys Gly Phe Leu Leu Val Ala Leu
1               5                   10                  15

Leu Trp Leu Thr Pro Asp Val Ala His Gly
            20                  25

<210> SEQ ID NO 19
<211> LENGTH: 81
<212> TYPE: DNA
<213> ORGANISM: Nicotiana plumbaginifolia

<400> SEQUENCE: 19
atggctactc aacgaagggc aaaccctagc tctctccatc taattactgt attctctctg      60
ctcgtcgctg tcgtctcagg t                                                81

<210> SEQ ID NO 20
<211> LENGTH: 27
<212> TYPE: PRT
<213> ORGANISM: Nicotiana plumbaginifolia

<400> SEQUENCE: 20

Met Ala Thr Gln Arg Arg Ala Asn Pro Ser Ser Leu His Leu Ile Thr
1               5                   10                  15

Val Phe Ser Leu Leu Val Ala Val Val Ser Gly
            20                  25

<210> SEQ ID NO 21
<211> LENGTH: 78

```
<212> TYPE: DNA
<213> ORGANISM: Malus domestica

<400> SEQUENCE: 21
atggcattga agacacagtt gttgtggtca ttcgtggttg tgttcgttgt gtccttcagt    60
acaacttcat gctcaggt                                                  78

<210> SEQ ID NO 22
<211> LENGTH: 26
<212> TYPE: PRT
<213> ORGANISM: Malus domestica

<400> SEQUENCE: 22

Met Ala Leu Lys Thr Gln Leu Leu Trp Ser Phe Val Val Phe Val
1               5                  10                  15

Val Ser Phe Ser Thr Thr Ser Cys Ser Gly
            20                  25

<210> SEQ ID NO 23
<211> LENGTH: 72
<212> TYPE: DNA
<213> ORGANISM: Hordeum vulgare

<400> SEQUENCE: 23
atggcgaaca acacttgtc cctctccctc ttcctcgtcc tccttggcct gtcggccagc    60
ttggcctcag gt                                                        72

<210> SEQ ID NO 24
<211> LENGTH: 24
<212> TYPE: PRT
<213> ORGANISM: Hordeum vulgare

<400> SEQUENCE: 24

Met Ala Asn Lys His Leu Ser Leu Ser Leu Phe Leu Val Leu Leu Gly
1               5                  10                  15

Leu Ser Ala Ser Leu Ala Ser Gly
            20

<210> SEQ ID NO 25
<211> LENGTH: 109
<212> TYPE: PRT
<213> ORGANISM: Artificial Sequence
<220> FEATURE:
<223> OTHER INFORMATION: modified cholera toxin B subunit variant
      polypeptide

<400> SEQUENCE: 25

Thr Pro Gln Asn Ile Thr Asp Leu Cys Ala Glu Tyr His Asn Thr Gln
1               5                  10                  15

Ile His Thr Leu Asn Asp Lys Ile Phe Cys Tyr Thr Glu Ser Leu Ala
            20                  25                  30

Gly Lys Arg Glu Met Ala Ile Ile Thr Phe Lys Asn Gly Ala Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Cys Asn Ser Glu Lys Asp Glu Leu
```

```
                    100                 105

<210> SEQ ID NO 26
<211> LENGTH: 135
<212> TYPE: PRT
<213> ORGANISM: Artificial Sequence
<220> FEATURE:
<223> OTHER INFORMATION: modified cholera toxin B subunit variant
      polypeptide

<400> SEQUENCE: 26

Met Gly Lys Gln Met Ala Ala Leu Cys Gly Phe Leu Leu Val Ala Leu
1               5                   10                  15

Leu Trp Leu Thr Pro Asp Val Ala His Gly Thr Pro Gln Asn Ile Thr
            20                  25                  30

Asp Leu Cys Ala Glu Tyr His Asn Thr Gln Ile His Thr Leu Asn Asp
        35                  40                  45

Lys Ile Phe Ser Tyr Thr Glu Ser Leu Ala Gly Lys Arg Glu Met Ala
    50                  55                  60

Ile Ile Thr Phe Lys Asn Gly Ala Thr Phe Gln Val Glu Val Pro Gly
65                  70                  75                  80

Ser Gln His Ile Asp Ser Gln Lys Lys Ala Ile Glu Arg Met Lys Asp
                85                  90                  95

Thr Leu Arg Ile Ala Tyr Leu Thr Glu Ala Lys Val Glu Lys Leu Cys
            100                 105                 110

Val Trp Asn Asn Lys Thr Pro His Ala Ile Ala Ala Ile Ser Met Ala
        115                 120                 125

Asn Ser Glu Lys Asp Glu Leu
    130                 135

<210> SEQ ID NO 27
<211> LENGTH: 136
<212> TYPE: PRT
<213> ORGANISM: Artificial Sequence
<220> FEATURE:
<223> OTHER INFORMATION: modified cholera toxin B subunit variant
      polypeptide

<400> SEQUENCE: 27

Met Ala Thr Gln Arg Arg Ala Asn Pro Ser Ser Leu His Leu Ile Thr
1               5                   10                  15

Val Phe Ser Leu Leu Val Ala Val Ser Gly Thr Pro Gln Asn Ile
            20                  25                  30

Thr Asp Leu Cys Ala Glu Tyr His Asn Thr Gln Ile His Thr Leu Asn
        35                  40                  45

Asp Lys Ile Phe Ser Tyr Thr Glu Ser Leu Ala Gly Lys Arg Glu Met
    50                  55                  60

Ala Ile Ile Thr Phe Lys Asn Gly Ala Thr Phe Gln Val Glu Val Pro
65                  70                  75                  80

Gly Ser Gln His Ile Asp Ser Gln Lys Lys Ala Ile Glu Arg Met Lys
                85                  90                  95

Asp Thr Leu Arg Ile Ala Tyr Leu Thr Glu Ala Lys Val Glu Lys Leu
            100                 105                 110

Cys Val Trp Asn Asn Lys Thr Pro His Ala Ile Ala Ala Ile Ser Met
        115                 120                 125

Ala Asn Ser Glu Lys Asp Glu Leu
    130                 135
```

<210> SEQ ID NO 28
<211> LENGTH: 135
<212> TYPE: PRT
<213> ORGANISM: Artificial Sequence
<220> FEATURE:
<223> OTHER INFORMATION: modified cholera toxin B subunit variant polypeptide

<400> SEQUENCE: 28

```
Met Ala Leu Lys Thr Gln Leu Leu Trp Ser Phe Val Val Phe Val
1               5                   10                  15

Val Ser Phe Ser Thr Thr Ser Cys Ser Gly Thr Pro Gln Asn Ile Thr
            20                  25                  30

Asp Leu Cys Ala Glu Tyr His Asn Thr Gln Ile His Thr Leu Asn Asp
            35                  40                  45

Lys Ile Phe Ser Tyr Thr Glu Ser Leu Ala Gly Lys Arg Glu Met Ala
50                  55                  60

Ile Ile Thr Phe Lys Asn Gly Ala Thr Phe Gln Val Glu Val Pro Gly
65                  70                  75                  80

Ser Gln His Ile Asp Ser Gln Lys Lys Ala Ile Glu Arg Met Lys Asp
            85                  90                  95

Thr Leu Arg Ile Ala Tyr Leu Thr Glu Ala Lys Val Glu Lys Leu Cys
            100                 105                 110

Val Trp Asn Asn Lys Thr Pro His Ala Ile Ala Ala Ile Ser Met Ala
            115                 120                 125

Asn Ser Glu Lys Asp Glu Leu
    130                 135
```

<210> SEQ ID NO 29
<211> LENGTH: 133
<212> TYPE: PRT
<213> ORGANISM: Artificial Sequence
<220> FEATURE:
<223> OTHER INFORMATION: modified cholera toxin B subunit variant polypeptide

<400> SEQUENCE: 29

```
Met Ala Asn Lys His Leu Ser Leu Ser Leu Phe Leu Val Leu Leu Gly
1               5                   10                  15

Leu Ser Ala Ser Leu Ala Ser Gly Thr Pro Gln Asn Ile Thr Asp Leu
            20                  25                  30

Cys Ala Glu Tyr His Asn Thr Gln Ile His Thr Leu Asn Asp Lys Ile
            35                  40                  45

Phe Ser Tyr Thr Glu Ser Leu Ala Gly Lys Arg Glu Met Ala Ile Ile
50                  55                  60

Thr Phe Lys Asn Gly Ala Thr Phe Gln Val Glu Val Pro Gly Ser Gln
65                  70                  75                  80

His Ile Asp Ser Gln Lys Lys Ala Ile Glu Arg Met Lys Asp Thr Leu
            85                  90                  95

Arg Ile Ala Tyr Leu Thr Glu Ala Lys Val Glu Lys Leu Cys Val Trp
            100                 105                 110

Asn Asn Lys Thr Pro His Ala Ile Ala Ala Ile Ser Met Ala Asn Ser
            115                 120                 125

Glu Lys Asp Glu Leu
    130
```

<210> SEQ ID NO 30
<211> LENGTH: 6
<212> TYPE: PRT

-continued

<210> SEQ ID NO 31
<211> LENGTH: 4
<212> TYPE: PRT
<213> ORGANISM: Artificial Sequence
<220> FEATURE:
<223> OTHER INFORMATION: Endoplasmic Reticulum Retention Signal

<400> SEQUENCE: 30

Ser Glu Lys Asp Glu Leu
1               5

<210> SEQ ID NO 31
<211> LENGTH: 4
<212> TYPE: PRT
<213> ORGANISM: Artificial Sequence
<220> FEATURE:
<223> OTHER INFORMATION: Endoplasmic Reticulum Retention Signal

<400> SEQUENCE: 31

Lys Asp Glu Leu
1

<210> SEQ ID NO 32
<211> LENGTH: 6
<212> TYPE: PRT
<213> ORGANISM: Artificial Sequence
<220> FEATURE:
<223> OTHER INFORMATION: Endoplasmic Reticulum Retention Signal

<400> SEQUENCE: 32

Ser Glu His Asp Glu Leu
1               5

<210> SEQ ID NO 33
<211> LENGTH: 4
<212> TYPE: PRT
<213> ORGANISM: Artificial Sequence
<220> FEATURE:
<223> OTHER INFORMATION: Endoplasmic Reticulum Retention Signal

<400> SEQUENCE: 33

His Asp Glu Leu
1

<210> SEQ ID NO 34
<211> LENGTH: 135
<212> TYPE: PRT
<213> ORGANISM: Artificial Sequence
<220> FEATURE:
<223> OTHER INFORMATION: modified cholera toxin B subunit variant
      polypeptide

<400> SEQUENCE: 34

Met Gly Lys Gln Met Ala Ala Leu Cys Gly Phe Leu Leu Val Ala Leu
1               5                   10                  15

Leu Trp Leu Thr Pro Asp Val Ala His Gly Thr Pro Gln Ser Ile Thr
            20                  25                  30

Asp Leu Cys Ala Glu Tyr His Asn Thr Gln Ile His Thr Leu Asn Asp
        35                  40                  45

Lys Ile Phe Ser Tyr Thr Glu Ser Leu Ala Gly Lys Arg Glu Met Ala
    50                  55                  60

Ile Ile Thr Phe Lys Asn Gly Ala Thr Phe Gln Val Glu Val Pro Gly
65                  70                  75                  80

Ser Gln His Ile Asp Ser Gln Lys Lys Ala Ile Glu Arg Met Lys Asp
                85                  90                  95

Thr Leu Arg Ile Ala Tyr Leu Thr Glu Ala Lys Val Glu Lys Leu Cys
            100                 105                 110

```
Val Trp Asn Asn Lys Thr Pro His Ala Ile Ala Ala Ile Ser Met Ala
        115                 120                 125
Asn Ser Glu Lys Asp Glu Leu
    130                 135
```